US006800285B2

(12) United States Patent
Rodriguez et al.

(10) Patent No.: US 6,800,285 B2
(45) Date of Patent: Oct. 5, 2004

(54) TREATMENT OF CENTRAL NERVOUS SYSTEM DISEASES BY ANTIBODIES AGAINST GLATIRAMER ACETATE

(76) Inventors: Moses Rodriguez, 2402 Hillside La., SW., Rochester, MN (US) 55902; Daren Ure, 2315 22nd St. NW., Rochester, MN (US) 55901

( * ) Notice: Subject to any disclaimer, the term of this patent is extended or adjusted under 35 U.S.C. 154(b) by 0 days.

(21) Appl. No.: 09/885,227

(22) Filed: Jun. 20, 2001

(65) Prior Publication Data

US 2002/0182210 A1 Dec. 5, 2002

Related U.S. Application Data

(60) Provisional application No. 60/287,171, filed on Apr. 27, 2001, provisional application No. 60/269,788, filed on Feb. 16, 2001, and provisional application No. 60/212,577, filed on Jun. 20, 2000.

(51) Int. Cl.[7] .................... A61K 39/395; A61K 39/40; A61K 39/42; C07K 16/00; C12P 21/08
(52) U.S. Cl. ............................... 424/133.1; 424/130.1; 424/141.1; 424/139.1; 530/387.1; 530/387.3; 530/387.9; 530/388.1
(58) Field of Search .......................... 424/133.1, 130.1, 424/141.1, 139.1; 530/387.1, 387.3, 387.9, 388.1

(56) References Cited

U.S. PATENT DOCUMENTS

| | | | |
|---|---|---|---|
| 3,849,550 A | 11/1974 | Teitelbaum et al. |
| 3,991,210 A | 11/1976 | Shea |
| 4,339,431 A | 7/1982 | Gaffar |
| 5,204,099 A | 4/1993 | Barbier et al. |
| 5,554,372 A | 9/1996 | Hunter |
| 5,583,031 A | 12/1996 | Stern |
| 5,591,629 A | 1/1997 | Rodriguez et al. |
| 5,623,052 A | 4/1997 | McLean et al. |
| 5,627,206 A | 5/1997 | Hupe et al. |
| 5,668,117 A | 9/1997 | Shapiro et al. |
| 5,719,296 A | 2/1998 | Acton, III et al. |
| 5,734,023 A | 3/1998 | Nag et al. |
| 5,800,808 A | 9/1998 | Konfino et al. |
| 5,858,964 A | 1/1999 | Aharoni et al. |
| 5,886,156 A | 3/1999 | McLean et al. |
| 5,958,972 A | 9/1999 | Hupe et al. |
| 5,981,589 A | 11/1999 | Konfino et al. |
| 6,048,898 A | 4/2000 | Konfino et al. |
| 6,054,430 A | 4/2000 | Konfino et al. |
| 6,214,791 B1 | 4/2001 | Arnon et al. |
| 6,342,476 B1 | 1/2002 | Konfino et al. |
| 6,362,161 B1 | 3/2002 | Konfino et al. |
| 2001/0055568 A1 | 12/2001 | Gilbert et al. |
| 2002/0037848 A1 | 3/2002 | Eisenbach-Schwartz et al. |
| 2003/0004099 A1 | 1/2003 | Eisenbach-Schwartz et al. |

FOREIGN PATENT DOCUMENTS

| | | |
|---|---|---|
| EP | 0383620 | 8/1990 |
| EP | 0359783 | 11/1995 |
| WO | WO8810120 | 12/1988 |
| WO | WO9202543 | 2/1992 |
| WO | WO9403484 | 2/1994 |
| WO | WO9426774 | 11/1994 |
| WO | WO9526980 | 10/1995 |
| WO | WO9531990 | 11/1995 |
| WO | WO9531997 | 11/1995 |
| WO | WO9533475 | 12/1995 |
| WO | WO9830227 | 7/1998 |
| WO | WO0005249 | 2/2000 |
| WO | WO0005250 | 2/2000 |
| WO | WO0018794 | 4/2000 |
| WO | WO0020010 | 4/2000 |
| WO | WO0027417 | 5/2000 |
| WO | WO0152878 | 7/2001 |
| WO | WO0160392 | 8/2001 |
| WO | WO0185797 | 11/2001 |
| WO | WO0193828 | 12/2001 |
| WO | WO0193893 | 12/2001 |
| WO | WO0197846 | 12/2001 |

OTHER PUBLICATIONS

U.S. patent application Ser. No. 09/875,429, Yong et al., filed Jun. 5, 2001.

Harrison and Hafler, "Antigen–Specific Therapy for Autoimmune Disease", Current Opin. Immunol., 2000, 12(6): 704–711.

Pender et al., Int. Med. Journal, 2002, 32 554–563.

Van Noort et al., International Review of Cytology, 1995, 178: 127–205.

Webster's II New Riverside University Dictionary. The Riverside Publishing Company, 1984, 933.

Teitelbaum, et al., "Suppression of Experimental Allergic Encephalomyelitis by a Synthetic Polypeptide", Israel J. Med. Sci., 1971, 7, 630–631 (Abstract).

Teitelbaum, et al., "Suppression of Experimental Allergic Encephalomyelitis by a Synthetic Polypeptide", Eur. J. Immunol., 1971, 1, 242–248.

(List continued on next page.)

Primary Examiner—John Ulm
Assistant Examiner—Olga N. Chernyshev
(74) Attorney, Agent, or Firm—John P. White; Cooper & Dunham LLP

(57) ABSTRACT

The present invention provides humanized polyclonal and humanized monoclonal antibodies directed against an epitope on glatiramer acetate, also known as Copolymer 1, Copolymer-1, Cop-1 or Cop. Additionally, the subject invention concerns a pharmaceutical composition comprising an antibody directed against an epitope on glatiramer acetate for the treatment of a disease associated with demyelination of central nervous system axons. Also encompassed by the subject invention is a method of treating a subject suffering from a disease associated with demyelination of central nervous system axons. The subject invention further contains methods of stimulating remyelination of central nervous system axons. In addition, the subject invention provides a method of stimulating proliferation of lymphocytes.

14 Claims, 32 Drawing Sheets

OTHER PUBLICATIONS

Arnon, et al., "Suppression of Experimental Allergic Encephalomyelitis by a Synthetic Copolymer Immunological Cross Reactive with Basic Encephalitogen", *Israel J. Med. Sci.*, 1972, 8, 1759–1760.

Teitelbaum, et al., "Protection Against Experimental Allergic Encephalomyelitis", *Nature*, 1972, 240, 564–566.

Webb, et al., "Further Studies on the Suppression of Experimental Allergic Encephalomyelitis by Synthetic Copolymer", *Israel J. Med. Sci.*, 1972, 8, 656–657.

Teitelbaum, et al., "Suppression of Experimental Allergic Encephalomyelitis with Basic Polymers", *Eur. J. Immunol.*, 1973, 3, 273–279.

Webb et al., "In Vivo and in Vitro Immunological Cross–reactions between Basic Encephalitogen and Synthetic Basic Polypeptides Capable of Suppressing Experimental Allergic Encephalomyelitis", *Eur. J. Immunol.*, 1973, 3, 279–286.

Teitelbaum, et al., "Dose–response Studies on Experimental Allergic Encephalomyelitis Suppression by COP–1", *Israel J. Med. Sci.*, 1974, 10(9), 1172–1173.

Teitelbaum, et al., "Suppression of Experimental Allergic Encephalomyelitis in Rhesus Monkeys by a Synthetic Basic Copolymer", *Clin. Immunol. Immunopath.*, 1974, 3, 256–262.

Webb, et al., "Suppression of Experimental Allergic Encephalomyelitis in Rhesus Monkeys by a Synthetic Basic Copolymer", *Isr. J. Med. Sci.*, 1975, 11, 1388 (Abstract).

Webb, et al., "Molecular Requirements Involved in Suppression of EAE by Synthetic Basic Copolymers of Amino Acids", *Immunochem.*, 1976, 13, 333–337.

Abramsky, et al., "Effect of a Synthetic Polypeptide (COP–1) on Patients with Multiple Sclerosis and with Acute Disseminated Encephalomyelitis", *J. Neurol. Sci.*, 1977, 31, 433–438.

U.S. patent application Ser. No. 09/359,099, Strominger et al., filed Jul. 22, 1999.

U.S. patent application Ser. No. 09/405,743, Gad et al., filed Sep. 24, 1999.

U.S. patent application Ser. No. 09/768,872, Aharoni et al., filed Jan. 23, 2001.

U.S. patent application Ser. No. 09/816,989, Gad et al., filed Mar. 23, 2001.

Teitelbaum, et al., "Suppression of Experimental Allergic Encephalomyelitis in Baboons by COP 1", *Israel J. Med. Sci.*, 1977, 13, 1038 (Abstract).

Arnon, et al., "Suppression of EAE in Baboons by a Synthetic Polymer of Amino Acids", *Neurol.*, 1978, 28, 336 (Abstract).

Sela, et al., "Experimental Allergic Encephalomyelitis" in *Menarini Series on Immunopathology, vol. 1, First Symposium of Organ Specific Autoimmunity*, Cremona, Italy, Jun., 1977, (Miescher P.A. ed., Schwabe Co., Basel, 1978), 9–21.

Alvord, et al., "Myelin Basic Protein Treatment of Experimental Allergic Encephalomyelitis in Monkeys", *Ann. Neurol.*, 1979, 6, 469–473.

Keith, et al., "The Effect of COP 1, a Synthetic Polypeptide, on Chronic Relapsing Experimental Allergic Encephalomyelitis in Guinea Pigs" *J. Neurol. Sci.*, 1979, 42, 267–274.

Lando, et al., "Effect of Cyclophosphamide on Suppressor Cell Activity in Mice Unresponsive to EAE", *J. Immunol.*, 1979, 123, 2156–2160 (Abstract).

Lando, et al., "Experimental Allergic Encephalomyelitis in Mice Suppression and Prevention with COP–1", *Israel J. Med. Sci.*, 1979, 15, 868–869 (Abstract).

Teitelbaum, et al., "Blocking of Sensitization to Encephalitogenic Basic Protein in Vitro by Synthetic Basic Copolymer (COP 1)" in *Cell Biology and Immunology of Leukocyte Function* Academic Press, New York, 1979) 681–685.

Teitelbaum, "Suppression of Experimental Allergic Encephalomyelitis with a Synthetic Copolymer—Relevance to Multiple Sclerosis", in *Humoral Immunity in Neurological Diseases* (Karcher D., Lowenthal A. & Strosberg A.D., eds., Plenum Publishing Corp., 1979) 609–613.

Arnon, et al., "Desensitization of Experimental Allergic Encephalomyelitis with Synthetic Peptide Analogues" in *The Suppression of Experimental Allergic Encephalomyelitis and Multiple Sclerosis* (Academic Press, New York, 1980) 105–107.

Arnon, "A Synthetic Copolymer of Amino Acids in a Clinical Trial for MS Therapy" in *Progress in Multiple Sclerosis Research* (Bauer, Ritter, eds., Springer Verlag New York, 1980) 416–418.

Bornstein, et al., "Treatment of Multiple Sclerosis with a Synthetic Polypeptide: Preliminary Results", *Ann. Neurol.*, 1980, 8, 117 (Abstract).

Bornstein, et al., "Treatment of Multiple Sclerosis with a Synthetic Polypeptide: Preliminary Results", *Trans. Am. Neurol. Assoc.*, 1980, 105, 348–350.

McDermott, et al., "Antigen–induced Suppression of Experimental Allergic Neuritis in the Guinea Pig", *J. Neurol. Sci.*, 1980, 46, 137–143.

Arnon, "Experimental Allergic Encephalomyelitis—Susceptibility and Suppression", *Immunological Rev.*, 1981, 55, 5–30.

Bornstein, et al., "Multiple Sclerosis: Trial of a Synthetic Polypeptide", *Ann. Neurol.*, 1982, 11, 317–319.

Brosnan, et al., "The Response of Normal Human Lymphocytes to Copolymer 1", *J. Neuropath. Exp. Neurol.*, 1983, 42, 356 (Abstract).

Lisak, et al., "Effect of Treatment with Copolymer 1 (Cop–1) on the in Vivo and in Vitro Manifestations of Experimental Allergic Encephalomyelitis (EAE)", *J. Neurol. Sci.*, 1983, 62, 281–293.

Bornstein, et al., "Clinical Trials of Copolymer 1 in Multiple Sclerosis", *Ann. N.Y. Acad. Sci. (USA)*, 1984, 366–372.

Bornstein, et al., "Clinical Trials of a Synthetic Polypeptide (Copolymer 1) for the Treatment of Multiple Sclerosis" in Gonsett et al., *Immunological and Clinical Aspects of Multiple Sclerosis* (MTP Press, The Hague, 1984) 144–150.

Brosnan, et al., "Copolymer 1: Effect on Normal Human Lymphocytes", *Ann. N.Y. Acad. Sci. (USA)*, 1984, 436, 498–499.

Bornstein, et al., "Multiple Sclerosis: Clinical Trials of a Synthetic Polypeptide, Copolymer 1", *Neurol.*, 1985, 35 (Suppl. 1), 103 (Abstract).

Brosnan, et al., "Immunogenic Potentials of Copolymer 1 in Normal Human Lymphocytes", *Neurol.*, 1985, 35, 1754–1759.

Burns, et al., "Human Cellular Immune Response in Vitro to Copolymer 1 and Myelin Basic Protein (MBP)", *Neurol.*, 1985, 35 (Suppl. 1), 170 (Abstract).

Teitelbaum, et al., "Monoclonal Antibodies to Myelin Basic Protein Cross React with Synthetic EAE–suppressive Copolymer, COP 1" in *Proc. 7th Eur. Immunol. Mtg.*, Jerusalem, Sep. 8–13, 1985 (Abstract).

Thompson, "MCQ Tutor: Medical Immunology Multiple Choice Questions", *Immunol. Today*, 1985, 6(4), 141.

Burns, et al., "Human Cellular Immune Response to Copolymer 1 and Myelin Basic Protein", *Neurol.*, 1986, 36, 92–94.

Bornstein, "Cop 1 May be Beneficial for Patients with Exacerbating–remitting Form of Multiple Sclerosis", *Adv. Ther. (USA)*, 1987, 4, 206 (Abstract).

Bornstein, et al., "A Pilot Trial of Cop 1 in Exacerbating—remitting Multiple Sclerosis", *New Eng. J. Med.*, 1987, 317(7), 408–414.

Rolak, "Copolymer–I Therapy for Multiple Sclerosis", *Clin. Neuropharmacology*, 1987, 10(5), 389–396.

Winer, "COP 1 Therapy for Multiple Sclerosis", *New Eng. J. Med.*, 1987, 317(7), 442–444.

Arnon, et al., "Suppression of Demyelinating Diseases by Synthetic Copolymers", in *A Multidisciplinary Approach to Myelin Disease* (G. Serlupi Crescenzi, ed., Plenum Publishing Corp., 1988) 243–250.

Baumhefner, et al., "Copolymer 1 as Therapy for Multiple Sclerosis: The Cons", *Neurol.*, 1988, 38(Suppl. 2), 69–71.

Bornstein, et al., "Clinical Experience with COP–1 in Multiple Sclerosis", *Neurol.*, 1988, 38(Suppl. 2), 66–69.

Teitelbaum, et al., "Specific Inhibition of the T–cell Response to Myelin Basic Protein by the Synthetic Copolymer Cop 1", *Proc. Natl. Acad. Sci. USA*, 1988, 85, 9724–9728.

Arnon, et al., "Suppression of Experimental Allergic Encephalomyelitis by Cop–1—Relevance to Multiple Sclerosis", *Israel J. Med. Sci.*, 1989, 25, 686–689.

Bornstein, et al., "Pilot Trial of COP–1 in Chronic Progressive Multiple Sclerosis: Preliminary Report", from *The International Multiple Sclerosis Conference: An Update on Multiple Sclerosis*, Roma (Italy), Sep. 15–17, 1988, in *Elsevier Science Publisher*, 1989, 225–232.

Teitelbaum, et al., "Clinical Trial of Copolymer 1 in Multiple Sclerosis" *J. Israel Med. Assoc.*, 1989, CXVI(9), 453–456.

Bornstein, et al., "Clinical Trials of Cop 1 in Multiple Sclerosis", in *Handbook of Multiple Sclerosis* (S.D. Cook Marcel Rekker, ed., 1990) 469–480.

Carter, et al., "Newer Drug Therapies for Multiple Sclerosis", *Drug Therapy*, 1990, 31–32, 37–39, 42–43.

Grgacic, et al., "Cell–mediated Immune Response to Copolymer 1 in Multiple Sclerosis Measured by the Macrophage Procoagulant Activity Assay", *Int. Immunol.*, 1990, 2(8), 713–718.

Kay, et al., "The Mechanism of Action of FK 506", *Transplantation Proceedings*, 1990, 22(1, Suppl. 1), 96–99.

Lee, et al., "Peptide and Protein Drug Delivery" in *Advances in Parenteral Sciences* (Vincent H.L. Lee, ed., Marcel Dekker, Inc., 1990) 691–695.

Myers, et al., "The Peculiar Difficulties of Therapeutic Trials for Multiple Sclerosis", *Neurologic Clinics*, 1990, 8(1), 119–141.

Sela, et al., "Suppressive Activity of COP–1 in EAE and its Relevance to Multiple Sclerosis", *Bull. Inst. Pasteur*, 1990, 88, 303–314.

Starzl, *Transplantation Proceedings*, 1990, 22 (1, Suppl. 1), 5.

Wender, "Copolymer 1 (COP–1) in the Treatment of Multiple Sclerosis (letter)" *Neur. Neurochir. Pol.*, 1990, 24, 113.

Bornstein, et al., "A Placebo–controlled, Double–blind, Randomized Two–center, Pilot Trial of Cop 1 in Chronic Progressive Multiple Sclerosis", *Neurol.*, 1991, 41, 533–539.

Burns, et al., "Failure of Copolymer 1 to Inhibit the Human T–cell Response to Myelin Basic Protein", *Neurol.*, 1991, 41, 1317–1319.

Clinical Trial Protocol No. 9001, Teva Pharmaceutical Industries, Ltd., first patient enrolled Oct. 23, 1991.

Ferrara, et al., "Graft–Versus–Host Disease", *New Eng. J. Med.*, 1991, 324, 667–674.

Meiner, "COP–1 Multicenter Clinical Trial in Exacerbating–remitting Multiple–Sclerosis: One Year Follow–up", *J. Neurol.*, 1991(Suppl. 1) (Abstract).

Rothbard, et al., "Interactions Between Immunogenic Peptides and MHC Proteins", *Ann. Rev. Immunol.*, 1991, 9, 527–565.

Salvetti, et al., "Myelin Basic Protein T Cell Epitopes in Patients with Multiple Sclerosis", *Department of Neurological Sciences, University of Rome, La Sapienza* 1991, 72 (Abstract).

Teitelbaum et al., "Cross–reactions and Specificities of Monoclonal Antibodies Against Myelin Basic Protein and Against the Synthetic Copolymer 1", *Proc. Natl. Acad. Sci. (USA)*, 1991, 88, 9528–9532.

Van den Bogaerde, et al., "Induction of Long–Term Survival of Hamster Heart Xenografts in Rats", *Transplantation*, 1991, 52, 15–20.

Bornstein, et al., "Treatment of Multiple Sclerosis with Copolymer 1" in *Treatment of Multiple Sclerosis: Trial Design, Results and Future Perspectives* (Rudick R.A. & Goodkin D.E., eds., Springer Verlag, London, 1992) 173–198.

Johnson, "Clinical Studies in Copolymer 1 Therapy for Exacerbating–remitting Multiple Sclerosis", in *Congress for Advances in the Understanding and Treatment of Multiple Sclerosis*, Boston (USA), Oct. 28–29, 1992.

Milo, et al., "Inhibition of Myelin Basic Protein–specific Human T–cell Lines by COP–1", *Israel J. Med. Sci.*, 1992, 28, 486 (Abstract).

Racke, et al., "Copolymer–1–induced Inhibition of Antigen–specific T Cell Activation: Interference with Antigen Presentation", *J. Neuroimmunol.*, 1992, 37, 75–84.

Teitelbaum, et al., "Synthetic Copolymer 1 Inhibits Human T–cell Lines Specific for Myelin Basic Protein", *Proc. Natl. Acad. Sci. (USA)*, 1992, 89, 137–141.

Weinshenker et al., "Natural History and Treatment of Multiple Sclerosis", *Current Opinion in Neurol. and Neurosurgery*, 1992, 5, 203–211.

Aharoni et al., "T Suppressor Hybridomas and Interleukin–2–Dependent Lines Induced by Copolymer 1 or by Spinal Cord Homogenate Down–Regulate Experimental Allergic Encephalomyelitis", *Eur. J. Immunol.*, 1993, 23, 17–25.

Arnon, et al., "Immunomodulation of Experimental Allergic Encephalomyelitis", *Israel J. Med. Sci.*, 1993, 29, 175–181.

Arnon, et al., "On the Existence of Suppressor Cells", *Int. Arch. Allergy Immunol.*, 1993, 100, 2–7.

Clinical Trial Protocol No. 9002, Lemmon Co. and Teva Pharmaceutical Industries, Ltd., first patient enrolled Jun. 17, 1993.

Francis, "The Current Therapy of Multiple Sclerosis", *J. Clin. Pharmacy and Therapeutics*, 1993, 18, 77–84.

Keleman, et al., "Graft–versus–Host Disease in Bone Marrow Transplantation: Experimental, Laboratory, and Clinical Contributions of the Last Few Years", *Int. Arch. Allergy Immunol.*, 1993, 102, 309–320.

Gurevich, "Study of the MHC–competition Between BP and Cop 1 Using Human Cytotoxic T–cell Clones", *Israel J. Med. Sci.*, 1993 (Abstract).

Meiner, et al., "The Israeli COP–1 Multicenter Clinical Trial in Exacerbating–remitting Multiple Sclerosis—Two–year Follow–up", in *9th Congress of the European Committee for Treatment and Research in Multiple Sclerosis*, Florence (Italy), Oct.–Nov., 1993, 48 (Abstract).

Milo, et al., "Copolymer–1 (COP–1) Regulates Class II MHC Expression and Cytokine Synthesis in the THP–1 Monocyte–Macrophage Cell Line" in *The IBC Conference on Multiple Sclerosis*, San Diego (USA), Dec. 10, 1993 (Abstract).

Sela, "Polymeric Drugs as Immunomodulatory Vaccines Against Multiple Sclerosis", *Makromol. Chem. Macromol. Symp.*, 1993, 70/71, 147–155.

Arnon, et al., "Immunospecific Drug Design—Prospects for Treatment of Autoimmune Disease", *Therapeutic Immunol.*, 1994, 1, 65–70.

Bansil, et al., "Multiple Sclerosis: Pathogenesis and Treatment", *Seminars in Neurol.*, Jun. 1994, 14(2), 146–153.

The COP–1 Multicenter Clinical and Research Group Study, "COP–1 Multicenter Trial in Relapsing Remitting Multiple Sclerosis: 3 Year Follow–Up", *Abstracts of Symposia and Free Communications*, Barcelona (Spain), Jun. 25–29, 1994, 241 (Suppl. 1), 6.

Cotton, "Options for Multiple Sclerosis Therapy", *J.A.M.A Medical News & Perspectives*, 1994, 272(18), 1393.

Dorling, et al., "Prospects for Xenografting", *Curr. Opinions Immunol.*, 1994, 6, 765–769.

Fridkis–Hareli, et al., "Copolymer 1 Displaces MBP, PLP and MOG, but Can Not be Displaced by these Antigens from the MHC Class II Binding Site", *Department of Chemical Immunology, The Weizmann Institute of Science*, 1994.

Fridkis–Hareli, et al., "Direct Binding of Myelin Basic Protein and Synthetic Copolymer 1 to Class II Major Histocompatibility Complex Molecules on Living Antigen–Presenting Cells—Specificity and Promiscuity", *Proc. Natl. Acad. Sci. USA*, 1994, 91, 4872–4876.

Fridkis–Hareli, et al., "Specific and Promiscuous Binding of Synthetic Copolymer 1 to Class II Major Histocompatibility Complex Molecules on Living Antigen Presenting Cells", *Israeli Biochem. Soc.*, 1994, 21–22 (Abstract).

Fridkis–Hareli, et al., "Synthetic Copolymer 1 Inhibits the Binding of MBP, PLP and MOG Peptides to Class II Major Histocompatibility Complex Molecules on Antigen Presenting Cells" in *Neurochem Mtg.*, Aug. 14–19, 1994.

Fridkis–Hareli, et al., "Synthetic Copolymer 1 Inhibits the Binding of MBP, PLP and MOG Peptides to Class II Major Hiscompatibility Complex Molecules on Antigen– Presenting Cells", *J. Neurochem.*, 1994, 53(Suppl.I), 561.

Fridkis–Hareli, et al., "Synthetic Copolymer 1 and Myelin Basic Protein Do Not Undergo Processing Prior to the Binding to Class II Major Histocompatibility Complex Molecules on Antigen Presenting Cells", *Israeli Immunol. Soc.*, May 3–4, 1994 (Abstract).

Fridkis–Hareli, et al., "Synthetic Copolymer 1 and Myelin Basic Protein do not Require Processing Prior to Binding to Class II Major Histocompatibility Complex Molecules on Living Antigen Presenting Cells", *Department of Chemical Immunology, The Weizmann Institute of Science*, Rehovot, Israel, 1994.

Fridkis–Hareli, et al., "Synthetic Copolymer 1 and Myelin Basic Protein Do Not Require Processing Prior to Binding to Class II Major Histocompatibility Complex Molecules on Living Antigen–Presenting Cells", *Cell. Immunol.*, 1995, 163, 229–236.

Jacobs et al., "Advances in Specific Therapy for Multiple Sclerosis", *Neurol.*, 1994, 7, 250–254.

Johnson, "Experimental Therapy of Relapsing–Remitting Multiple Sclerosis with Copolymer–1", *Ann. Neurol.*, 1994, 36(Suppl.), 115–117.

Kott, et al., "COP–1 Increases Suppressor Cells Number in Multiple Sclerosis", *Israel Neurological Assoc.*, Dec. 19–20, 1994, Herzliya (Israel), 17.

Mengle–Gaw, "The Major Histocompatibility Complex (MHC)", in *Encycl. Molecular Bio.* (Oxford Blackwell Science Ltd, 1994) 602–606.

Milo, et al., "Additive Effects of COP–1 and IFN–Beta on Immune Responses to Myelin Basic Protein", *Neurol.*, 1994, 44(Suppl. 2), A212.

Milo, et al., "Additive Effect of Copolymer–1 and Interferon–β on the Immune Response to Myelin Basic Protein", *Assaf Harofeh Medical Center, Sackler School of Medicine, Tel–Aviv University of Maryland School of Medicine*, 1994, 22.

Milo, et al., "Copolymer–1 and Interferon–β Additively Suppress the Immune Response to Myelin Basic Protein by Inhibiting Antigen Presentation", *J. Neuroimmunol.*, 1994, 54, 183 (Abstract).

Nightingale, et al., "Access to Investigational Drugs for Treatment Purposes", *Am. Family Physician*, 1994, 50(4), 845–847.

Schlegel, et al., "Prevention of Graft–Versus–Host Disease by Peptides Binding to Class II Major Histocompatibility Complex Molecules", *Blood*, 1994, 84(8), 2802–2810.

Stark, "Expanded Clinical Trials of Treatment for Multiple Sclerosis (MS): Copolymer 1 (COP–1) Treatment Investigational New Drug (IND) Program", *Ann. Neurol.*, 1994, 36, 114–115.

Teitelbaum, et al., "Immunological Parameters in a Multicenter Clinical Trial of COP1 in Multiple Sclerosis (MS): A 2–year Follow–up", *Neurol.*, 1994, 44(Suppl. 2), A358.

Tisch et al., "Antigen–specific immunotherapy: Is it a Real Possibility to Combat T–Cell–Mediated autoimmunity?" *Proc. Natl. Acad. Sci. U.S.A.*, 1994, 91, 437–438.

Milo, et al., "Additive Effects of Copolymer–1 and Interferon β–1b on the Immune Response to Myelin Basic Protein", *J. Neuroimmunol.*, 1995, 61, 185–193.

O'Connor, et al., "Powders" in *The Science and Practice of Pharmacy*, Remington, 1995, 2, 1598–1614.

Porter, "Coating of Pharmaceutical Dosage Forms," in *The Science and Practice of Pharmacy*, Remington, 1995, 2, 1650–1659.

Reilly, Jr., W.J., "Pharmaceutical Necessities" in *The Science and Practice of Pharmacy*, Remington, 1995, 2, 1380–1416.

Schlegel, et al., "Inhibition of Allorecognition and Prevention of Graft–vs–host Disease (GVHD) by GLAT, a Synthetic Polymer with Promiscuous Binding to Murine and Human MHC Class II Molecules", in *Am. Soc. Hematology, 37th Annual Meeting*, Seattle, WA (USA), Dec. 1–5, 1995, 224a (Abstract).

Ben–Nun, et al., "The Autoimmune Reactivity to Myelin Oligodendrocyte Glycoprotein (MOG) in Multiple Sclerosis is Potentially Pathogenic: Effect of Copolymer 1 on MOG–induced Disease", *J. Neurol.*, 1996, 243(Suppl. 1), S14–S22.

Johnson, Management of Relapsing/Remitting Multiple Sclerosis with Copolymer 1 (Copaxone), *Chemical Abstracts*, 1996, 125, 291993b.

Sykes, "Immunobiology of Transplantation", *Faseb J.*, 1996, 10, 721–730.

Teitelbaum, et al., "Copolymer 1 Inhibits Chronic Relapsing Experimental Allergic Encephalomyelitis Induced by Proteclipid Protein (PLP) Peptides in Mice and Interferes with PLP–specific T Cell Responses", *J. Neuroimmunol.*, 1996, 64, 209–217.

Aharoni, et al., "Studies on the Mechanism and Specificity of the Effect of the Synthetic Random Copolymer GLAT on Graft–versus–Host Disease", *Immunol. Letters*, 1997, 58, 79–87.

Puri et al., "Modulation of the Immune Response in Multiple Sclerosis", *J. Immunol.*, 1997, 158, 2471–2476.

Tarcic et al., "Copolymer 1 (Copaxone) from an Idea to a Drug for Treatment of Multiple Sclerosis" Database HCAPLUS on STN, Israel: An 1997:333270. Kim, Handasa Kim, 1997, 281(14), 16–18 (Abstract).

Teitelbaum, et al., "Copolymer 1 from the Laboratory to FDA", *Israel J. Med. Sci.*, 1997, 33, 280–284.

Fridkis–Hareli, et al., "Promiscuous Binding of Synthetic Copolymer 1 to Purified HLA–DR Molecules", *J. Immunol.*, 1998, 160, 4386–4397.

Fridkis–Hareli, et al., "Synthetic Amino Acid Copolymers that Bind to HLA–DR Proteins and Inhibits Type II Collagen–reactive T Cell Clones", *Proc. Natl. Acad. Sci.*, Oct. 1998, 95, 12528–12531.

Cazzato, et al., "Treatment of Multiple Sclerosis. The Present and the Future. Study Group on Diagnosis and Therapy of Multiple Sclerosis", Database Medline on STN, Instituto do Clinica Neurologica, Università, Trieste, Italy: Medline An: 2000060325, Recent Progressi in Medicina. Oct. 1999, 90(10), 538–544 (Abstract).

Kepsutlu et al., "Evaluation of Chitosan Used as an Excipient in Tablet Formulations", Database HCAPLUS on STN, Department of Pharmaceutical Technology, Gulhane Military Medical Academy, Ankara, 06018, Turkey, HCAPLUS AN: 1999: 590411, Acta. Pol. Pharm. 1999, 56(3), 227–235 (Abstract).

Prat, et al., "Lymphocyte Migration and Multiple Sclerosis: Relation with Disease Course and Therapy", *Ann. Neurol.*, 1999, 46: 253–253.

Fridkis–Hareli et al., "Synthetic Peptides that Inhibit Binding of the Collagen Type II 261–273 Epitope to Rheumatoid Arthritis–Associated HLA–DR1 and DR4 Molecules and Collagen–Specific T–cell Responses", Database HCAPLUS on STN, Department of Clinical Immunology, Aarhus University Hospital, Aarhus, Denmark, HCAPLUS AN: 2000:455053, Human Immunology, 2000, 61(7), 640–650 (Abstracts).

Durelli, "Immunotherapeutics of Multiple Sclerosis", *Instituto di Clinica delle Malattie del Sistema Nervoso Universita di Torino*, 467–475.

U.S. patent application Ser. No. 09/487,793, Eisenbach–Schwartz et al., filed Jan. 20, 2000.

U.S. patent application Ser. No. 09/620,216, Eisenbach–Schwartz et al., filed Jul. 20, 2002.

U.S. patent application Ser. No. 09/765,301, Eisenbach–Schwartz et al., filed Jan. 22, 2001.

U.S. patent application Ser. No. 09/765,644, Eisenbach–Schwartz et al., filed Jan. 22, 2001.

Ju et al., "Idiotypic Analysis Antibodies Against the Terpolymer L–glutamic Acid 60–L–alanine30–L–tyrosine10 (GAT). IV. Induction of CGAT Idiotype Following Immunization with Various Synthetic Polymers Containing Glutamic Acid and Tyrosine", *Eur. J. Immunol.*, 1979, 9(7): 553–560 (Abstract).

Schwartz et al., "Gene Complementation in the T Lymphocyte Proliferative Response to Poly (Glu57Lys38Tyr5): Evidence for Effects of Polymer Handling and Gene Dosage", *J. Immunol.*, 1979, 123(1): 272–278 (Abstract).

Baxevanis et al., "Genetic Control of T–Cell Proliferative Responses to Poly ($Glu^{40}Ala^{60}$) and Poly ($Glu^{51}Lys^{34}Tyr^{15}$): Subregion–Specific Inhibition of the Responses with Monoclonal Ia Antibodies", *Immunogenetics*, 1980, 11: 617–628.

Maurer et al., "Interpretations of Immune Responses of Mice to Poly(Glu60Lys40), its Modified Derivatives, and the Terpolymers Poly(Glu55Lys37Leu8) and Poly (Glu56Lys37Ser7)", *Clin. Immunol. Immunopathol.*, 1980, 15(3): 344–356 (Abstract).

Herzenberg et al., "Lack of Immune Response Gene Control for Induction of Epitope–specific Suppression by TGAL Antigen", *Nature*, 1982, 295: 329–331 (Abstract).

Babu et al., "Reevaluation of Response Patterns of Nonresponder Mice to G1Phe Polymers", *Immunogen.*, 1983, 18(1): 97–100 (Abstract).

Babu et al., "Ir Gene Control of T and B Cell Responses to Determinants in (Glu Lys Ala) Terpolymer", *J. Immunogenet.*, 1984, 11(3–4): 251–254.

Falo et al., "Analysis of Antigen Presentation by Metabolically Inactive Accessory Cells and Their Isolated Membranes", *Proc. Natl. Acad. Sci. USA*, 1985, 82(19): 6647–6651 (Abstract).

Trannoy et al., "Epitope–specific Regulation of the T Cell Repertoire: Carrier Recognition in Association with I–E or I–A Does Not Influence the Restriction of Hapten–Specific T Cells", *Eur. J. Immunol.*, 1985, 15(12): 1215–1221 (Abstract).

Lai et al., "Complementation of Class II a Alleles in the Immune Response to (Glulystyr) Polymers", *Exp. Clin. Immunogenet.*, 1986, 3(1): 38–48 (Abstract).

Lai et al., "Monoclonal T Cell Responses to Two Epitopes on a Single Immunogen Controlled by Two Distinct Genes", *J. Immunol.*, 1986, 136(10): 3799–3804 (Abstract).

De Kruyff et al., "Analysis of T Cell Responses to Poly–L (GluLys) at the Clonal Level. I. Presence of Responsive Clones in Nonresponder Mice", *Eur. J. Immunol.*, 1987, 17 (8): 1115–1120 (Abstract).

Matsunaga et al., "Complementation of Class II A Alleles in the Immune Response to (Glu–Lys–Tyr) Polymers", *Yokohama Med. Bull.*, 1988, 39(1–2): 9–19 (Abstract).

Zisman et al., "Direct Binding of a Synthetic Multichain Polypeptide to Class II Major Histocompatibility Complex Molecules on Antigen–presenting Cells and Stimulation of a Specific T–cell Line Require Processing of the Polypeptide", *Proc. Natl. Acad. Sci. USA*, 1991, 88(21): 9732–9742 (Abstract).

Deeb et al., "Comparison of Freund's and Ribi Adjuvants for Inducing Antibodies to the Synthetic Antigen (TG)–AL in Rabbits", *J. Immunol. Methods*, 1992, 152(1): 105–113 (Abstract).

Kropshofer et al., "Self–Peptides from Four HLA–DR Alleles Share Hydrophobic Anchor Residues Near the $NH_2$–Terminal Including Proline as a Stop Signal for Trimming", *J. Immunol.*, 1993, 151: 4732–4742.

Zisman et al., "Dichotomy Between the T and the B Cell Epitopes of the Synthetic Polypeptide (T,G)–A–L", *Eur. J. Immunol.*, 1994, 24(10): 2497–2505 (Abstract).

Asakura and Rodriguez, "A Unique Population of Circulating Autoantibodies Promotes Central Nervous System Remyelination", *Multiple Sclerosis*, 1998, 4: 217–221.

Asakura et al., "Targeting of IgMk Antibodies to Oligodendrocytes Promotes CNS Remyelination", *J. Neurosci.*, 1998, 18(19): 7700–7708.

Li et al., "Glatiramer Acetate Blocks the Activation of THP–1 Cells by Interferon–γ", *Eur. J. Pharmacol.*, 1998, 342: 303–310.

Pavelko et al., "Acceleration in the Rate of CNS Remyelination in Lysolecithin–Induced Demyelination", *J. Neurosci.*, 1998, 18(7): 2498–2505.

Rodriguez, *Neurological Therapeutics*, 1998, 15(3): 245–250.

Cohen, "Fundamental Immunology", *Systemic Autoimmunity*, 4th Ed., 1999, 1083.

Fridkis–Hareli et al., "Binding of Random Copolymers of Three Amino Acids to Class II MHC Molecules", *Intl. Immunol.*, 1999, 11(5): 635–641.

McGavern et al., "Do Antibodies Stimulate Myelin Repair in Multiple Sclerosis", *The Neuroscientist*, 1999, 5(1): 19–28.

Bieber et al., "Antibody–Mediated Remyelination: Relevance to Multiple Sclerosis", *Multiple Sclerosis*, 2000, 6: S1–S5.

Henry, Celia M., "Special Delivery", *Chem. and Eng. News*, Sep. 18, 2000, 49–54.

Warrington et al., "Human Monoclonal Antibodies Reactive to oligodendrocytes Promote Remyelination in a Model of Multiple Sclerosis", *Neurobiology*, 2000, 97(12): 6820–6825.

Bieber et al., "Humoral Autoimmunity as a Mediator of CNS Repair", *Trends in Neurosci.*, 2001, 24(11): S39–S44.

Warrington et al., "Immunoglobulin–Mediated CNS Repair", *J. Allergy Clin. Immunol.*, 2001, S121–S125.

FIGURE 20E
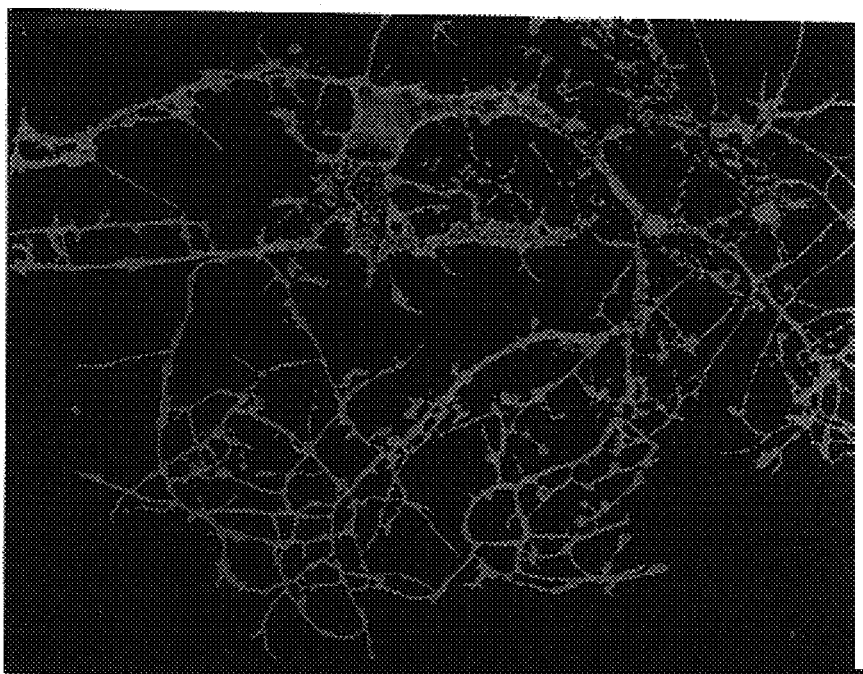
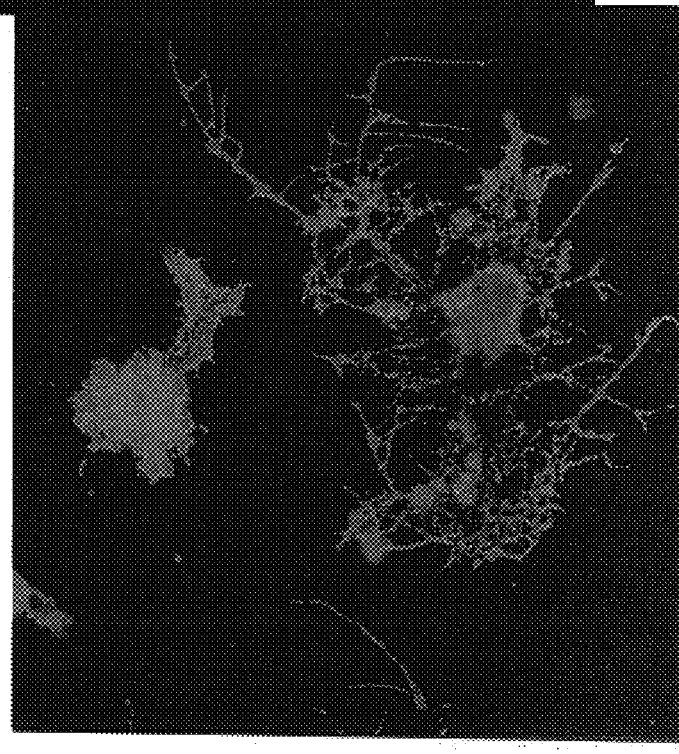
FIGURE 20F

FIGURE 23A
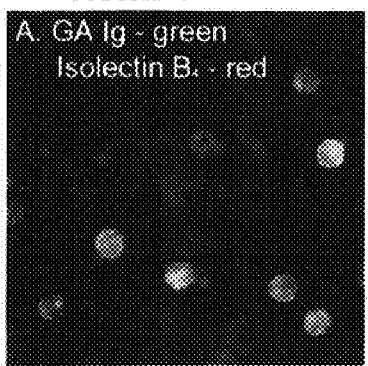
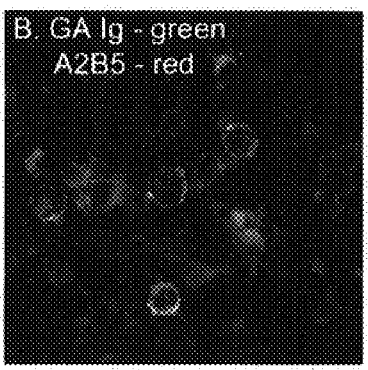
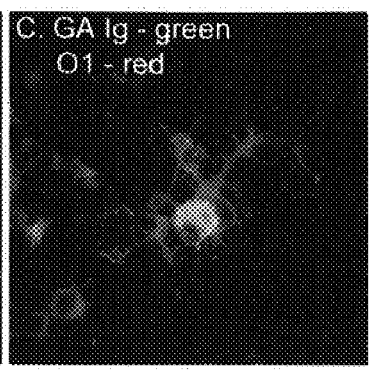
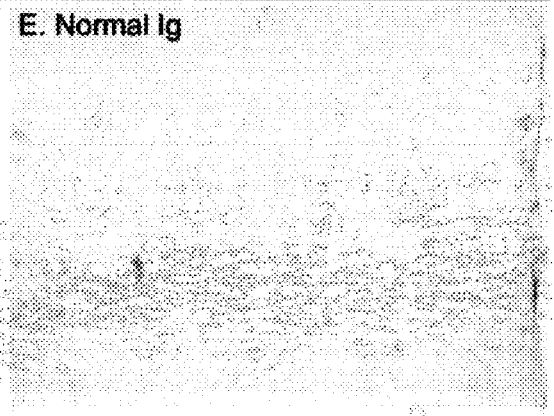
FIGURE 23A
FIGURE 23B Isolation of Cop-1 Ig

TREATMENT OF CENTRAL NERVOUS SYSTEM DISEASES BY ANTIBODIES AGAINST GLATIRAMER ACETATE

This application claims the benefit of U.S. Provisional No. 60/287,171, filed Apr. 27, 2001, U.S. Provisional No. 60/269,788, filed Feb. 16, 2001, and U.S. Provisional No. 60/212,577, filed Jun. 20, 2000, the contents of which are hereby incorporated by reference into the present application.

Throughout this application, various references are referenced by arabic numbers within parenthesis. Full citations for these references may be found at the end of the specification, immediately preceding the claims. These references, in their entireties, are hereby incorporated by reference to more fully describe the state of the art to which this invention pertains.

FIELD OF THE INVENTION

The present invention is directed to the treatment of central nervous system (CNS) diseases by antibodies.

BACKGROUND OF THE INVENTION

The nervous system of vertebrates is divided into the central nervous system, comprised of the brain and spinal cord, and the peripheral nervous system, consisting of the outlying nerves (16). The axons of most nerve cells are covered with a myelin sheath, a stack of specialized plasma membranes. Glial cells that wrap around the axons produce the myelin sheath. In the CNS, these cells are called oligodendrocytes. The myelin membranes of the CNS contain myelin basic protein (MBP) and a proteolipid (PLP) that is not found elsewhere in vertebrates. Each region of myelin formed by an individual glial cell is separated from the next region by an unmyelinated area called the node of Ranvier; only at nodes is the axonal membrane in direct contact with the extracellular fluid.

The myelin sheath, which can be 10–12 myelin wraps thick, acts as an electric insulator of the axon by preventing the transfer of ions between the axonal cytoplasm and the extracellular fluids (16). Thus all electric activity in axons is confined to the nodes of Ranvier, the sites where ions can flow across the axonal membrane. Node regions contain a high density of voltage-dependent Na+ channels, about 10,000 per $\mu m^2$, whereas the regions of axonal membrane between the nodes have few if any channels.

The excess cytosolic positive ions generated at a node during the membrane depolarization associated with an action potential diffuse through the axonal cytoplasm to the next node with very little loss or attenuation because ions are capable of moving across the axonal membrane only at the myelin-free nodes (16). Thus a depolarization at one node spreads rapidly to the next node, and the action potential jumps from node to node. For this reason, the conduction velocity of myelinated nerves is much greater than that of unmyelinated nerves of the same diameter. For example, a 12-$\mu$m-diameter myelinated vertebrate axon and a 600-$\mu$m-diameter unmyelinated squid axon both conduct impulses at 12 m/s.

One of the more common neurologic diseases in human adults is multiple sclerosis. This condition is a chronic, frequently progressive, inflammatory CNS disease characterized pathologically by primary demyelination. The etiology and pathogenesis of multiple sclerosis are unknown. Researchers have hypothesized that multiple sclerosis is an autoimmune disease (14, 23, 47) or that a virus, bacteria or other agent, precipitates an inflammatory response in the CNS, which leads to either direct or indirect ("bystander") myelin destruction, potentially with an induced autoimmune component (31, 38). Thus, a rebuilding of the myelin sheath, or remyelination, can treat multiple sclerosis.

Spontaneous remyelination of axons within lesions by oligodendrocytes has been shown to occur to a small degree in SJL/J mice and multiple sclerosis patients (1). Several types of antibodies have been found to promote remyelination (1). Some of these antibodies are polyclonal, derived by immunization with spinal cord homogenate or myelin basic protein (71). One remyelination-promoting antibody is monoclonal (SCH 94.03) (1). The isotype of these antibodies is IgM, and they share the characteristic of binding to the surface of oligodendrocytes (1). Also, they are polyreactive, binding to a variety of cytoskeletal proteins or proteins with repeating structures (1).

Of clinical importance is the question whether morphologic regeneration of thin myelin sheaths contributes to functional recovery (1). Computer simulations indicate that new myelin formation even by inappropriately thin sheaths improves impulse conduction (1). Since the axon membrane of normally myelinated fibers is highly differentiated, it is necessary for sodium channels to be present at high density at the node of Ranvier to propagate saltatory conduction. Experimental evidence suggests that newly formed nodes do develop the required high sodium channel density as demonstrated by saxitoxin binding. Data suggest that remyelination even by inappropriately thin myelin improves conduction in a previously demyelinated axon. Therefore, any strategy to promote this morphologic phenomenon has the potential of producing functional recovery. Studies examining biopsy tissues from patients with severe acute exacerbations demonstrate that demyelination is a significant component of the acute multiple sclerosis lesion (57). Therefore, remissions are probably associated with significant CNS remyelination (1).

One commonly utilized experimental model of multiple sclerosis is induced by Theiler's murine encephalomyelitis virus (TMEV) (15, 59). In the TMEV model, spinal cord demyelination is influenced by the immune response to virus infection and is therefore continuously sensitive to immunomodulation. Previous experiments in Strain Jackson Laboratories (SJL) mice infected with TMEV showed that 4 to 5% of the demyelinated area exhibited significant spontaneous remyelination (62). In protocols using antibody therapy and monoclonal antibody therapy, this number increased up to 30–35% (41, 58, 71). For instance, using the TMEV model, it was demonstrated that the passive transfer of CNS specific antiserum (63) and purified antibodies (55, 62, 71) directed against myelin components promoted CNS remyelination. This contrasts with the conventional view that the humoral immune response plays a pathogenic role in CNS demyelination (56). Researchers also generated a monoclonal antibody that reacted against a surface component of oligodendrocytes and promoted remyelination (40–42). It has also been shown that antibodies reactive with myelin basic protein (MBP) promoted CNS remyelination (58). In these experiments, infected SJL mice were treated with the whole anti-serum or affinity purified mouse antibodies directed against rabbit or rat myelin basic proteins. There was extensive evidence for new myelin synthesis as measured by quantitative morphometry. Electron microscopy revealed numerous oligodendrocytes and remyelinated CNS axons with a relative lack of inflammatory cells. Viral antigen persisted in these animals despite enhanced CNS remyelination. These findings indicated for the first time that antibodies reactive against a myelin autoantigen and in particular, MBP, have the potential for myelin repair.

U.S. Pat. No. 5,591,629 describes the promotion of CNS remyelination in the TMEV model through SCH 94.03 monoclonal antibodies directed against spinal cord homogenate (SCH) (1). SCH encompasses myelin antigens, such as MBP (64) and proteolipid protein (PLP) (12, 67). Although SCH contains MBP, this antibody does not react with MBP. The SCH 94.03 antibody is an IgM which recognizes cytoplasmic determinants on glial cells. It also recognizes surface determinants on glial cells, including oligodendrocytes. Experiments demonstrated that the antibody does not react with TMEV. In addition, the antibody was shown to promote the proliferation of glial cells in mixed rat brain culture in a dose-dependent manner. SCH 94.03 is a natural autoantibody.

A treatment that has been shown to be effective in reducing exacerbations of multiple sclerosis is the administration of glatiramer acetate (2–6, 31). Daily subcutaneous injections of glatiramer acetate (20 mg/injection) reduce relapse rates, appearance of new lesions by magnetic resonance imaging (MRI), and progression of disability (26). COPAXONE® is the brand name for glatiramer acetate (also known as Copolymer-1 (77), Copolymer 1, Cop-1 or Cop), an FDA-approved drug for the treatment of multiple sclerosis. Glatiramer acetate, the active ingredient of COPAXONE®, consists of the acetate salts of synthetic polypeptides, containing four naturally occurring amino acids: L-glutamic acid, L-alanine, L-tyrosine, and L-lysine (77) with an average molar fraction of L-glutamic acid: 0.129–0.153; L-alanine: 0.392–0.462; L-tyrosine: 0.086–0.100; L-lysine: 0.300–0.376, respectively. The average molecular weight of glatiramer acetate is 4,700–11,000 daltons (77). Chemically, glatiramer acetate is designated L-glutamic acid polymer with L-alanine, L-lysine and L-tyrosine, acetate (salt) (77). Its structural formula is:

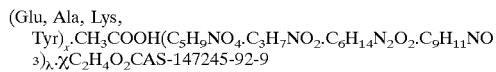

(77). Glatiramer acetate is also written as: poly[L-Glu$^{13-15}$, L-Ala$^{39-46}$, L-Tyr$^{8.6-10}$, L-Lys$^{30-37}$]nCH$_3$COOH.

Unlike myelin basic protein (MBP), with which it shares some structural characteristics, glatiramer acetate inhibits rather than induces experimental autoimmune encephalomyelitis (EAE), an animal model of MS (37, 65–66). Glatiramer acetate-reactive, type 2 helper T lymphocytes confer resistance to EAE.

In spite of the experimental evidence that glatiramer acetate down-regulates certain immune functions, clinical use of glatiramer acetate indicates that other immune functions are stimulated by the peptide treatment. In rodents, monoclonal antibodies to glatiramer acetate have been generated, some of which cross-react with MBP (68), but other cross-reactivities are unknown. The humoral response to glatiramer acetate may have diverse roles in multiple sclerosis. Some autoreactive antibodies to myelin antigens might contribute to pathogenesis (22, 35). Other antibodies, such as those that develop in a subset of interferon-treated patients, may neutralize therapeutic efficacy. A third possibility is that some antibodies may in fact be protective. All individuals have antibodies to a wide range of endogenous antigens, including MBP, suggesting that natural autoantibodies represent a conserved adaptation to nervous system disease and trauma. In support of a protective role for autoreactive antibodies, mouse or human antibodies reactive to the central nervous system (CNS) have been found to promote myelin repair in viral experimental model of multiple sclerosis (41, 48, 53, 58). Antibodies have been found to stimulate remyelination in SJL mice that were chronically infected with EAE (41, 58).

Antisera against glatiramer acetate have been employed to investigate the mechanism by which L-glatiramer acetate is effective against Experimental Allergic Encephalomyelitis (EAE) (74–75). For this purpose, Webb et al. measured the cross-reactivity of L-glatiramer acetate anti-sera with D-glatiramer acetate and Copolymer 4 (L-glatiramer acetate modified by the replacement of tyrosine with tryptophan) (75). Webb et al. carried out a similar experiment to determine the reactivity of L-glatiramer acetate anti-sera with L-glatiramer acetate, and the cross-reactivity of L-glatiramer acetate anti-sera with AGT (alanine, glutamic acid and tyrosine), BE (Basic Encephalitogen), AAspLT (alanine, aspartic acid, lysine and tyrosine) and AGL (alanine, glutamic acid and lysine) (74).

Monoclonal antibodies against glatiramer acetate and against MBP have also been utilized to probe the mechanism of glatiramer acetate in treatment of EAE (68). The cross-reactivity of monoclonal antibodies against glatiramer acetate with MBP was analyzed by Teitelbaum et al (68). They also determined the cross-reactivity of monoclonal antibodies against MBP with glatiramer acetate (68). Another focus of their experiments was the cross-reactivity of glatiramer acetate anti-sera with MBP and of MBP-antisera with glatiramer acetate (68). The cross-reactivity of anti-MBP anti-sera with glatiramer acetate was additionally investigated by Lisak et al (37).

SUMMARY OF THE INVENTION

The subject invention concerns a humanized antibody directed against an epitope on glatiramer acetate, also known as Copolymer 1, Copolymer-1, Cop-1 or Cop.

The subject invention further encompasses a F$_{ab}$ fragment that binds to an epitope on glatiramer acetate.

In addition, the subject invention relates to a pharmaceutical composition comprising an antibody directed against an epitope on glatiramer acetate in an amount effective to treat a central nervous system disease and a pharmaceutically acceptable carrier.

The subject invention also provides a method of stimulating remyelination of central nervous system axons comprising contacting the axons with an antibody directed against an epitope on glatiramer acetate in an amount effective to stimulate remyelination of central nervous system axons.

The subject invention additionally includes a method of treating a subject suffering from a disease associated with demyelination of central nervous system axons comprising administering to the subject an effective amount of an antibody directed against an epitope on glatiramer acetate in an amount effective to treat the disease associated with demyelination of central nervous system axons.

The subject invention further relates to a method of stimulating remyelination of central nervous system axons comprising contacting the axons with glatiramer acetate in an amount effective to stimulate remyelination of central nervous system axons.

The subject invention also concerns a method of treating a subject suffering from a disease associated with demyelination of central nervous system axons comprising administering to the subject glatiramer acetate in an amount effective to treat the disease associated with demyelination of central nervous system axons, wherein the disease associated with demyelination of central nervous system axons is selected from the group consisting of: acute disseminated encephalomyelitis, transverse myelitis, demyelinating genetic diseases, spinal cord injury, virus-induced demyelination, Progressive Multifocal Leucoencephalopathy, Human Lymphotrophic T-cell Virus I (HTLVI)-associated myelopathy, and nutritional metabolic disorders.

Finally, the subject invention encompasses a method of stimulating proliferation of lymphocytes comprising contacting the lymphocytes with an antibody directed against an epitope on glatiramer acetate in an amount effective to stimulate lymphocyte proliferation.

DESCRIPTION OF THE DRAWINGS

FIGS. 20-A–20-D show the staining of antibodies against glatiramer acetate, while FIGS. 20E–20-F reflect the staining of O4-positive oligodendrocytes.

FIG. 23 shows CNS reactivity of purified glatiramer acetate Ig. (a, b, c) In rat CNS glial cultures glatiramer acetate IgG bound to the surface of round, non-process-bearing cells located on the upper surface of the cultures. Glatiramer acetate IgG-positive cells co-labeled with the microglial marker, Bandeiraea simplicifolia isolectin $B_4$, but did not co-label with oligodendrocyte markers, A2B5 (immature oligodendrocytes) or O1 (mature oligodendrocytes). (d, e) In spinal cord sections from lesioned spinal cord, biotinylated glatiramer acetate IgG bound in the white matter to glial cells, especially their processes, and to the perivascular infiltrate, but not to myelin or oligodendrocytes. Gray matter and neuronal cell bodies were also glatiramer acetate IgG-positive. Biotinylated pooled mouse IgG did not bind appreciably to sections.

DETAILED DESCRIPTION OF THE INVENTION

Figure 1:
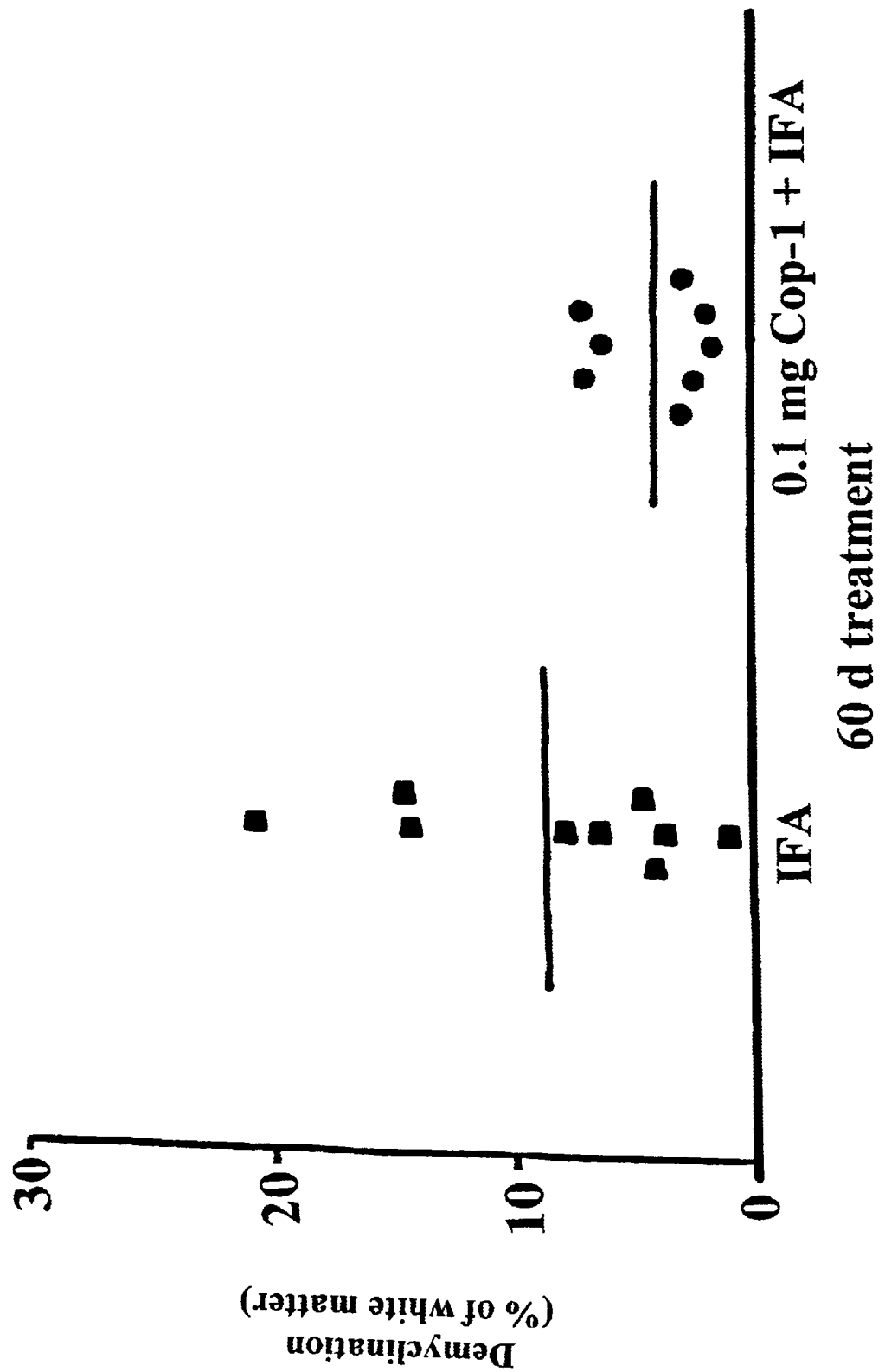
FIG. 1 demonstrates that glatiramer acetate does not alter the extent of spinal cord demyelinating lesions during early disease. Each dot represents one mouse.

The phrase, early disease, is defined as the period up to 45 days post-infection and encompasses the encephalitic stage of disease as well as the beginning of the demyelinating phase of disease (begins at approximately Day 21 post-infection).

The phrase, late disease, is defined as the period beyond four months of infection.

The phrase, low-dose glatiramer acetate, is defined as single or multiple injections of glatiramer acetate at 0.02–0.1 mg/injection. Given the average weight of adult SJL/J mice of 20 g, a 0.1 mg injection is equivalent to 5 mg/kg.

The phrase, high-dose glatiramer acetate, is defined as single or multiple injections of glatiramer acetate at 5 mg/injection. Given the average weight of adult SJL/J mice of 20 g, a 5 mg injection is equivalent to 250 mg/kg.

The subject invention provides a humanized antibody directed against an epitope on glatiramer acetate.

In one embodiment, this humanized antibody is not cross-reactive with MBP.

In another embodiment, this humanized antibody consists essentially of IgG1.

In a further embodiment, this humanized antibody does not react with mature oligodendrocytes.

In another embodiment, this humanized antibody cross-reacts with SCH.

In one embodiment, this humanized antibody primarily reacts with cells exhibiting a macrophage or microglial phenotype.

In yet another embodiment, this humanized antibody is a monoclonal antibody.

In a further embodiment, this humanized antibody is a polyclonal antibody.

The subject invention further relates to a $F_{ab}$ fragment that binds to an epitope on glatiramer acetate.

In addition, the subject invention involves a pharmaceutical composition comprising an antibody directed against an epitope on glatiramer acetate in an amount effective to treat a demyelinating central nervous system disease and a pharmaceutically acceptable carrier.

In the pharmaceutical composition, this antibody may be a humanized antibody.

In the pharmaceutical composition, this antibody may be not cross-reactive with MBP.

In the pharmaceutical composition, this antibody may consist essentially of IgG1.

In the pharmaceutical composition, this antibody may not react with mature oligodendrocytes.

In the pharmaceutical composition, this antibody may cross-react with SCH.

In the pharmaceutical composition, this antibody may primarily react with cells exhibiting a macrophage or microglial phenotype.

In the pharmaceutical composition, this antibody may be a monoclonal antibody.

In the pharmaceutical composition, this antibody may be a polyclonal antibody.

The subject invention also provides a method of stimulating remyelination of central nervous system axons comprising contacting the axons with an antibody directed against an epitope on glatiramer acetate in an amount effective to stimulate remyelination of central nervous system axons.

In this method, the antibody may be a humanized antibody.

In this method, the antibody may be not cross-reactive with MBP.

In this method, the antibody may consist essentially of IgG1.

In this method, the antibody may not react with mature oligodendrocytes.

In this method, the antibody may cross-react with SCH.

In this method, the antibody may primarily react with cells exhibiting a macrophage or microglial phenotype.

In this method, the antibody may be a monoclonal antibody.

In this method, the antibody may be a polyclonal antibody.

Additionally, the subject invention concerns a method of treating a subject suffering from a disease associated with demyelination of central nervous system axons comprising administering to the subject an effective amount of an antibody directed against an epitope on glatiramer acetate in an amount effective to treat the disease associated with demyelination of central nervous system axons.

In this method, the antibody may be a humanized antibody directed against an epitope on glatiramer acetate.

In this method, the antibody may not be cross-reactive with MBP.

In this method, the antibody may consist essentially of IgG1.

In this method, the antibody may not react with mature oligodendrocytes.

In this method, the antibody may cross-reacts with SCH.

In this method, the antibody may primarily react with cells exhibiting a macrophage or microglial phenotype.

In this method, the antibody may be a monoclonal antibody.

In this method, the antibody may be a polyclonal antibody.

In this method, the disease associated with demyelination of central nervous system axons is selected from the group consisting of: multiple sclerosis, acute disseminated encephalomyelitis, transverse myelitis, demyelinating genetic diseases, spinal cord injury, virus-induced demyelination, Progressive Multifocal Leucoencephalopathy, Human Lymphotrophic T-cell Virus I (HTLVI)-associated myelopathy, and nutritional metabolic disorders.

In one embodiment, the disease associated with demyelination of central nervous system axons is multiple sclerosis.

In another embodiment, the disease associated with demyelination of central nervous system axons is acute disseminated encephalomyelitis.

In an additional embodiment, the disease associated with demyelination of central nervous system axons is transverse myelitis.

In a further embodiment, the disease associated with demyelination of central nervous system axons is a demyelinating genetic disease.

In yet another embodiment, the disease associated with demyelination of central nervous system axons is a spinal cord injury.

In a further embodiment, the disease associated with demyelination of central nervous system axons is virus-induced demyelination.

In another embodiment, the disease associated with demyelination of central nervous system axons is Progressive Multifocal Leucoencephalopathy.

In an additional embodiment, the disease associated with demyelination of central nervous system axons is HTLVI-associated myelopathy.

In another embodiment, the disease associated with demyelination of central nervous system axons is a nutritional metabolic disorder.

In one embodiment, the nutritional metabolic disorder is vitamin $B_{12}$ deficiency.

In another embodiment, the nutritional metabolic disorder is central pontine myelinolysis.

In one embodiment, the effective amount is an amount from 0.1 mg to 400 mg.

In a preferred embodiment, the effective amount is an amount from 0.1 mg to 250 mg.

In a further embodiment, the effective amount is an amount from 0.5 mg to 400 mg.

In another embodiment, the effective amount is an amount from 0.5 mg to 300 mg.

In another embodiment, the effective amount is an amount from 0.5 mg to 250 mg.

In further embodiment, the effective amount is an amount from 1.0 mg to 250 mg.

In another embodiment, the effective amount is an amount from 2.5 mg to 225 mg.

In yet another embodiment, the effective amount is an amount from 5.0 mg to 200 mg.

In a further embodiment, the effective amount is an amount from 10 mg to 175 mg.

In another embodiment, the effective amount is an amount from 25 mg to 150 mg.

In yet another embodiment, the dosage of antibodies against glatiramer acetate is an amount from 50 mg to 125 mg.

In a further embodiment, the effective amount is an amount from 75 mg to 100 mg.

The subject invention further provides a method of stimulating remyelination of central nervous system axons comprising contacting the axons with glatiramer acetate in an amount effective to stimulate remyelination of central nervous system axons.

The subject invention additionally concerns a method of treating a subject suffering from a disease associated with demyelination of central nervous system axons comprising administering to the subject glatiramer acetate in an amount effective to treat the disease associated with demyelination of central nervous system axons, wherein the disease associated with demyelination of central nervous system axons is selected from the group consisting of: acute disseminated encephalomyelitis, transverse myelitis, demyelinating genetic diseases, spinal cord injury, virus-induced demyelination, Progressive Multifocal Leucoencephalopathy, HTLVI-associated myelopathy, and nutritional metabolic disorders.

The subject invention also contains a method of stimulating proliferation of lymphocytes comprising contacting the lymphocytes with an antibody directed against an epitope on glatiramer acetate in an amount effective to stimulate lymphocyte proliferation.

In this method, the antibody may be a humanized antibody directed against an epitope on glatiramer acetate.

In this method, the antibody may be not cross-reactive with MBP.

In this method, the antibody may consist essentially of IgG1.

In this method, the antibody may not react with mature oligodendrocytes.

In this method, the antibody may cross-react with SCH.

In this method, the antibody may primarily react with cells exhibiting a macrophage or microglial phenotype.

In this method, the antibody may be a monoclonal antibody.

In this method, the antibody may be a humanized polyclonal antibody directed against an epitope on glatiramer acetate.

In one embodiment, antibodies against glatiramer acetate are generated by intraperitoneal injection of glatiramer acetate into SJL mice. Alternatively, glatiramer acetate could be injected intradermally or intravenously. Other sources of antibodies against glatiramer acetate are contemplated by the invention. These sources include, but are not limited to, other mice, rabbits, cats, goats, monkeys and humans.

Additionally contemplated by the present invention is a monoclonal antibody directed against an epitope on glatiramer acetate. These antibodies can be created by procedures known to those of skill in the art. Such procedures include, but are not limited to, the creation of hybridomas and antibody libraries.

A hybridoma is produced by the fusion of Normal B lymphocytes, which will not grow indefinitely in culture, and myeloma cells, which are immortal (16, 78). The selective medium most often used to culture such fused cells is called HAT medium, because it contains hypoxanthine, aminopterin, and thymidine (16). Normal B lymphocytes can grow in HAT medium, salvage mutants cannot, but their hybrids with Normal B lymphocytes can (16). Mutant myeloma cell lines that have lost the salvage pathways for purines (indicated by their inability to grow in HAT medium) are selected (16). These myeloma cells are then fused with normal B lymphocytes, creating hybridoma cells (16). Like myeloma cells, hybridoma cells can grow indefinitely in culture; like normal B lymphocytes, the fused cells have purine salvage-pathway enzymes and can grow in HAT medium (16). If a mixture of fused and unfused cells is placed in HAT medium, the unfused mutant myeloma cells and the unfused lymphocytes die, leaving a culture of immortal hybridoma cells, each of which produces a monoclonal antibody (16). Clones of hybridoma cells can be tested separately for the production of a desired antibody and the clones containing that antibody then can be cultured in large amounts (16).

Following the cloning of genes encoding antibodies, a library of filamentous phage can be prepared (52). Each phage has the potential to display a unique antibody on its surface, which is the selectable phenotype (52). Within the phage coat is the genotype that encodes the displayed molecule. This linkage of displayed antibody phenotype with encapsulated genotype via the phage surface forms the basis of the technique (52). Typically, the antibody fragments are displayed on the surface of phage as either $F_{ab}$ fragments, single-chain variable region fragments ($scF_{vs}$), or dimeric $scF_{vs}$, also known as diabodies, which differ from $scF_{vs}$ in the reduced length of the linker peptide used and their preference to associate as dimers (52). Library construction is facilitated by the ready availability of phagemid vectors, which allow for construction and display of libraries of these antibody fragments using a single rare cutting restriction enzyme, SfiI (52). Selection of antibodies from the library is based on the displayed antibodies' binding specificity and affinity and is generally performed over several rounds of selection and amplification in a process known as panning (52).

Phage displayed antibody libraries can be screened by panning on purified antigens immobilized on artificial surfaces or by panning on cell surface expressed antigens (52). In contrast to panning on purified immobilized antigen, cell panning selects for antibodies that are more likely to bind to epitopes in vivo (52).

One method of improving the specificity of antibodies in an library is saturated mutagenesis of complementarity determining regions (CDR) (CDR walking mutagenesis) (52). In this approach, saturation mutagenesis of a CDR is constrained to libraries that examine all possible amino acids in the target CDR (52). Two strategies are employed—either sequential or parallel optimization of CDR (52). In the sequential approach, the library of antibodies with a single randomized CDR is screened by several rounds of panning against the antigen (52). The selected clone(s) are then used in the construction of a second library where a different single CDR is randomized (52). The panning, selection of clone(s) and construction of a library is repeated several times (52). Sequential optimization takes into account that optimal binding may result from the interdependence of CDRs (52). In the parallel approach, independent libraries are constructed where each library represents the randomization of given CDR (52). Each library is screened by several rounds of panning against the antigen (52). Then, the individually optimized CDRs are combined. If the free energy change of individually optimized CDRs combined is nearly equal to the sum of the free energy changes in the single optimized CDRs, the free energy changes are said to be additive (52). As additivity within the antibody binding site it virtually impossible to predict, Rader and Barbas believe that sequential CDR optimization is preferred over parallel (52).

The subject invention further contemplates humanized antibodies against glatiramer acetate. A humanized antibody is a non-human antibody which has been genetically engineered by the substitution of human nucleotide sequences in the nonvariable regions of the non-human antibodies (1, 72). Such substitutions reduce the immunogenicity of the antibodies in humans without significantly lowering the specificity of the antibodies.

One type of humanized antibody is a chimera, in which the variable region genes of a non-human antibody are cloned into a human expression vector containing the appropriate human light chain and heavy chain constant region genes (72). The resulting chimeric monoclonal antibody should have the antigen-binding capacity (from the variable region of the non-human source) and should be significantly less immunogenic than the unaltered non-human monoclonal antibody.

Jones and his colleagues further humanized chimeric antibodies through a technique known as complementarity determining region (CDR) grafting (72). In this process, the antigen binding sites, which are formed by three CDRs of the heavy chain and three CDRs of the light chain, are excised from cells secreting non-human monoclonal antibodies and grafted into the DNA coding for the framework of the human antibody (72). Since only the antigen-binding site CDRs of the non-human antibody are transplanted, the resulting humanized antibody is less immunogenic than a chimeric antibody in which the entire variable domain is transplanted.

This process has been further improved by reshaping, hyperchimerization, and veneering (72). In the reshaping process on the basis of homology, the non-human variable region is compared with the consensus sequence of the protein sequence subgroup to which it belongs (72). Similarly, the selected human constant region accepting framework is compared with its family consensus sequence (72). The sequence analyses identify residues which may have undergone mutation during the affinity maturation procedure and may therefore be idiosyncratic (72). Inclusion of the more common human residues minimizes immunogenicity problems by replacing human acceptor idiosyncratic resides.

Hyperchimerization is an alternative method of identifying residues outside of the CDR regions that are likely to be involved in the reconstitution of binding activity (72). In this method, the human sequences are compared with non-human variable region sequences and the one with highest homology is selected as the acceptor framework (72). As in the reshaping procedure, the idiosyncratic residues are replaced by the more commonly occurring human residues (72). The non-CDR residues that may be interacting with the CDR sequences are identified (72). Finally, one of these residues is selected to be included in the variable region framework (72).

Veneering is the process of replacing the displayed surfaces of proteins, or residues, which differ from those commonly found in human antibodies (72). Appropriate replacement of the outer residues may have little or no impact on the inner domains or interdomain framework (72). In the process of veneering, the most homologous human variable regions are selected and compared by each residue to the corresponding non-human variable regions (72). Then, the non-human framework residues, which differ from the human homologue, are replaced by the residues present in the human homologue (72).

The subject antibodies against glatiramer acetate can be administered by any method known to those of skill in the art. Such methods include, but are not limited to, intravenous, subcutaneous, intramuscular and intraperitoneal injection, and oral, nasal and rectal administration of the active substance and a pharmaceutically acceptable carrier.

In addition to in vivo methods of promoting remyelination, ex vivo methods of stimulating remyelination in CNS axons are encompassed by the present invention. For example, antibodies against glatiramer acetate may be used in vitro to stimulate the proliferation and/or differentiation of glial cells, such as oligodendrocytes. These exogenous glial cells can then be introduced into the CNS using known techniques. Remyelination of CNS axons would be increased by raising the number of endogenous glial cells, as these cells play a critical role in the production of myelin.

In vitro methods of producing glial cells, or stimulating the proliferation of glial cells from mixed culture are also encompassed by the subject invention. For example, cells obtained from rat optic nerve, or rat brain, containing glial cells, are cultured as a mixed culture under conditions sufficient to promote growth of the cells. An effective amount of antibodies against glatiramer acetate is then added to the mixed culture and maintained under conditions sufficient for growth and proliferation of cells. The antibodies against glatiramer acetate stimulate the proliferation of glial cells in the mixed culture. Thus, the proliferation of glial cells cultured in the presence of antibodies against glatiramer acetate is increased, relative to the proliferation of glial cells grown in the absence of the antibodies.

The subject invention concerns treatment of a demyelinating central nervous system disease by a treatment regime that promotes production of a level of antibodies against glatiramer acetate or polyclonal B cell expansion that results in CNS remyelination.

In one embodiment, the treatment regime entails the administration of glatiramer acetate. Regime variables could include, but not be limited to, dose, frequency of administration, sites of administration, and adjuvant co-administration. The appropriate regimen of treatment with glatiramer acetate should be determined empirically from patient studies.

Glatiramer acetate and antibodies against glatiramer acetate can be formulated into pharmaceutical compositions containing a pharmaceutically acceptable carrier. As used herein, pharmaceutically acceptable carrier includes any and all solvents, dispersion media, adjuvants, coatings, antibacterial and antifungal agents, isotonic and absorption delaying agents, sweeteners and the like. The pharmaceutically acceptable carriers may be prepared from a wide range of materials including, but not limited to, flavoring agents, sweetening agents and miscellaneous materials such as buffers and absorbents that may be needed in order to prepare a particular therapeutic composition. The use of such media and agents with pharmaceutically active substances is well known in the art. Except insofar as any conventional media or agent is incompatible with the active ingredient, its use in the therapeutic compositions is contemplated.

Glatiramer acetate and antibodies against glatiramer acetate can be formulated into any form known in the art using procedures available to one of skill in the art. In one embodiment, glatiramer acetate or an antibody against glatiramer acetate is introduced into the body by way of ingestion or inhalation. For example, they may be administered by way of the mouth through feeding, through a stomach tube, by inhalation into the bronchial passages or by nasal inhalation. The composition contemplated by the subject invention may be administered either as a simple oral solution, as an emulsion or suspension formulation, as a solid oral dosage form (capsule or tablet), or even as a soft gelatin capsule. The present invention contemplates immediate release dosage forms and modified release dosage forms (including particulates, coated granules and pellets, emulsions, microemulsions and encapsulation in microspheres and nanospheres).

In one embodiment, the composition is formulated into a capsule or tablet using techniques available to one of skill in the art.

In another embodiment, glatiramer acetate or an antibody against glatiramer acetate is administered in another convenient form, such as an injectable solution or suspension, a spray solution or suspension, a rectal suppository, a lotion, a gum, a lozenge, a food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, the present compositions can be formulated into cereals, snack items such as chips, bars, gum drops, chewable candies or slowly dissolving lozenges.

For both glatiramer acetate and antibodies against glatiramer acetate, one of skill in the art can readily substitute structurally-related amino acids without deviating from the spirit of the invention. The present invention includes polypeptides and peptides which contain amino acids that are structurally related to tyrosine, glutamic acid, alanine or lysine and possess the ability to stimulate the production of polyclonal antibodies against them. Such substitutions retain substantially equivalent biological activity in their ability to suppress or alleviate the symptoms of the CNS disease. These substitutions are structurally-related amino acid substitutions, including those amino acids which have about the same charge, hydrophobicity and size as tyrosine, glutamic acid, alanine or lysine. For example lysine is structurally-related to arginine and histidine; glutamic acid is structurally-related to aspartic acid; tyrosine is structurally-related to serine, threonine, phenylalanine and tryptophan; and alanine is structurally-related to valine, leucine and isoleucine. These and other conservative substitutions, such as structurally-related synthetic amino acids, are contemplated by the present invention.

Moreover, glatiramer acetate can be composed of 1-or d-amino acids. As is known by one of skill in the art, l-amino acids occur in most natural proteins. However, d-amino acids are commercially available and can be substituted for some or all of the amino acids used to make glatiramer acetate. The present invention contemplates glatiramer acetate consisting essentially of l-amino acids, as well as glatiramer acetate consisting essentially of d-amino acids.

EXPERIMENTAL DETAILS

Experimental Methods

Mice and Viral Infection

All mice used in the experiments were SJL/J mice (Jackson Laboratories, Bar Harbor, Me.). Six- to eight-week-old mice were intracerebrally injected with $2.0 \times 10^6$ pfu of Daniel's strain of Theiler's murine encephalomyelitis virus.

Virus

The Daniel's strain of Theiler's murine encephalomyelitis virus (TMEV) was used in all experiments. The original virus stock was obtained from J. Lehrich and B. Arnason after eight passages in cultured baby hamster kidney (BHK) cells (33). The virus was passaged an additional six times at a multiplicity of infection of 0.1 plaque-forming units per cell. Cell-associated virus was released by freeze-thawing and sonication. The lysate was clarified by centrifugation and stored in aliquots at $-70°$ C.

Glatiramer Acetate Injections

All injections of glatiramer acetate, alone or in IFA, were given subcutaneously in the flank or neck. Glatiramer acetate was administered in an emulsion consisting of equal volumes of glatiramer acetate in PBS and IFA (DIFCO, Fisher, Pittsburgh, Pa.).

Spinal Cord Lesions: Demyelination and Remyelination Quantitation

Areas of spinal cord demyelination (lesion load) and remyelination (73) were determined from multiple cross-sections of plastic-embedded spinal cords, using a camera lucida system and a computerized drawing tablet (39). Briefly, mice were sacrificed by overdose with sodium pentobarbital and perfused by intracardiac puncture with Trumps fixative, containing 4% paraformaldehyde and 1% glutaraldehyde. Spinal cords were removed, post-fixed in osmium textroxide, and sectioned into 1 mm blocks. Every third block (10–12 blocks per spinal cord; cervical to lumbar range) was embedded in Araldite plastic. The embedded tissues were cross-sectioned at 1 $\mu$m thickness, and the slides stained with 4% paraphenylenediamine to highlight the myelin sheaths.

Using a camera lucida attached to a Zeiss photomicroscope and a ZIDAS interactive digital analysis system, three parameters were measured from each slide: total white matter area, demyelinated lesion area, and remyelination area. Outline of these regions were traced and the areas calculated by the computerized digital analysis system. Demyelination was expressed as the total lesion area as a percentage of total white matter area. Remyelination was expressed as the total remyelination area as a percentage of the total demyelinated lesion area. The criterion for remyelination by oligodendrocytes was abnormally thin myelin sheaths. All remyelination data refers to oligodendrocyte-mediated remyelination. Occasionally, Schwann-cell mediated remyelination was observed, characterized by abnormally thick myelin sheaths and nuclei juxtaposed to the myelin sheath.

Brain Pathology Scoring

Mice were sacrificed and perfused by intracardiac puncture with Trumps fixative, containing 4% paraformaldehyde and 1% glutaraldehyde. Brains were removed and post-fixed in Trumps. Each brain was sectioned coronally into three pieces by cuts through the infundibulum and optic chiasm. The pieces were then dehydrate and embedded in paraffin. Sections from each block were mounted on slides and stained with hematoxylin and eosin to identify pathology in the following brain regions: cortex, corpus callosum, hippocampus, brainstem, striatum, and cerebellum. Pathologic scores were assigned without knowledge of the experimental treatment. Each area of the brain was graded as follows:

0=no inflammation

1=minimal inflammation, confined to perivasculature

2=moderate inflammation, including parenchyma infiltration, but no tissue damage 3=intense parenchyma inflammation with minor but definite tissue damage (loss of tissue architecture, cell death, neurophagia, neuronal vacuolation)

4=extensive inflammation and tissue damage.

Elisa

An indirect ELISA was performed in which serum or a purified antibody was applied to plates that were pre-coated with glatiramer acetate or other protein antigens. The antigen of interest was dissolved in 0.1 M carbonate buffer, pH 9.5, and applied at 1 µg per well in 96-well polystyrene plates. Incubation was overnight at 4° C. Plates were then rinsed with PBST (phosphate buffered saline containing 0.05% Tween 20 detergent) and incubated for 1 hr in PBSM (phosphate buffered saline containing 5% defatted milk powder). Plates were rinsed with PBST, then incubated for 4 hr at room temperature with 50×PBS. Plates were rinsed with PBST, then incubated with biotinylated secondary antibodies that were raised in goat. The secondary antibodies, diluted in PBSM 1:50, were specific to mouse IgG or mouse IgM. Incubation was for 2 hr at room temperature. Plates were rinsed in PBST, then PBS. Streptavidin-alkaline phosphatase conjugate diluted in PBS was applied to the plates for 2 hr room temperature. Plates were rinsed with PBST, with a final rinse in water. The colored reaction product was produced by incubation with p-nitrophenyl phosphatase in 0.1 M carbonate buffer plus 1 mM magnesium chloride. The reaction was stopped with 0.5 N sodium hydroxide. Antibody isotyping was performed using a detection kit and purified isotype standards from Zymed Laboratories (San Francisco, Calif.). Extrapolation of the concentration of each isotype within the antibody samples was based on the sample dilution that produced the absorbence signal falling within the most linear portion of each standard isotype curve. Optical absorbency was measured at a wavelength of 405 nm.

Delayed Type Hypersensitivity (DTH)

Mice were injected intradermally in the ear pinna with 10 µl (3.5 µg) of UV-inactivated TMEV or glatiramer acetate in sterile PBS using a 27-gauge needle. Ear thickness was measured prior to injection, and 24 and 48 hr after injection.

Immunohistochemistry on Cultured Cells

Glial cultures (mixed or oligodendrocyte-enriched) were derived from cerebral hemispheres from 4–7-day-old Sprague-Dawley rat pups (Harlan Sprague Dawley. Indianapolis, Iowa), maintained on poly-lysine-coated glass coverslips in DMEM medium containing 10% fetal bovine serum, and immunostained between Days 4–28 in vitro. CNS glial cultures were also derived from adult human brain biopsies (obtained from surgical correction of epilepsy). Mouse peritoneal macrophages were derived by lavage, 5–8 days following intraperitoneal injection of sterile, 3% thioglycollate solution, and maintained in RPMI medium containing 5% fetal bovine serum for 1–3 weeks.

Spinal cord sections were obtained by cryostat sectioning of frozen spinal cords (10 µm thickness). Sections were lightly fixed in ice-cold 95% ethanol for 5 min and incubated in 10% goat serum to reduce nonspecific staining.

Application of primary antibodies in PBS buffer was performed with ice-cold solutions with culture plate on ice with the intention of staining the cell surface. Primary antibodies were applied for 30–45 min. After rinsing in PBS for 10 min, fluorophore-conjugated secondary antibodies diluted in ice-cold PBS were applied for 30 min. Cells were then rinsed with PBS for 10–15 min. Fixation with 4% paraformaldehyde occurred either once, following the final PBS rinse, or twice, just prior to secondary antibody application and following the final PBS rinse. Cells were viewed with Olympus fluorescent microscopes.

The primary antibodies included antibodies against glatiramer acetate (4–40 ug/ml), Normal antibodies (20 ug/ml), anti-glial fibrillary acidic protein (GFAP, an astrocyte marker) (Dako, Carpinteria, Calif.), O1 (mature oligodendrocyte marker), O4 (oligodendrocyte marker), A2B5 (immature oligodendrocyte marker), 94.03 (oligodendrocyte marker), isolectin $B_4$, CD11b (complement receptor 3)(activated microglia and macrophage markers), rat anti-F4/80 (Serotec, Raleigh, N.C.), biotinylated isolectin $B_4$ from Bandeiraea simplicifolia (Sigma), biotinylated mouse anti-MHC Class II (clone 10.2.16), biotinyiated rat anti-Fcγ III/II receptor (CD16/CD32, BD PharMingen, San Diego, Calif.), rat anti-myelin basic protein (82–87; Calbiochem, San Diego, Calif.). The secondary antibodies were anti-species IgG or IgM, raised in goat, and fluorophore-conjugated (Jackson Immunoresearch; Vector) for direct detection or biotinylated for detection by the peroxidase method using an ABC Elite kit (Vector).

Glatiramer acetate antibodies and normal mouse antibodies were usually applied as biotinylated derivatives. Biotinylation was performed by 30 min incubation of purified antibodies with EZ-Link NHS-LC biotin (Pierce), followed by extensive dialysis against PBS (10,000 molecular weight cutoff). Biotinylation and preservation of glatiramer acetate binding activity was confirmed by Western blot and ELISA. Purified unbiotinylated glatiramer acetate antibodies used in conjunction with a Mouse-on-Mouse Staining Kit (Vector) showed the same staining pattern as biotinylated glatiramer acetate antibodies.

Figure 29:
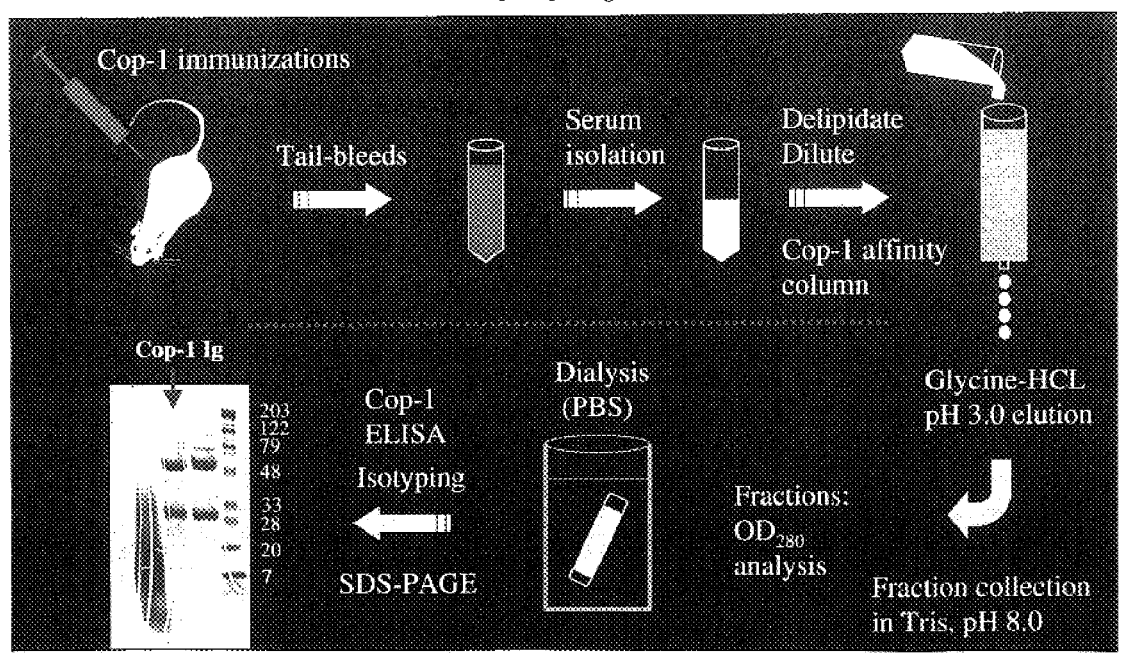
FIG. 29 explains the process of purifying antibodies against epitopes on glatiramer acetate.

Purification of Antibodies Against Glatiramer Acetate in SJL/J Mice (FIG. 29)

The steps involved in purification of antibodies against glatiramer acetate were:

1. Immunization of SJL/J mice. Mice were immunized by eight, subcutaneous injections of glatiramer acetate in IFA (0.1 mg/injection between Days 0–50).

2. Serum isolation. Mice were bled 9 times between Days 14–56 from the time of first immunization. After each bleed, blood was stored overnight at 4° C., then centrifuged to isolate serum. Serum was stored at −20° C. until all bleeds were completed.

3. Affinity column isolation of antibodies against glatiramer acetate. Glatiramer acetate was coupled to NHS-activated Hi-Trap affinity columns (Amersham Pharmacia) by the manufacturer's recommended procedures. Serum was thawed, pooled, centrifuged to remove serum lipid, diluted with phosphate buffer, and run over the glatiramer acetate affinity column twice. After rinsing the column, antibodies against glatiramer acetate were eluted with glycine-HCl (pH 3.0) into Tris buffer (pH 8.0). The $OD_{260}$ of the eluted samples was determined as a measure of protein content. Most of the antibodies against glatiramer acetate were eluted in the first 2 fractions.

4. Dialysis. Eluted fractions containing high levels of antibodies against glatiramer acetate were pooled and dialyzed in PBS (10,000 molecular weight cut-off).

5. Purity and protein analysis. Dialyzed antibodies against glatiramer acetate were analyzed by sodium dodecyl sulphate-polyacrylamide gel electrophoresis (SDS-PAGE) and found to be almost exclusively comprised of product representative of antibody heavy and light chains. Bicichoninic acid protein assay was used to determine the total protein content of the sample, using bovine serum albumin (BSA) as the standard. The determined concentration of 4.8 mg/ml was considered as the concentration of antibodies against glatiramer acetate.

6. Storage. Dialyzed antibodies against glatiramer acetate were filter-sterilized with a 0.22 μm filter and stored at 4° C. Over 2 years of storage, no precipitate or contamination was observed and glatiramer acetate reactivity by ELISA and cellular binding was retained.

Figure 30:
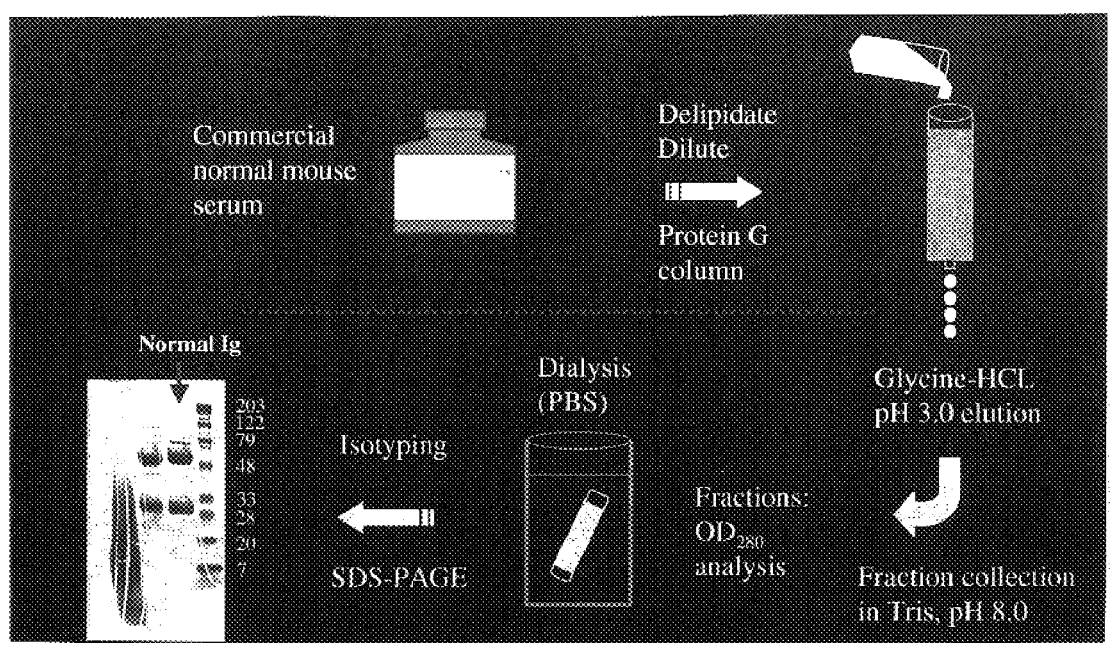
FIG. 30 outlines the steps by which Normal antibodies are purified.

Purification of Normal Antibodies (FIG. 30)

The steps involved in purification of Normal antibodies were:

1. Protein A/G column isolation of antibodies against glatiramer acetate. Normal mouse serum (SIGMA commercial preparation, St. Louis, Mo.) was centrifuged to remove serum lipid, diluted with phosphate buffer, and run over a Protein A/G column (Hi-trap Protein A/G column; Amersham Pharmacia). After rinsing the column, Normal antibodies were determined as a measure of protein content.

2. Dialysis. Eluted fractions containing high levels of antibodies were pooled and dialyzed in PBS.

3. Purity and protein analysis. Dialyzed Normal antibodies were analyzed by sodium dodecyl sulphate-polyacrylamide gel electrophoresis (SDS-PAGE) and found to be almost exclusively comprised of product representative of antibody heavy and light chains. Bicichoninic acid protein assay was used to determine the total protein content of the sample, using BSA as the standard. The determined concentration of 2.6 mg/ml was considered as the Normal antibody concentration.

4. Storage. Dialyzed Normal antibodies were filter-sterilized with a 0.22 μm filter and stored at 4° C. Over 2 years of storage, no precipitate or contamination was observed.

Normal antibodies were also purified by running Normal mouse serum (SIGMA commercial preparation, St. Louis, Mo.) over Protein A/G columns (Pierce, Rockford, Ill.). The antibodies were eluted by conditions similar to those for glatiramer acetate antibodies.

Antibody Injections

All antibodies were dissolved in PBS and administered intraperitoneally. Normal antibodies were protein G-purified antibodies isolated from commercially purchased mouse serum. These were used as a control for antibodies against glatiramer acetate.

EXAMPLE 1

Effect of Glatiramer Acetate Treatment on Extent of Spinal Cord White Matter Pathology During Early Disease Procedure Mice were injected with glatiramer acetate (0.1 mg/injection) in IFA or IFA alone on Day −15 and Day 7, relative to virus injection. Additional injections of either glatiramer acetate alone or phosphate buffered saline (PBS) were performed on Days −7, 0, 13, 21, 32, and 41. Virus was injected on Day 0. Mice were sacrificed on Day 45 post-infection (60 days of glatiramer acetate treatment), and spinal cord demyelinating pathology was measured.

Results

Glatiramer acetate exerted no statistically significant effect on the extent of demyelination by 45 days post-infection (FIG. 1). However, a trend towards reduced demyelination was present (T-test, P=0.08).

EXAMPLE 2

Effect of Glatiramer Acetate Treatment During Late Disease

Experiment 2A: Effect of Glatiramer Acetate on the Extent of Spinal Cord White Matter Pathology During Late Disease Procedure Chronically infected mice (124–365 days post-infection) were treated subcutaneously for periods of 41–76 days. One group of mice received 0.1 mg glatiramer acetate by 8 injections of 0.1 mg each. These mice were sacrificed after 65 days. A second group of mice received 0.1 mg glatiramer acetate/IFA by 4–8 injections at equal intervals, 0.1 mg/injection. The members of this group were sacrificed after 65–76 days. A third group of mice received S mg glatiramer acetate/IFA by 1–2 injections each of 5 mg, an effective dose for inhibiting EAE (32). Sacrifice of these mice occurred after 41–65 days. The control group of mice received PBS. In all groups, spinal cord demyelination was measured after sacrifice.

Results

Figure 2:
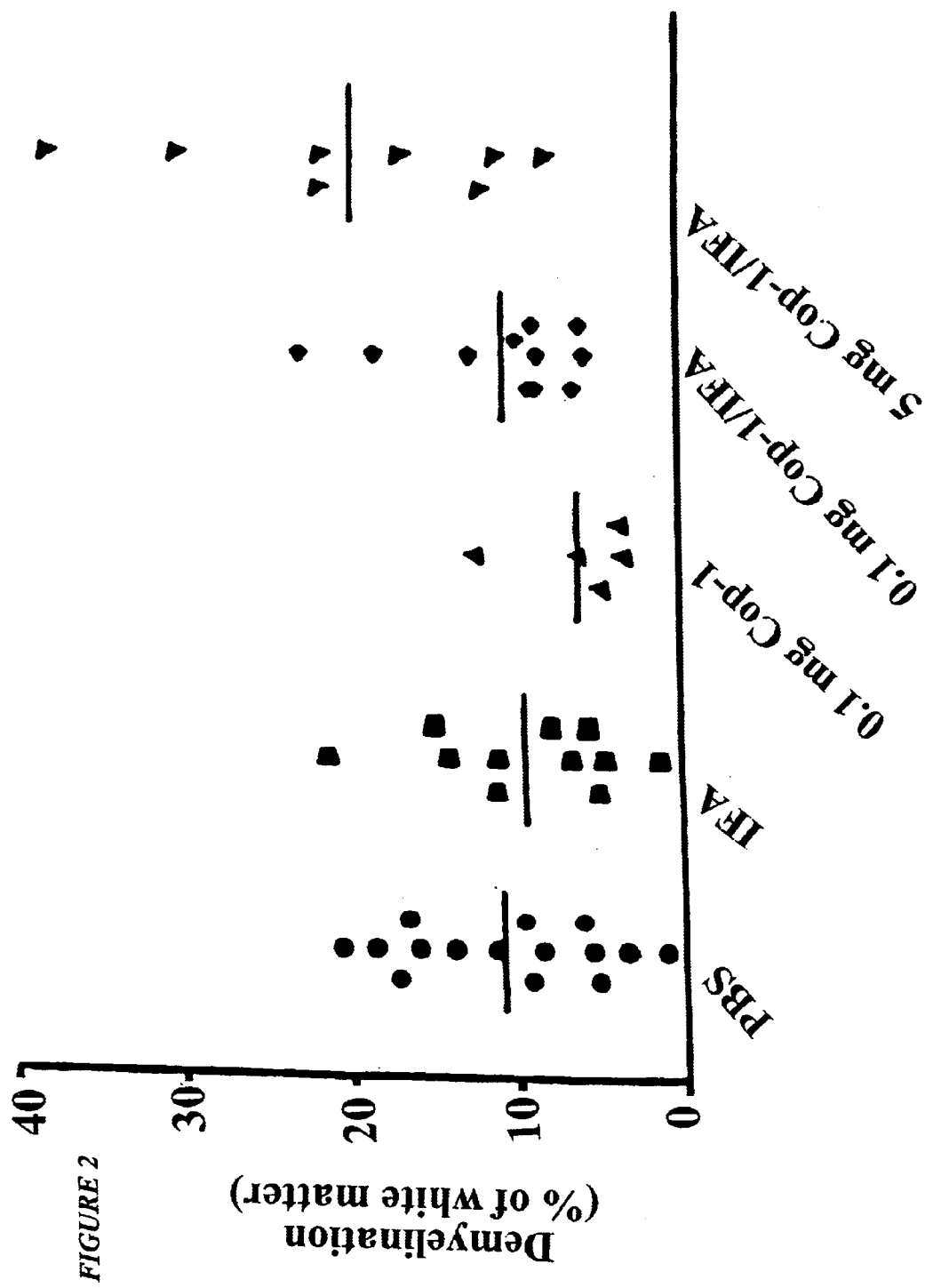
FIG. 2 shows that glatiramer acetate at high doses increases the extent of spinal cord demyelinating lesions during late disease. Each dot represents one mouse.
Figure 21:
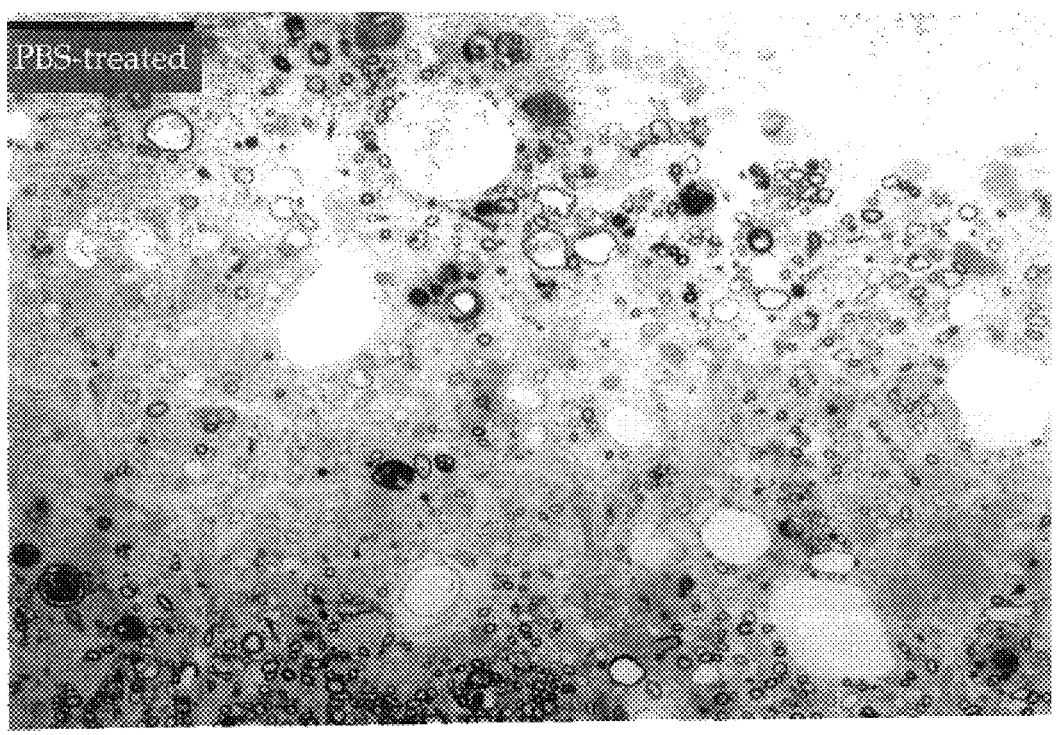
FIGS. 21–22 display demyelinating lesions from chronically diseased, phosphate buffered saline (PBS)-treated mice.

Treatments with the high dose of glatiramer acetate caused an expansion of the demyelinating lesions (P<0.05, compared to PBS treated mice, unpaired t-test) (FIG. 2). Low doses of glatiramer acetate, either alone or in combination with adjuvant, did not alter the extent of demyelination. Lesions were characterized by extensive primary demyelination and infiltration with macrophages and lymphocytes (FIG. 21). On average, 10% of the white matter was demyelinated after treatment with PBS, IFA, or low-dose glatiramer acetate. In contrast, the mean lesion load doubled to 20% after immunization with a high dose of glatiramer acetate, which was significant by t-test (P=0.01 vs IFA)and by one-way analysis of variance (ANOVA, P=0.006, comparing all groups)

Experiment 2B: Effect of Glatiramer Acetate on Extent of Remyelination in the Spinal Cord During Late Disease Procedure Chronically infected mice (124–365 days post-infection) were treated subcutaneously with glatiramer acetate as in Experiment 2A. After sacrifice, spinal cord remyelination was measured in all mice. Spinal cords with less that 4.0% demyelination were excluded from the remyelination analysis (2 from PBS, 1 from IFA and 2 from 0.1 mg glatiramer acetate).

Results

Figure 3:
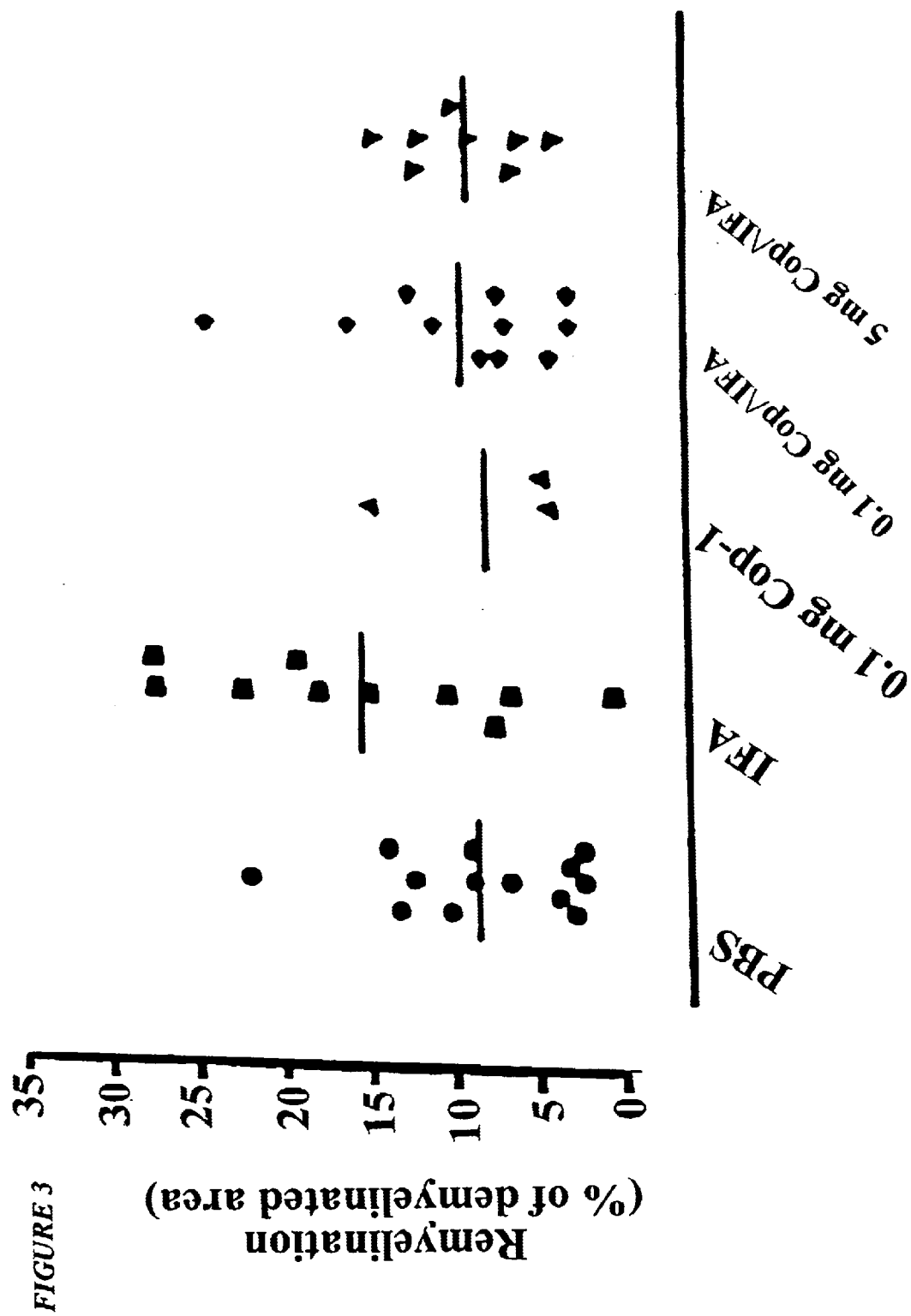
FIG. 3 reveals that glatiramer acetate does not alter the extent of remyelination during late disease. Each dot represents one mouse.

Treatment with glatiramer acetate alone or with IFA did not affect the extent of oligodendrocyre-mediated remyelination during late disease (FIG. 3). Spontaneous remyelination in PBS-treated mice represented 8.5% of the lesion area. IFA alone enhanced remyelination (p<0.05, compared to PBS, unpaired t-test). The beneficial effects of IFA raises the possibility that polyclonal B cell activation with appropriate stimulants might promote remyelination. No treatment effect was seen on the extent of Schwann cell-mediated remyelination, characterized by abnormally thick myelin sheaths, adjacent Schwann cell bodies, and more widely dispersed axonal profiles.

Experiment 2C: Effect of Glatiramer Acetate on Brain Pathology During Late Disease Procedure Chronically infected mice (250 days post-infection) were treated by subcutaneous injection with either PBS, IFA or 1.0 mg glatiramer acetate with IFA, twice weekly for a total of 8 injections. After 29 days of treatment, mice were sacrificed and paraffin-embedded brain sections were scored for the extent of pathology, as explained in the Experimental Methods section.

Results

Figure 4:
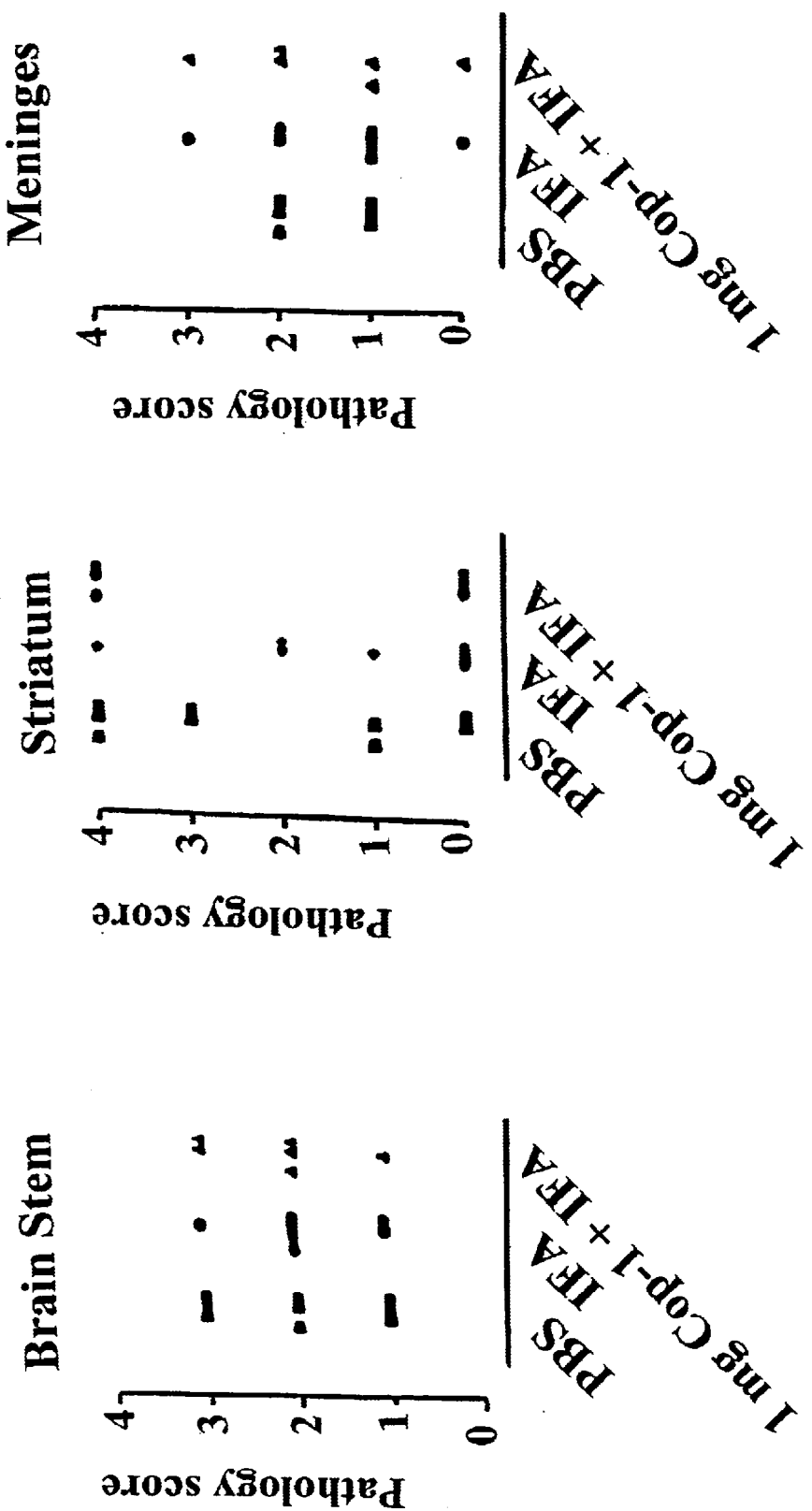
FIG. 4 shows that glatiramer acetate does not alter the extent of brain pathology during late disease. Each dot represents one mouse.

FIG. 4 shows the effect of glatiramer acetate on brain pathology. Each symbol is the score from an individual animal. Glatiramer acetate treatment did not affect the extent of the brain pathology during late disease.

Experiment 2D: Effect of High Dose Glatiramer Acetate on Anti-viral Immunity

Procedure

Chronically infected mice (124–365 days post-infection) were treated subcutaneously with glatiramer acetate as in Experiment 2A. Serum titers of antibodies against TMEV and anti-TMEV DTH reactions were measured.

Results

Four weeks after glatiramer acetate immunization, anti-TMEV titers were reduced (total IgG, IgG1, and IgG2a), compared to control mice, which were statistically significant in 6 of 12 dilutions among the 3 classes of antibodies (Table 1).

TABLE 1

Changes in Anti-viral Immunity Following Glatiramer Acetate Immunization

| Anti-TMEV IgG [a,d] | | TMEV DTH [a,c] | | TMEV Antigen Expression [b] | |
|---|---|---|---|---|---|
| OD | n | Δ mm | n | # of cells/mm2 | n |
| Control 1.08 ± 0.15[e] | 10 | 0.125 ± 0.024[e] | 11 | 9.01 ± 1.71[f] | 12 |
| 5 mg GA/IFA 0.69 ± 0.05[g] | 10 | 0.061 ± 0.039[h] | 10 | 10.83 ± 0.86 | 8 |

All values are means ± SEM
n = number of mice
[a] 4 wk post-immunization
[b] 6–9 wk post-immunization
[c] measured 48 hr post-injection of UV-TMEV
[d] 6250X serum dilution
[e] IFA control immunization
[f] PBS control immunization
[g] p < 0.05 vs IFA, unpaired t-test
[h] p < 0.05 vs PBS, Mann Whitney test Anti-TMEV DTH reactions were also reduced in immunized mice. In 9 out of 10 immunized mice, the TMEV DTH was below the mean of the IFA control group. The remaining mouse had an inexplicably high response that exceeded all control mice. As expected from reduced antiviral immunity, quantitation of virus antigen-positive cells revealed that virus expression tended to be higher 6–9 wks after high-dose immunization. In the glatiramer acetate group, virus expression in 7 out of 8 mice exceeded the mean expression in the control group. As in the DTH experiments, 1 of 12 mice in the PBS control group had uncharacteristically high virus expression (6 standard deviations from the mean of the remaining 11 mice). These results show that glatiramer acetate at a high dose mildly reduced cellular and humoral immunity to TMEV. This reduced antiviral immunity, resulting in increased viral pathogenesis, may account for the increase in lesion load. The reduction may have resulted from the effects of glatiramer acetate-specific T cells which were found in both infected and uninfected mice.

Experiment 2E: Effect of Antibodies Against Glatiramer Acetate on Demyelination During Late Disease Procedure Chronically infected mice (160–477 days post-infection) were treated by intraperitoneal injection with antibodies for periods of 36–76 days. One group of mice received Normal antibodies, administered in 10 injections of 0.05 mg each for a total of 0.5 mg over 42 days. A second group of mice received 0.5 mg antibodies against glatiramer acetate, administered in 10 injections of 0.05 mg each, for a total of 0.5 mg over 41–42 days. The third group of mice received 1.5 mg antibodies against glatiramer acetate, administered in 5 injections of 0.3 mg each for a total of 1.5 mg over 36 days. PBS was administered to the control group of mice. Spinal cord white matter demyelinating pathology was measured post-sacrifice for all mice.

Results

Figure 5:
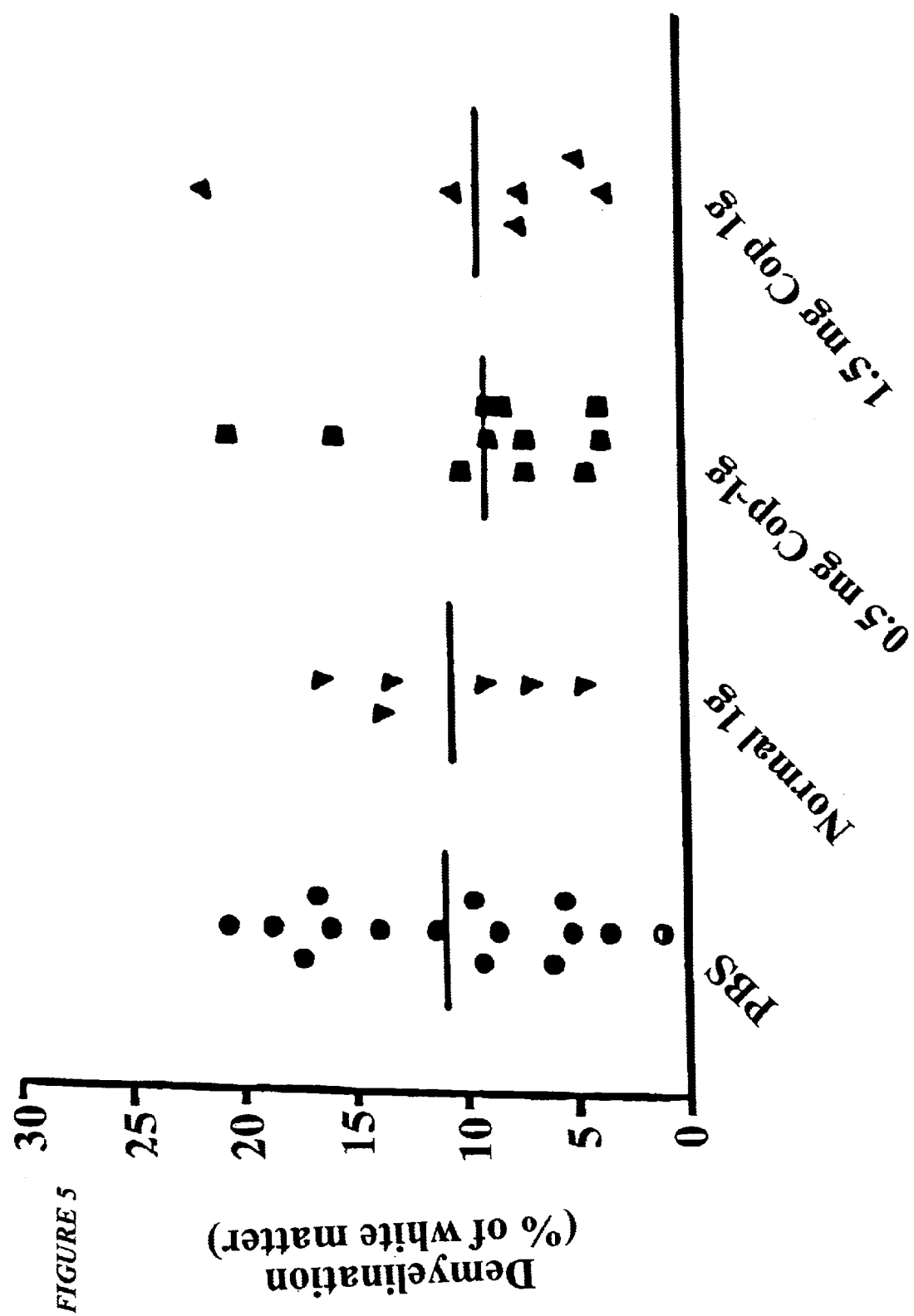
FIG. 5 demonstrates that antibodies against epitopes on glatiramer acetate do not alter the extent of spinal cord demyelinating lesions during late disease. Each dot represents one mouse.

Neither antibodies against glatiramer acetate nor Normal antibodies, when passively transferred, affected the extent of demyelinating pathology during late disease (FIG. 5).

Experiment 2F: Effect of Antibodies Against Glatiramer Acetate on Demyelination During Late Disease (i)

Procedure

Chronically diseased, virus-infected mice were treated for 5–6 wks with glatiramer acetate antibodies or normal antibodies. Each mouse received 5 weekly injections for total antibody doses of 0.5 or 1.5 mg (0.1–0.3 mg/injection). After sacrifice, spinal cord demyelination was measured.

Results

Figure 7A:
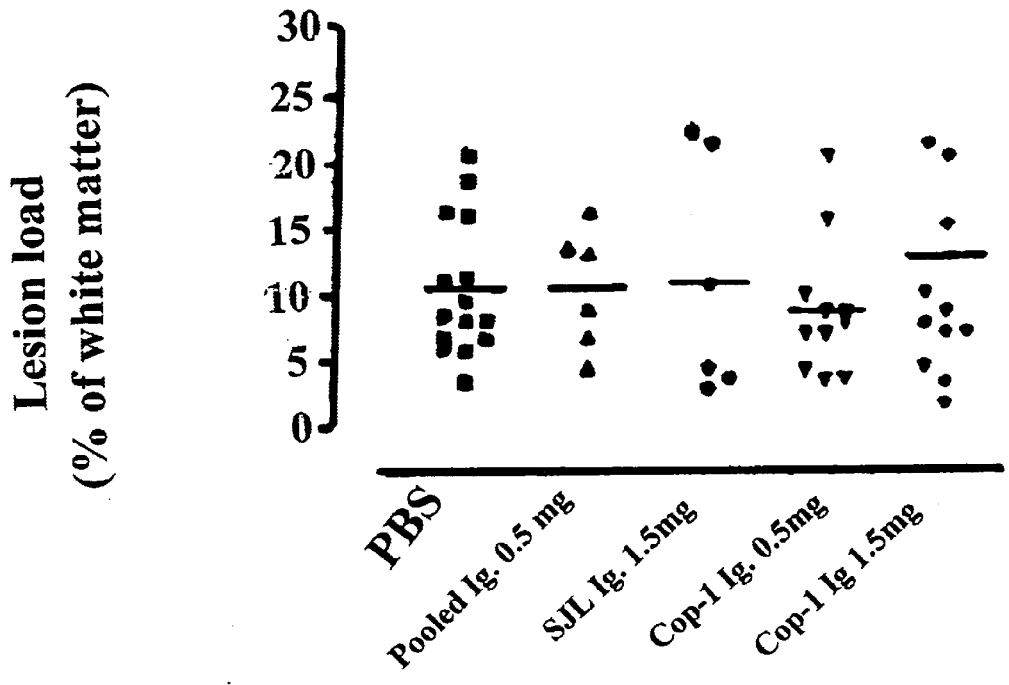
FIG. 7 reports that antibodies against glatiramer acetate do not affect demyelination (FIG. 7A), but promote remyelination (FIG. 7B).

None of the antibody treatments affected lesion load, as compared to PBS-treated mice (FIG. 7a), indicating that glatiramer acetate antibodies were not pathogenic at serum levels of approximately 200 μg/ml or less.

(ii)

Procedure

Chronically infected mice (160–477 days post infection) were treated by antibodies or PBS, following the procedure of Experiment 2E(i). After sacrifice, spinal cord remyelination was measured. Spinal cords with less that 4.0% demyelination were excluded from the remyelination analysis (2 from PBS, 2 from 0.5 mg antibodies against glatiramer acetate, and 1 from 1.5 mg antibodies against glatiramer acetate.

Results

Figure 6:
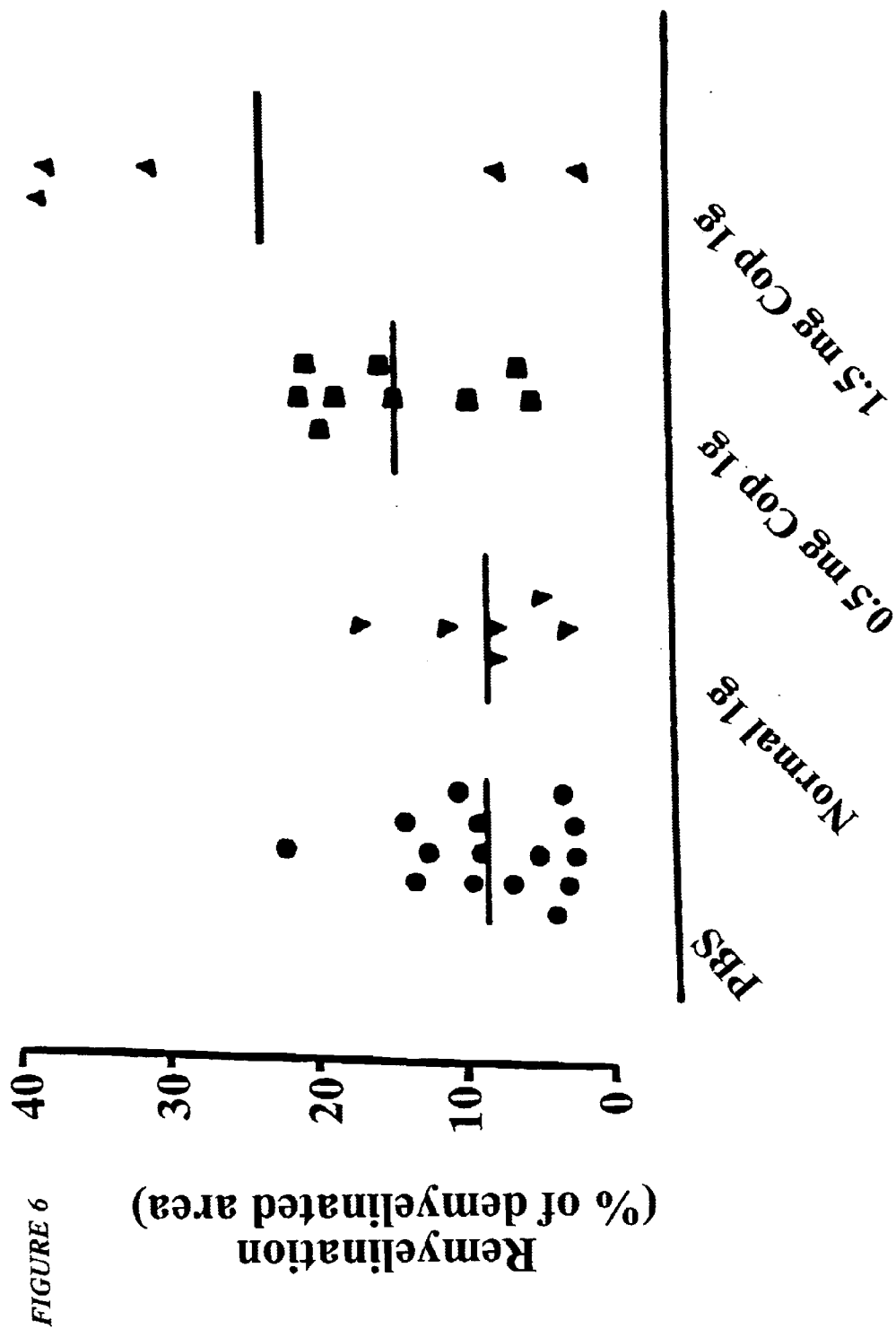
FIG. 6 reveals that antibodies against epitopes on glatiramer acetate promote remyelination during late disease. Each dot represents one mouse.

Glatiramer acetate antibody treatment at both doses increased the extent of remyelination (P<0.05 for both compared to PBS, unpaired t-tests) (FIG. 6). Normal antibodies did not affect remyelination, suggesting that the beneficial effect of antibodies against glatiramer acetate was through specific antigen (epitope) interactions rather than through nonspecific interactions of antibody heavy chains with $F_c$ receptors.

Figure 7B:
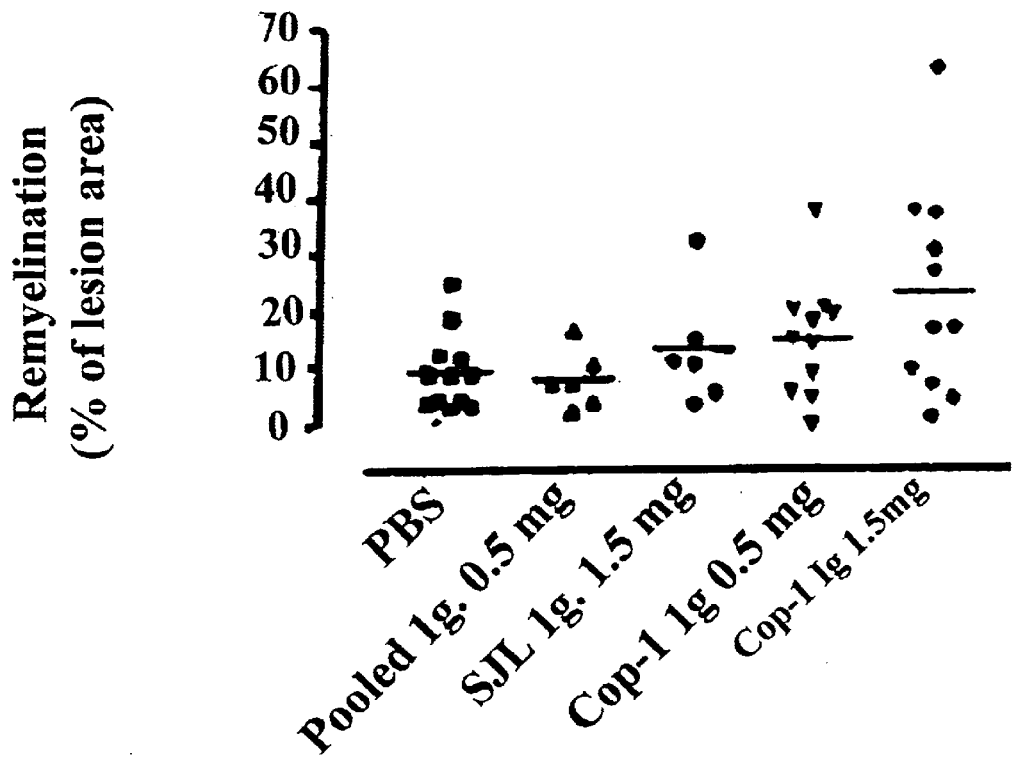
Figure 28:
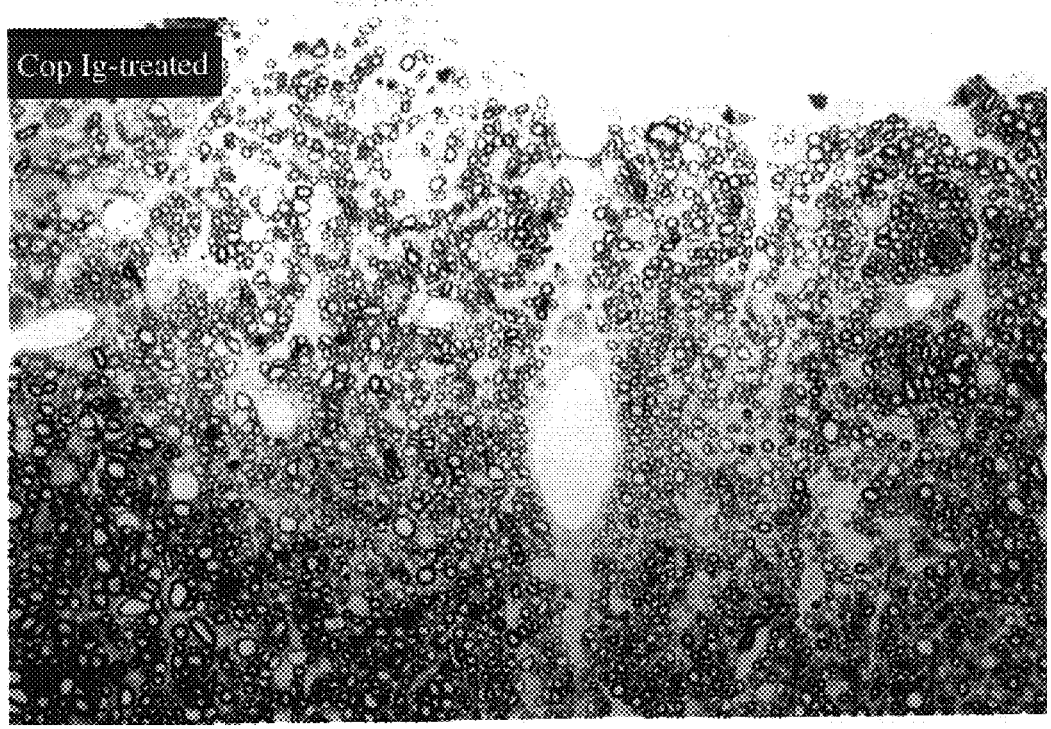

Experiment 2G: Effect of Antibodies Against Glatiramer Acetate on Remyelination During Late Disease
Procedure Chronically diseased, virus-infected mice were treated for 5–6 wks with glatiramer acetate antibodies or normal antibodies. Each mouse received 5 weekly injections for total antibody doses of 0.5 or 1.5 mg (0.1–0.3 mg/injection). Spinal cord remyelination was measured after sacrifice.
Results Glatiramer acetate antibodies had a positive therapeutic effect on oligodendrocyte-mediated remyelination (FIG. 7b). At a total dose of 1.5 mg, mean remyelination was increased 2.4-fold by glatiramer acetate antibodies, which was significant by t-test (P=0.02 vs PBS) and one-way ANOVA (P=0.04 comparing PBS, SJL Ig pooled Ig, and 1.5 mg glatiramer acetate Ig). A positive treatment effect was also indicated by a strong statistical difference between the variances of the 1.5 mg glatiramer acetate antibody group and the other treatment groups (Bartlett's test, P=0.003). Based on axon densities within remyelinated regions, the 2.4-fold increase in remyelination was equivalent to the repair of approximately 7,000–21,000 internodes in the sections that we analyzed. Remyelination also tended to increase with 0.5 mg glatiramer acetate antibody treatment but without statistical significance. Qualitatively, glatiramer acetate antibody-promoted remyelination was of the highest quality seen in these experiments, with some lesions being nearly completely repaired (FIG. 28). Neither normal SJL immunoglobulin nor pooled mouse immunoglobulin significantly promoted remyelination. Thus, in the absence of complete glatiramer acetate immunization and in the absence of oligodendrocyte binding, antibodies to glatiramer acetate stimulated myelin repair.

EXAMPLE 3

Serum Titres of Glatiramer Acetate IgG

Figure 8:
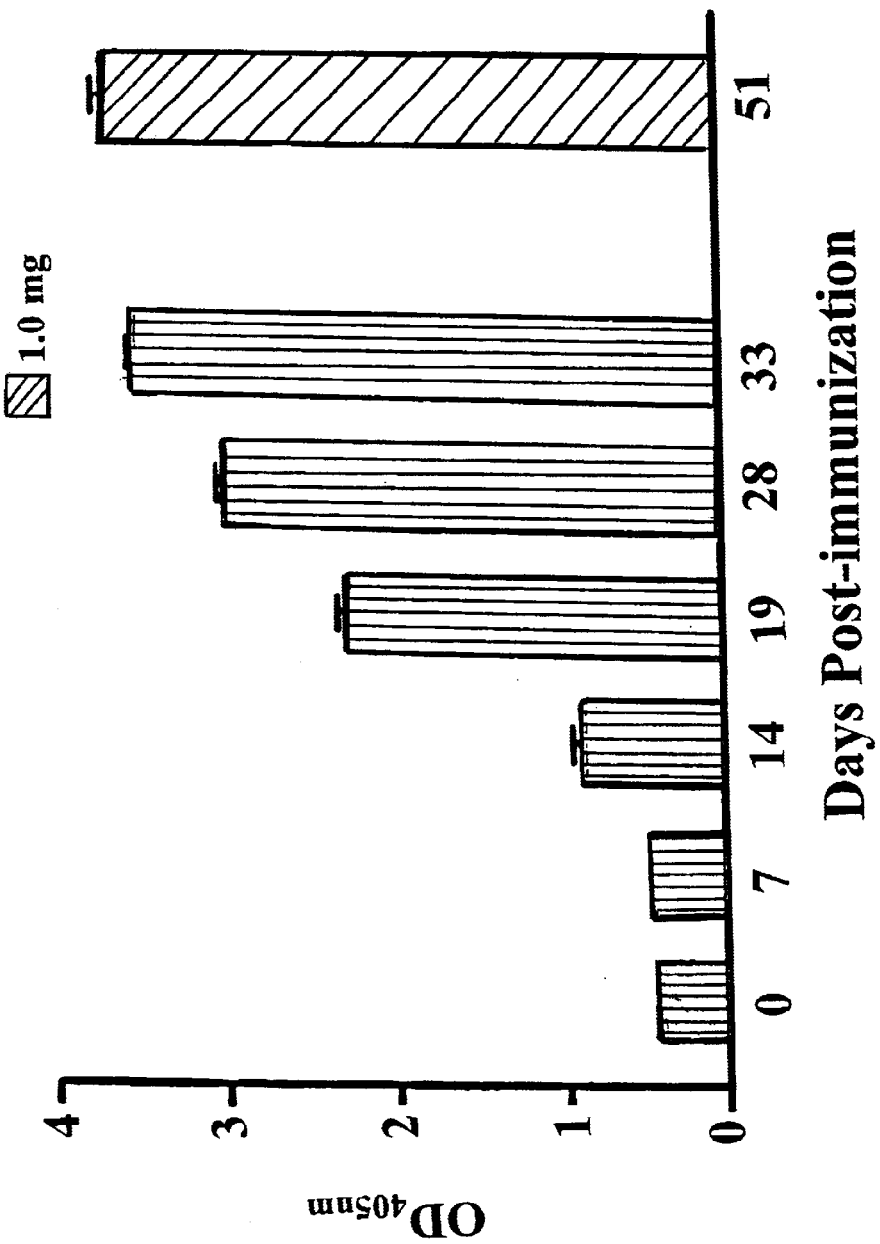
FIG. 8 depicts the glatiramer acetate IgG developed by non-infected mice after immunization.
Figure 9:
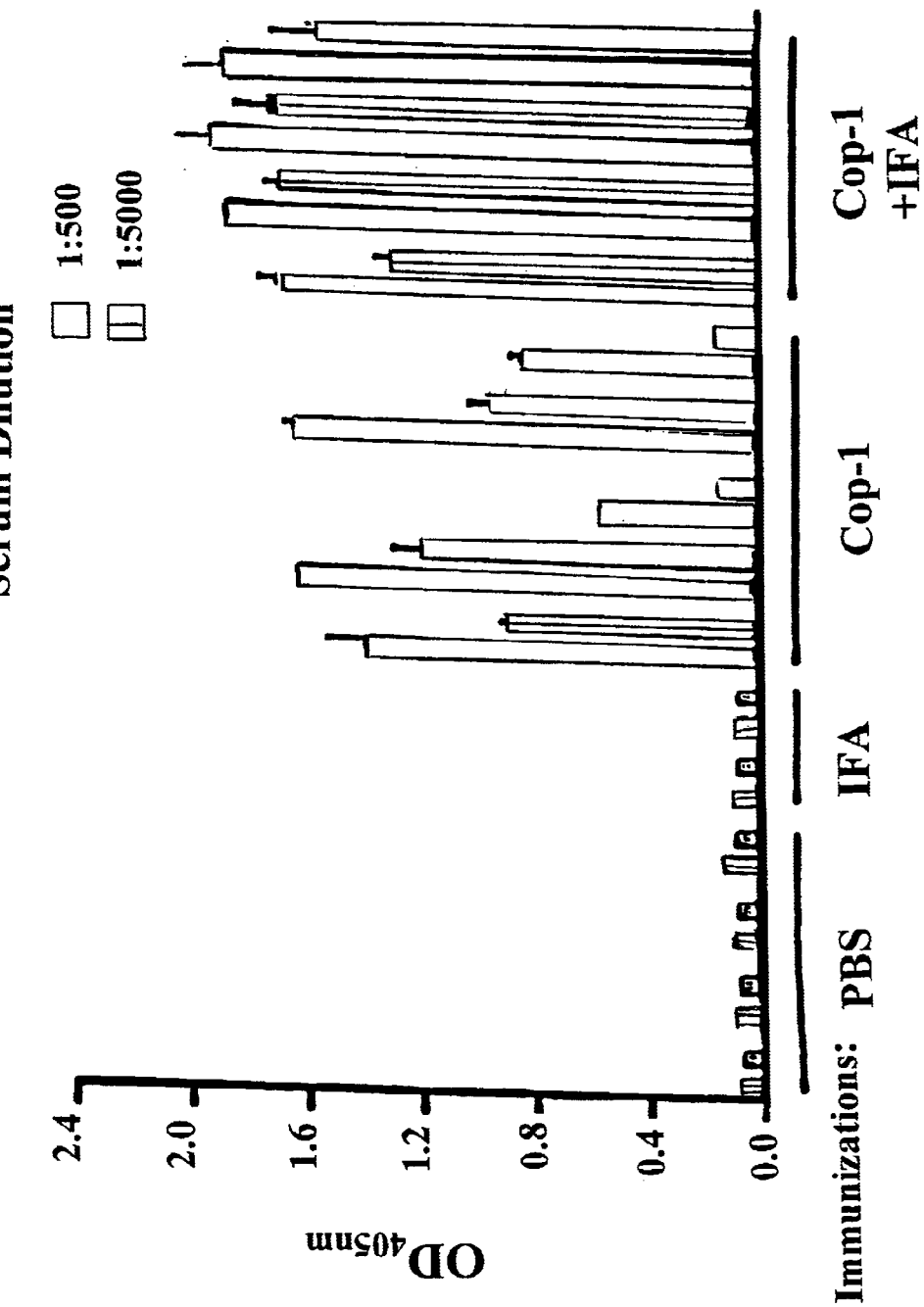
FIG. 9 shows that chronically diseased mice develop antibodies against epitopes on glatiramer acetate in response to glatiramer acetate treatment and that levels of these antibodies are increased by co-administration with incomplete Freund's adjuvant (IFA).
Figure 10:
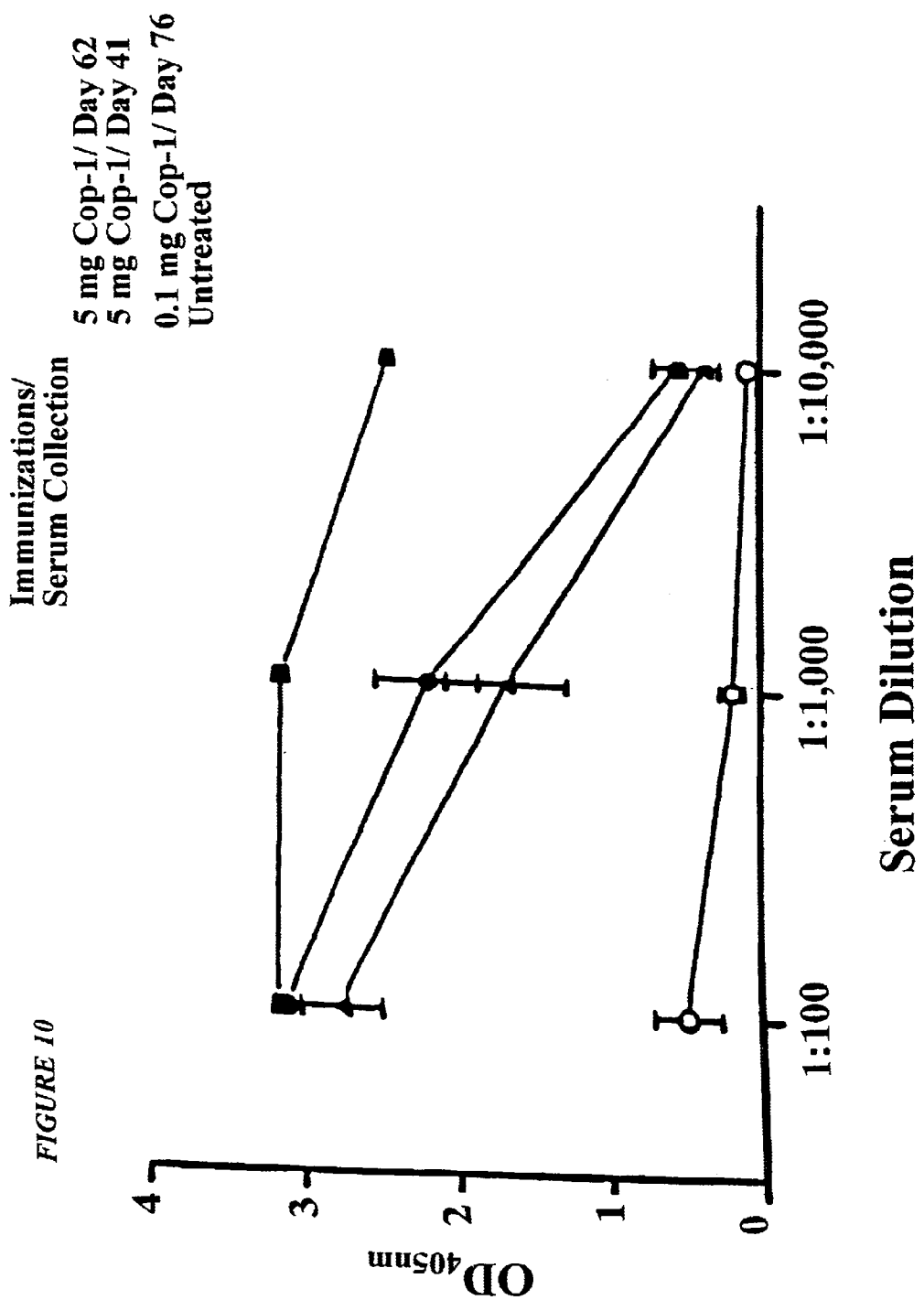
FIG. 10 demonstrates that the levels of antibodies against epitopes on glatiramer acetate increase as a function of time post-immunization and as a function of dose in chronically diseased mice.
Figure 11:
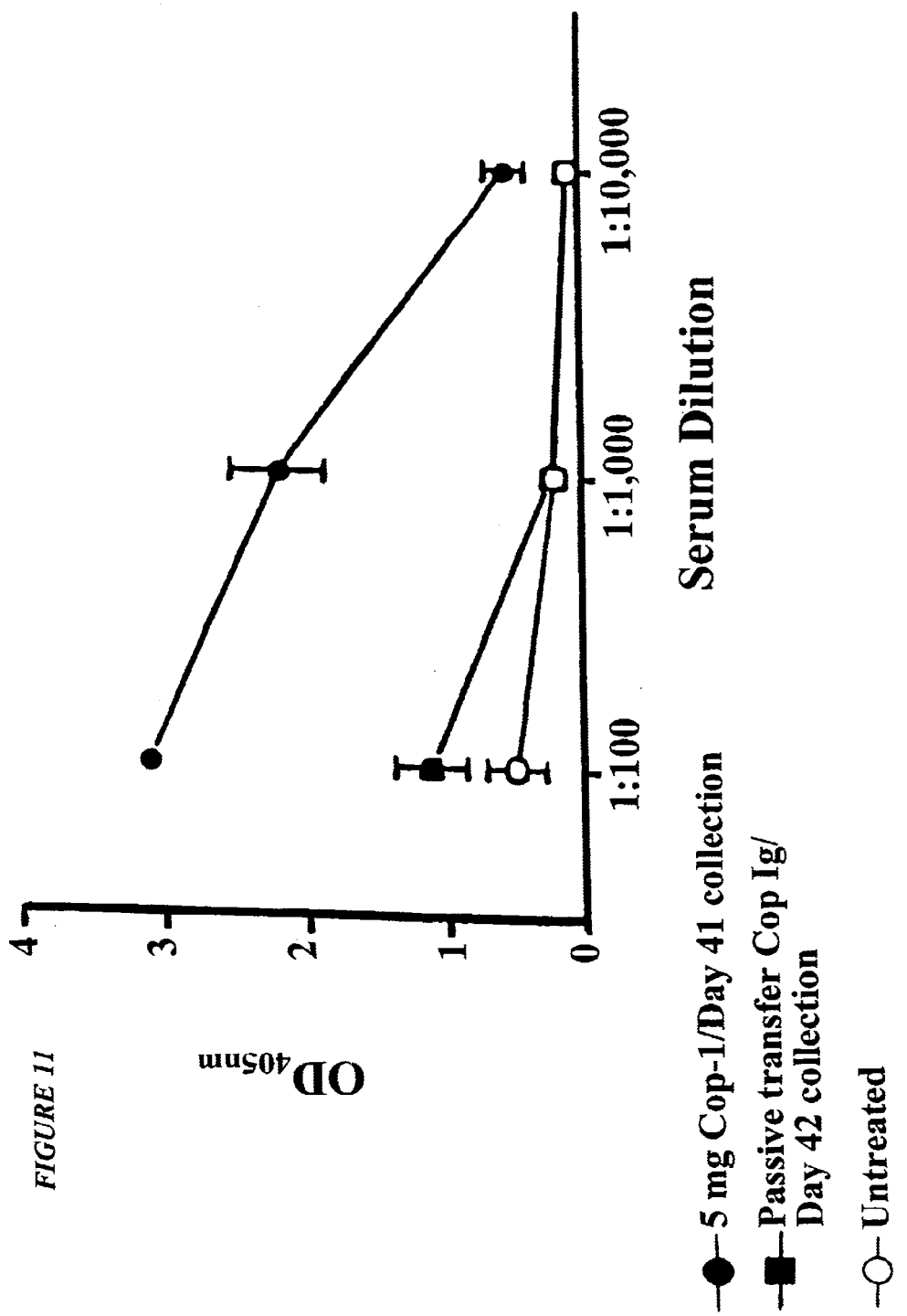
FIG. 11 reveals that glatiramer acetate IgG is detectable in serum 10 days after passive transfer to chronically diseased, non-immunized mice. Individual symbols represent means (±SEM) from 4–6 mice, except the untreated group (2 mice).
Figure 12B:
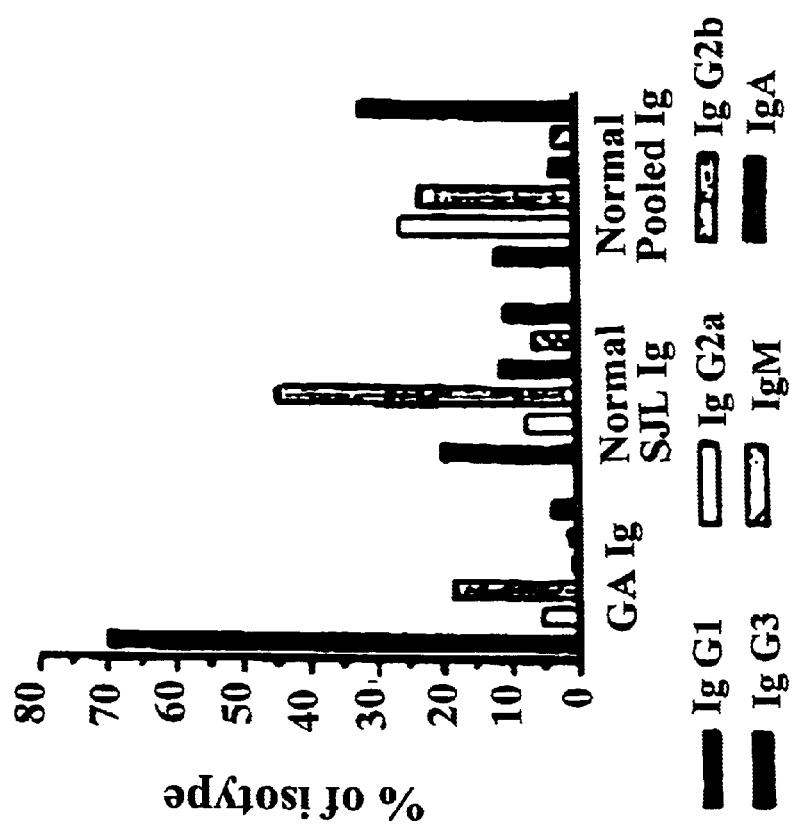
FIG. 12B portrays the isotypes of purifed glatiramer acetate Ig, Normal Ig and pooled mouse serum Ig and shows that IgG1 was the predominant glatiramer acetate isotype.
Figure 12A:
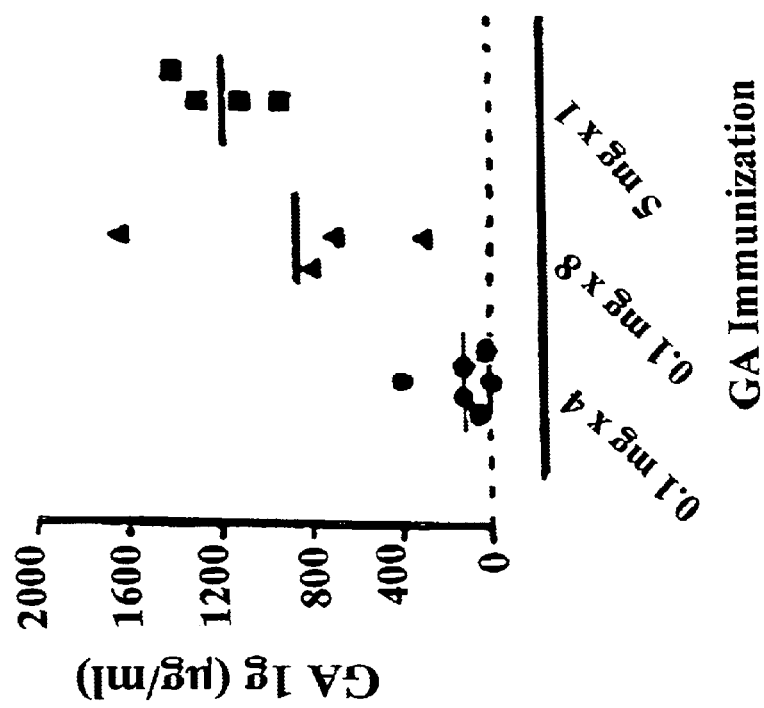
FIG. 12 displays the concentration of glatiramer acetate IgG in serum generally rises with the dosage of glatiramer acetate (FIG. 12A).

Experiment 3A: Serum Titres of Glatiramer Acetate IgG in Non-infected, Immunized Mice
Procedure Non-infected mice were immunized with glatiramer acetate/IFA on Days 0, 4, 8, 15, and 26 (0.1 mg glatiramer acetate/injection) or on Days 0, 3, 7, 10, and 21 (1.0 mg/injection). On Days 0, 7, 14, 19, 28, 33 and 51, blood was collected from 26–35 mice, serum was isolated by glatiramer acetate affinity chromatography (GA Ig) and pooled. Antibodies from normal SJL serum (SJL Ig) and commercial, pooled mouse serum (Pooled Ig) were also purifed by Protein A/G chromatography. ELISA was performed using glatiramer acetate-coated plates and biotinylated anti-mouse IgG as the secondary antibody.
Results Shown in FIG. 8 are the 1:1000 sera dilutions. Serum titres of glatiramer acetate IgG were first detectable 14 days post-immunization and increased over time. Approximately 3 weeks were required to achieve high antibody titres. Varying the glatiramer acetate doses from 0.1–1.0 mg and altering the timing of injections did not significantly influence glatiramer acetate IgG titres, although the immunization and sampling regimens also differed. These data helped to determine how long infected mice should be treated with glatiramer acetate in order to evaluate whether antibodies against glatiramer acetate generated by immunization of infected mice can promote remyelination.
Experiment 3B: Serum Titres of Glatiramer Acetate IgG in Chronically Diseased Mice After Immunization
Procedure Mice infected for 124 days were immunized with glatiramer acetate or glatiramer acetate/IFA at 0.1 mg/injection for a total for 0.8 mg from Days 0–50. Mice were sacrificed on Day 65 post-immunization. Then, serum was isolated and ELISA was performed on glatiramer acetate-coated plates. The secondary antibody was biotinylated anti-mouse IgG.
Results Serum titres of glatiramer acetate IgG were first detectable 14 days following immunization and continued to rise thereafter. There was significant variability in the production of antibodies against glatiramer acetate among individual mice immunized with glatiramer acetate alone (FIG. 9). In contrast, antibody levels were more similar among mice treated with glatiramer acetate and IFA. Immunization with glatiramer acetate and IFA generated much higher antibody levels than immunization with glatiramer acetate alone. No glatiramer acetate IgG was detected in serum from mice treated with either PBS or IFA alone.
Experiment 3C: Serum Titres of Glatiramer Acetate IgG in Chronically Diseased Mice
Procedure Chronically diseased mice, infected for 196–286 days, were immunized with glatiramer acetate. The first group of mice received 5 mg glatiramer acetate/IFA injections on Days 0 and 20. Serum was isolated from these mice on Day 62. The next group of mice received 5 mg glatiramer acetate/IFA injections on Day 0. Serum was isolated from these mice on Day 41. The last group of mice received 0.1 mg glatiramer acetate/IFA injections on Days 0, 25, 37, and 64. Serum was isolated on Day 76. For all groups, ELISA was performed using glatiramer acetate-coated plates. The secondary antibody was biotinylated anti-mouse IgG.
Results Again, serum titres of glatiramer acetate IgG were first detectable 14 days following immunization and increased thereafter. Antibody titers reached a high of 1.2 mg/ml in mice immunized with 5 mg glatiramer acetate (FIG. 12a). The production of antibodies against glatiramer acetate was highly dose-dependent (FIG. 10). Very high glatiramer acetate IgG titres were reached after immunization and a single boost using 5 mg glatiramer acetate injections. The titres were much higher than following 4 injections of 0.1 mg glatiramer acetate. However, relatively high titres were reached even using 0.1 mg glatiramer acetate over time. Individual symbols are the means (±SEM) for 4–5 mice, except for the untreated group (2 mice).
Experiment 3D: Serum Titres of Glatiramer Acetate IgG Following Treatment with Passively Transferred Antibodies Against Glatiramer Acetate vs. Glatiramer Acetate Immunization
Procedure One group of chronically diseased mice (196–348 days of infection) received 5 mg glatiramer acetate in IFA in a single subcutaneous injection. The other group of chronically diseased mice received 10×50 µg intraperitoneal injections of antibodies against glatiramer acetate, twice weekly. The final passive transfer was on Day 35. After 41 days of treatment, both groups of mice were sacrificed and serum titres of Copolymer IgG was measured by ELISA. The secondary antibody was biotinylated anti-mouse IgG.
Results Glatiramer acetate IgG was detected in serum 6 days following the final passive transfer of antibodies against glatiramer acetate, but levels were much lower than in mice that received a single immunization with high dose glatiramer acetate (FIG. 11). Since IgG is cleared with a half-life of approximately 3 weeks, the low serum titre of antibodies against glatiramer acetate 6 days after the final passive transfer suggests that low levels of antibodies against glatiramer acetate are sufficient for promotion of remyelination.

EXAMPLE 4

Reactivity of Purified Antibodies Against Glatiramer Acetate and Purified Normal Antibodies Experiment 4A: Glatiramer Acetate Reactivity of Purified Antibodies Against Glatiramer Acetate and Purified Normal Antibodies: IgG and IgM Procedure The procedures for isolating antibodies against glatiramer acetate and Normal IgG were as described in Experimental Methods. Purified antibodies against glatiramer acetate or Normal antibodies were assayed by ELISA using glatiramer acetate-coated plates. The secondary detection antibodies were either biotinylated anti-mouse IgG or biotinylated anti-mouse IgM.

Results

Figure 13:
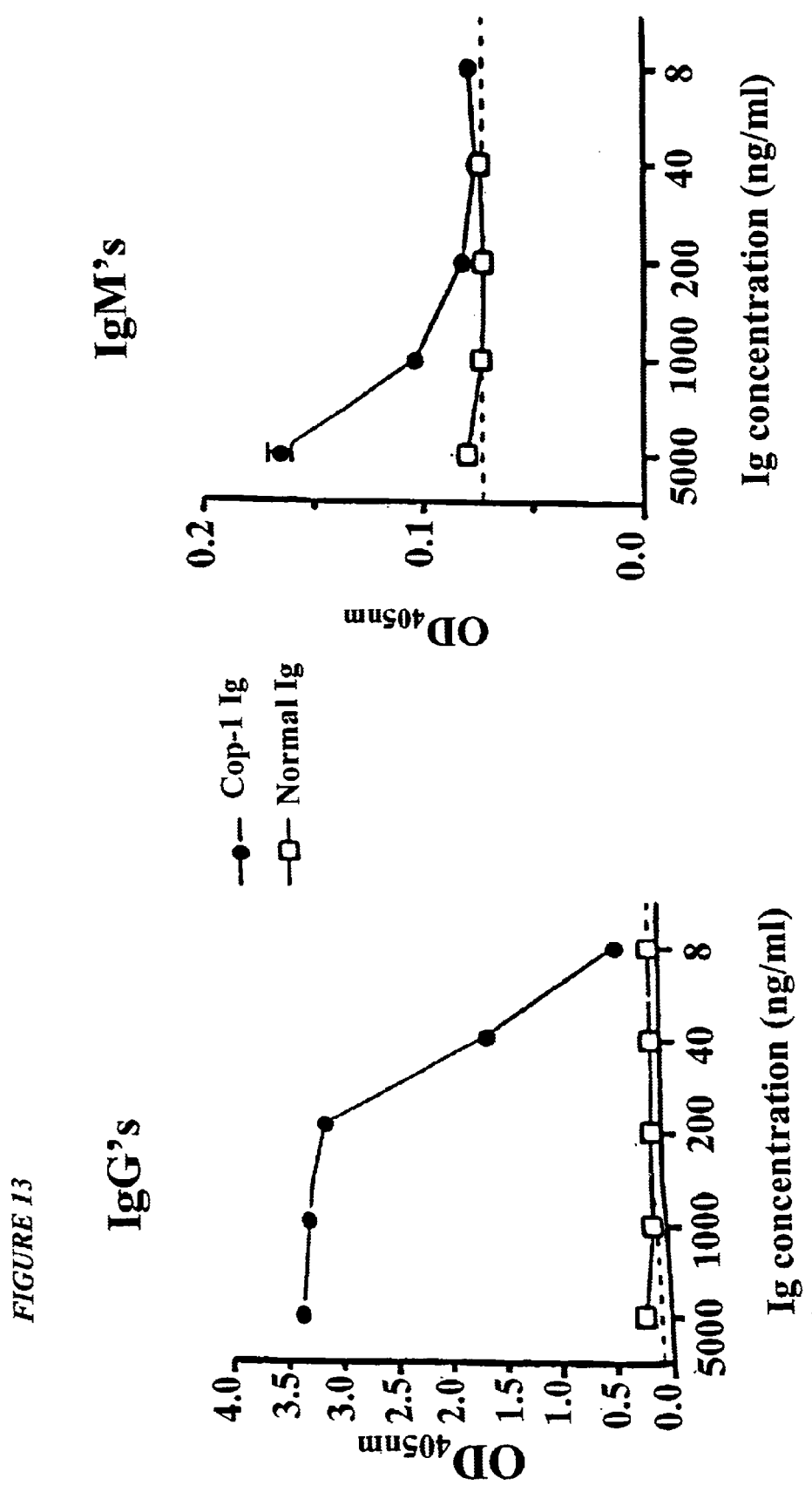
FIG. 13 shows that affinity-purified antibodies against epitopes on glatiramer acetate (IgG and IgM) have high reactivity to Cop-1 by ELISA, whereas Normal antibodies have no reactivity to glatiramer acetate.

Antibodies against glatiramer acetate had high reactivity to glatiramer acetate (FIG. 13). Both glatiramer acetate IgG and glatiramer acetate IgM were detected. Normal antibodies had little or no IgG- or IgM-reactivity to glatiramer acetate.

Experiment 4B: Protein Polyreactivity of Purified Antibodies Against Glatiramer Acetate and Purified Normal Antibodies Procedure Proteins were adsorbed to ELISA plates as described in Experimental Methods. Plates were then reacted with antibodies against glatiramer acetate, Normal antibodies, or SCH 94.03 monoclonal IgM antibodies. Secondary antibodies were anti-mouse IgG or anti-mouse IgM.

Results

Figure 14:
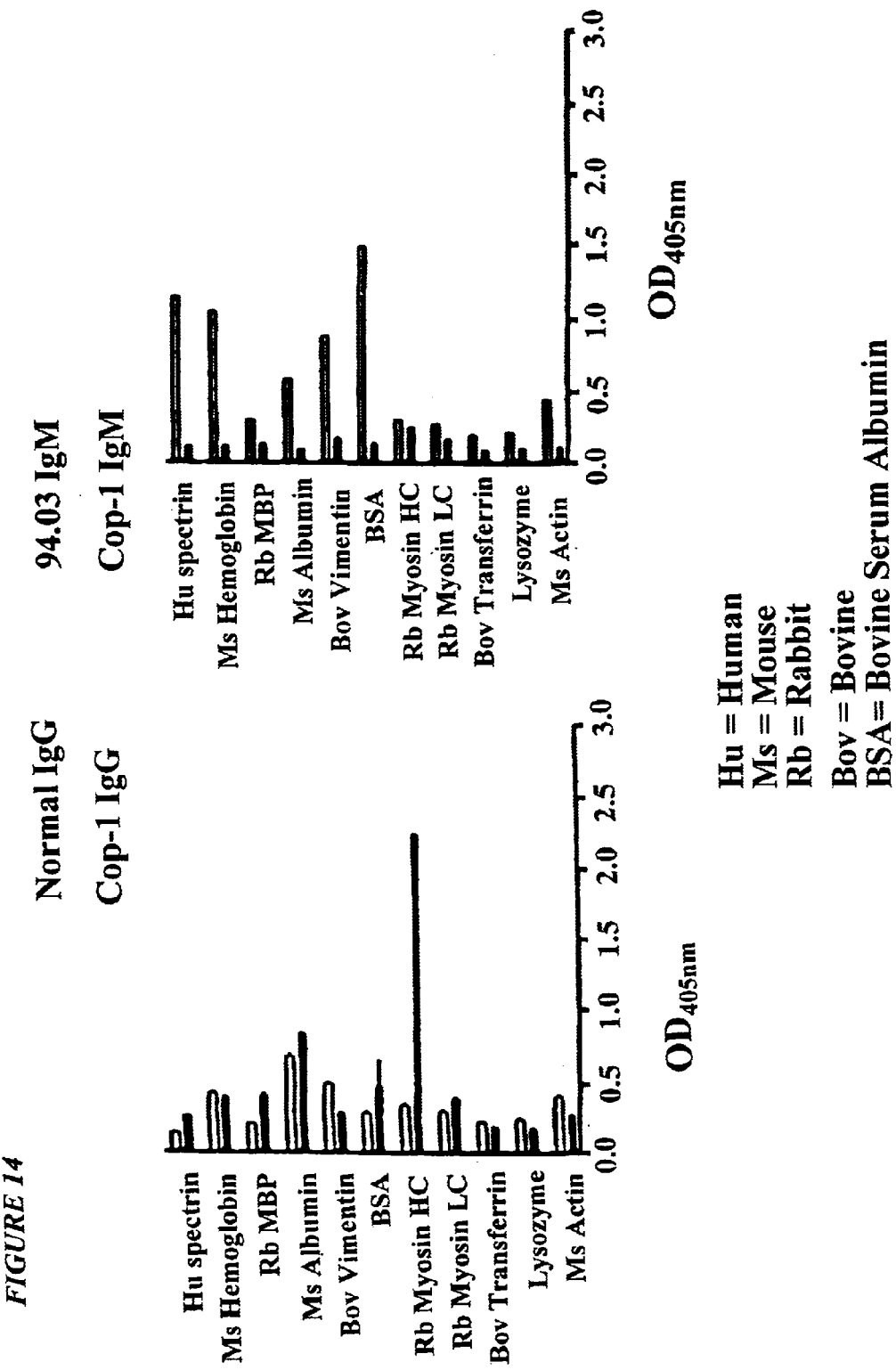
FIG. 14 depicts the low polyreactivity of antibodies against epitopes on glatiramer acetate and Normal antibodies. In the figure, Hu=human; Ms=mouse; Rb=rabbit; Bov= bovine; BSA=bovine serum albumin.

Very low polyreactivity of glatiramer acetate IgG/IgM and Normal IgG was observed (FIG. 14). The only significant cross-reactivity was to rabbit myosin heavy chain. This contrasts with multiple cross-reactivities seen for SCH 94.03 IgM, as reported in U.S. Pat. No. 5,591,629 (1). This supports the hypothesis that the mechanism by which antibodies against glatiramer acetate promote remyelination is different from the mechanism used by polyreactive IgM antibodies such as SCH 94.03.

EXAMPLE 5

Isotype Analysis of Antibodies Against Glatiramer Acetate and Normal Antibodies

Procedure

Purified antibodies against glatiramer acetate and Normal antibodies were isotyped by ELISA using an antibody isotyping kit (Pierce).

Results

Figure 15:
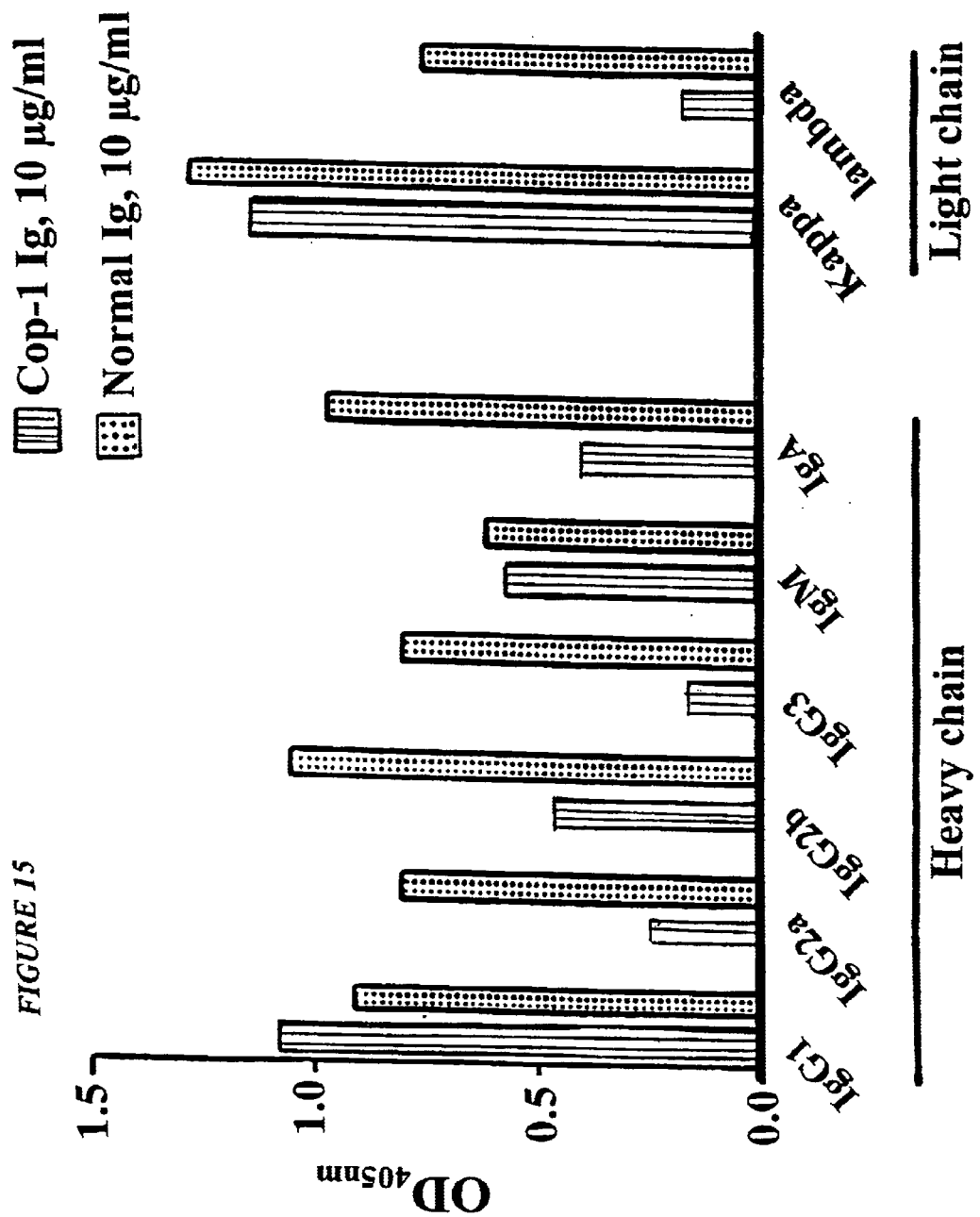
FIG. 15 shows that antibodies against epitopes on glatiramer acetate and Normal antibodies have a wide spectrum of antibody isotypes.

All tested isotypes were found in both glatiramer acetate antibodies and Normal antibodies (FIG. 15). Glatiramer acetate IgG reactivity in the polyclonal glatiramer acetate Ig preparation was strong, being detectable by enzyme-linked immunoabsorbent assay (ELISA) at a concentration as low as 8 ng/ml, whereas IgM reactivity was barely detectable. The glatiramer acetate antibody preparation had a higher relative level of IgG1 than other isotypes, compared to the IgG1 level in Normal antibodies. No glatiramer acetate-reactive IgG or IgM was found in either of the control Ig preparations. By extrapolation from standard curves of purified immunoglobulin isotypes, it was determined that IgG1 comprised 70% of the purified glatiramer acetate Ig (FIG. 12b). IgG2b was the next abundant, representing 18% of the pool. In contrast, IgG2b was most abundant in purified SJL Ig (45%) and IgA was most abundant in the pooled mouse Ig (32%). These results indicated that glatiramer acetate antibodies were produced in abundance in immunized mice, either infected or uninfected, and consisted primarily of isotypes known to poorly activate complement in mice. IgG1 (non-complement fixing in mice) appears to be the most abundant in the antibodies against glatiramer acetate. The apparent abundance of IgG1 implies that complement activation would not be a significant consequence of glatiramer acetate antibody treatment.

EXAMPLE 6

Effect of Antibodies Against Glatiramer Acetate on In Vitro Proliferation of Lymph Node-derived Lymphocytes from $MBP_{84-102}$- and $PLP_{179-191}$- Immunized Mice Experiment 6A: Antibodies Against Glatiramer Acetate Stimulate in Vitro Proliferation of Lymph Node-derived Lymphocytes from Mice Procedure Two mice were subcutaneously injected in the flanks with $MBP_{84-102}$ in complete Fruend's adjuvant (CFA). $MBP_{84-102}$ was obtained by following the procedure of Hawes et al (24). A method similar to that of Tuohy et al. was employed to produce $PLP_{179-191}$ (70). $PLP_{179-191}$ in CFA was subcutaneously injected into the flanks of 1 mouse. After 10 days, inguinal and per-aortic lymph nodes were removed, dissociated, and grown for 53 hours in culture in medium alone or in the presence of $MBP_{84-102}$, $PLP_{179-191}$, Normal antibodies, antibodies against glatiramer acetate or glatiramer acetate. In the last 13 hours of culture, 1 $\mu$Ci of [$^3$H]-thymidine was added and its incorporation measured by scintillation counting of harvested cells.

Results

Figure 16:
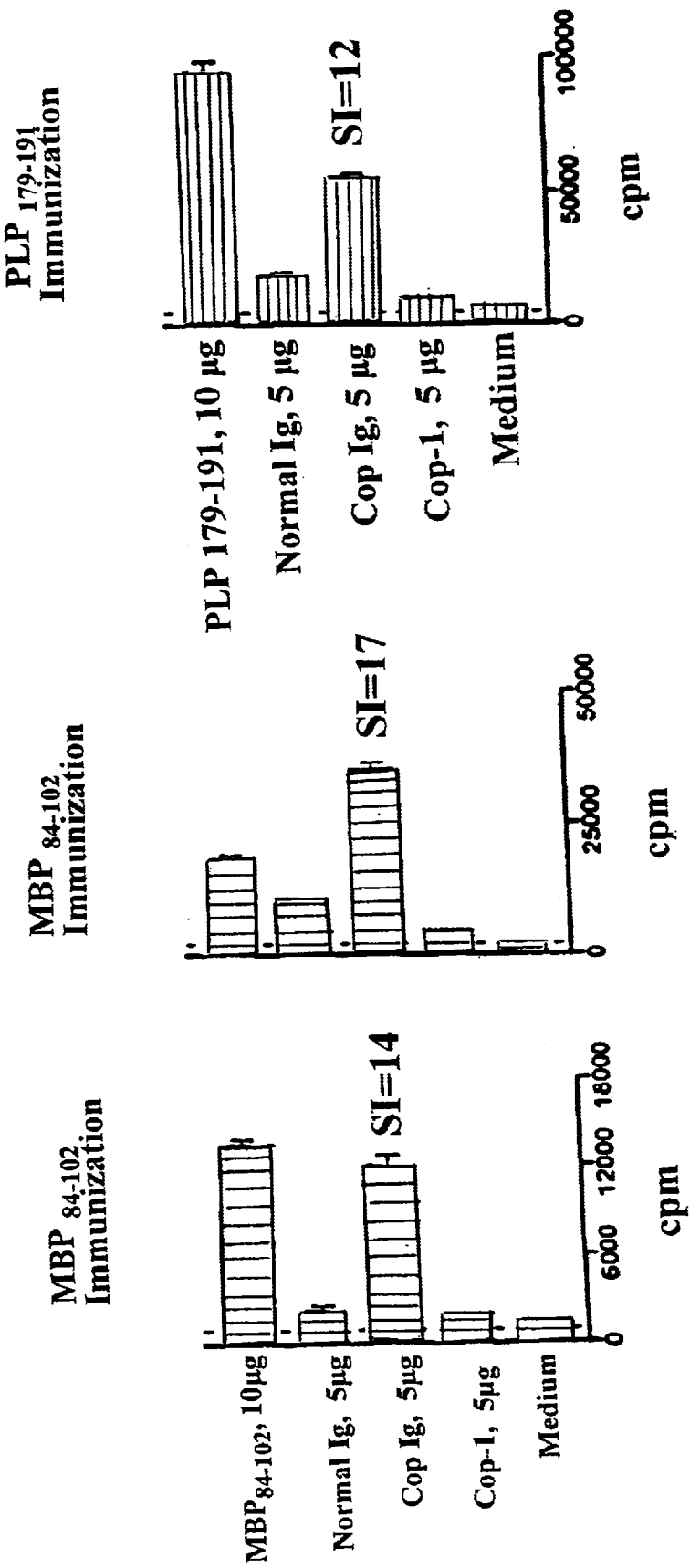
FIGS. 16–18 reveal that glatiramer acetate antibodies stimulate proliferation of lymph node-derived lymphocytes from mice immunized with myelin peptides but not from non-immunized mice. The quantities shown are per 200 μl medium per well.

Antibodies against glatiramer acetate (25 $\mu$g/ml) stimulated lymphocyte proliferation to a comparable level as 50 $\mu$g/ml of specific peptide (stimulation indices=12–17) (FIG. 16). Normal antibody-induced proliferation occurred, but to a much lower level than that induced by antibodies against glatiramer acetate or a specific peptide, suggesting that antigen-specificity of antibodies against glatiramer acetate contributed to its effect. Glatiramer acetate did not induce significant proliferation. The stimulation of proliferation is consistent with an effect of antibodies against glatiramer acetate on antigen presentation, but other explanations, such as direct binding to lymphocytes, are also possible.

Figure 17:
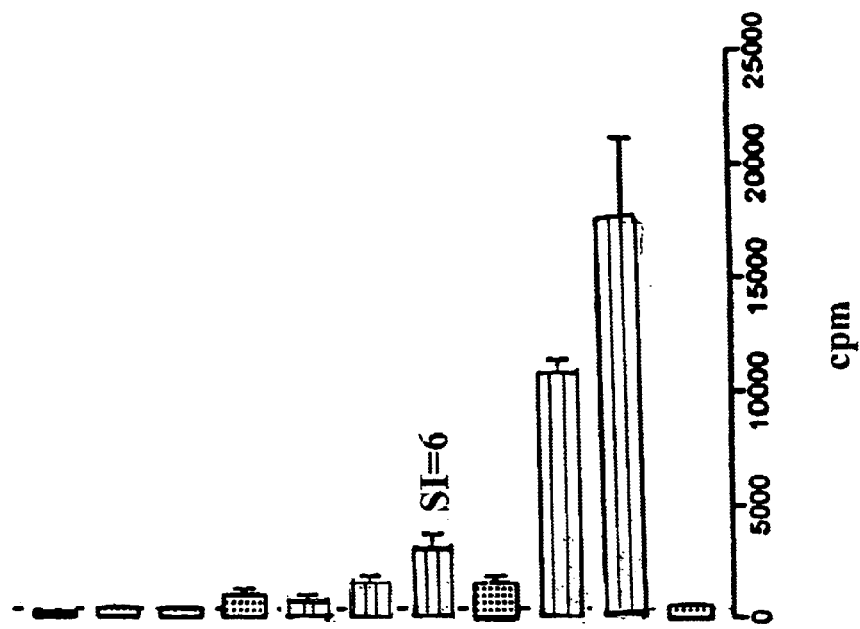
Figure 17:
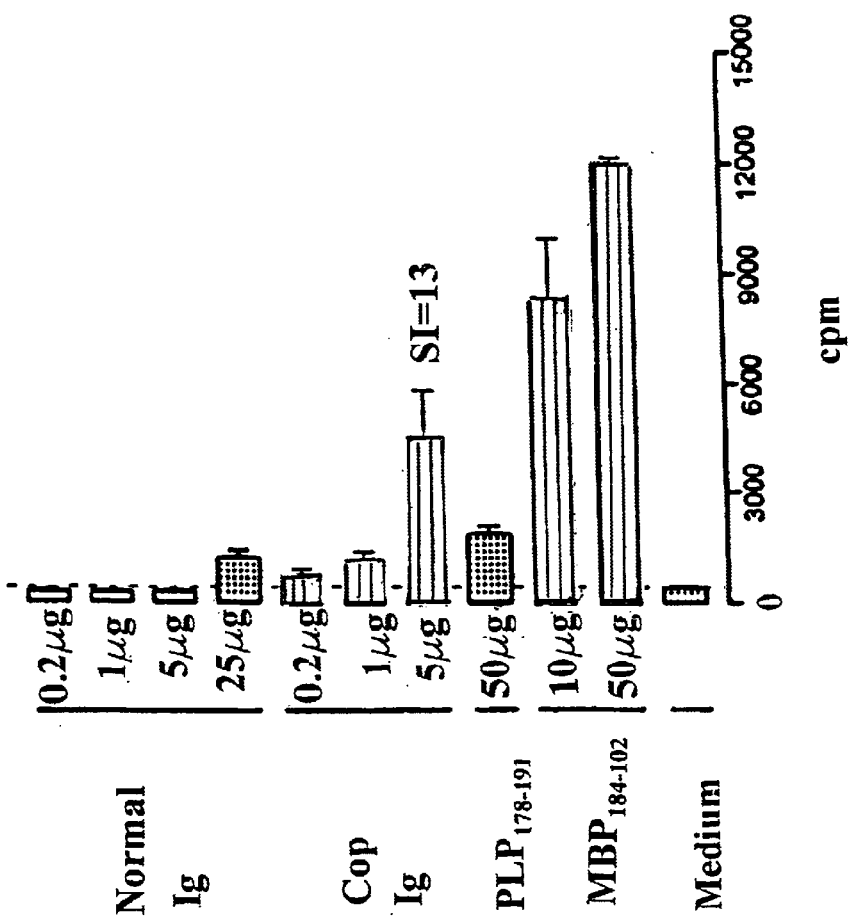

Experiment 6B: Antibodies Against Glatiramer Acetate Stimulate in Vitro Proliferation of Lymph Node-derived Lymphocytes from $MBP_{84-102}$-immunized Mice Procedure Mice were subcutaneously injected in the flanks with $MBP_{84-102}$ (2 mice) peptide in CFA. After 10 days, inguinal and peri-aortic lymph nodes were removed, dissociated, and grown for 74 hours in cultures in medium alone or with additional additives as shown in FIG. 17. In the last 12 hours of culture, 1 $\mu$Ci of [$^3$H]-thymidine was added and its incorporation measured by scintillation counting of harvested cells.

Results

Antibodies against glatiramer acetate (25 ug/ml) stimulated lymphocyte proliferation (stimulation indices=6 and 13) (FIG. 17). Normal antibodies did not induce proliferation at a comparable antibody concentration. As in Experiment 6A, the stimulation of proliferation could be attributed to the effect of antibodies against glatiramer acetate on antigen presentation, but there are other viable theories, such as direct binding to lymphocytes.

Figure 18:
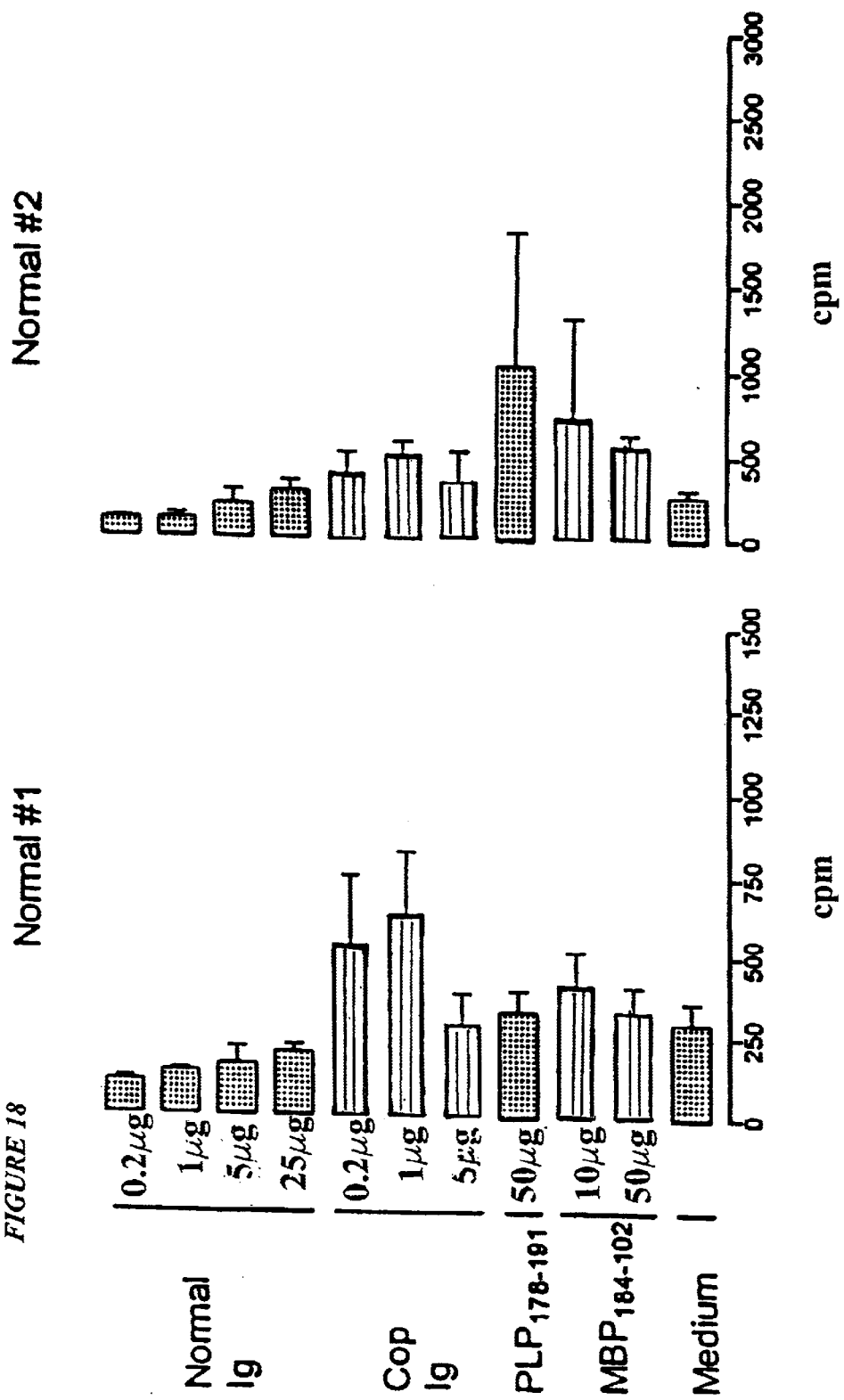

Experiment 6C: Antibodies Against Glatiramer Acetate do not Stimulate in Vitro Proliferation of Lymph Node-derived Lymphocytes from Non-immunized Mice
Procedure Inguinal and peri-aortic lymph nodes from non-immunized SJL/J mice were removed, dissociated, and grown for 74 hours in culture in medium alone or or in the presence of $MBP_{84-102}$, $PLP_{179-191}$, Normal antibodies, antibodies against glatiramer acetate or glatiramer acetate. In the last 12 hours of culture, 1 µCi of [$^3$H]-thymidine was added and its incorporation measured by scintillation counting of harvested cells.
Results FIG. 18 shows that no treatment, including antibodies against glatiramer acetate (25 µg/ml), stimulated lymphocyte proliferation to a significant degree over the baseline level (medium alone). This suggests that antibodies against glatiramer acetate stimulate lymphocyte proliferation (FIGS. 16–17) only during an active immune response to myelin peptides or other antigens.

EXAMPLE 7

Glatiramer Acetate Antibody Binding to Cultured Cells

Experiment 7A: Glatiramer Acetate Antibody Binding to Cultured Cells from the Central Nervous System
Procedure The methodology is described above in the Experimental Methods. Briefly, all staining was performed with ice-cold solutions, with the culture plate on ice, and prior to fixation in order to bind the cell surface. The primary antibodies for these experiments included antibodies against glatiramer acetate, 4–40 µg/ml, Normal antibodies, 20 µg/ml, anti-GFAP (astrocyte markers), O1, O4, A2B5, 94.03 (oligodendrocyte markers), isolectin $B_4$, CD11b (complement receptor 3) (activated microglia and macrophage markers). The secondary antibodies were directed against IgG or IgM of the appropriate species.
Results
CNS Glial Cultures Derived from Neonatal Rat Brains Glatiramer acetate IgG and IgM (secondary antibodies were isotype-specific) stained a small population of cells that were distinct from oligodendrocytes. Mature oligodendrocytes were readily identified by elaborate process extension and by staining with oligodendrocyte markers. In contrast, glatiramer acetate antibody-positive cells did not have elaborate process extension. Rather, they had the phenotype of activated microglia (60) as they were round, located only on the top surface of the culture, sometimes in clusters and always positive with the microglia/macrophage marker, Bandeiraea simplicifolia isolectin $B_4$ (FIG. 23a). They were easily distinguished from early lineage oligodendrocytes (A2B5-positive; FIG. 23b), differentiated oligodendrocytes (O1-, O4-, or MBP-positive; FIG. 23c), astrocytes (glial fibrillary acidic protein (GFAP)-positive) and activated microglia which adhered to the coated-glass substrate. No co-labeling of cells was observed with antibodies against glatiramer acetate or any of the oligodendrocyte markers, whereas cells were co-labeled with glatiramer acetate IgG and the activated microglia markers, isolectin $B_4$ or Mac-1.

Figures 20A, 20B:
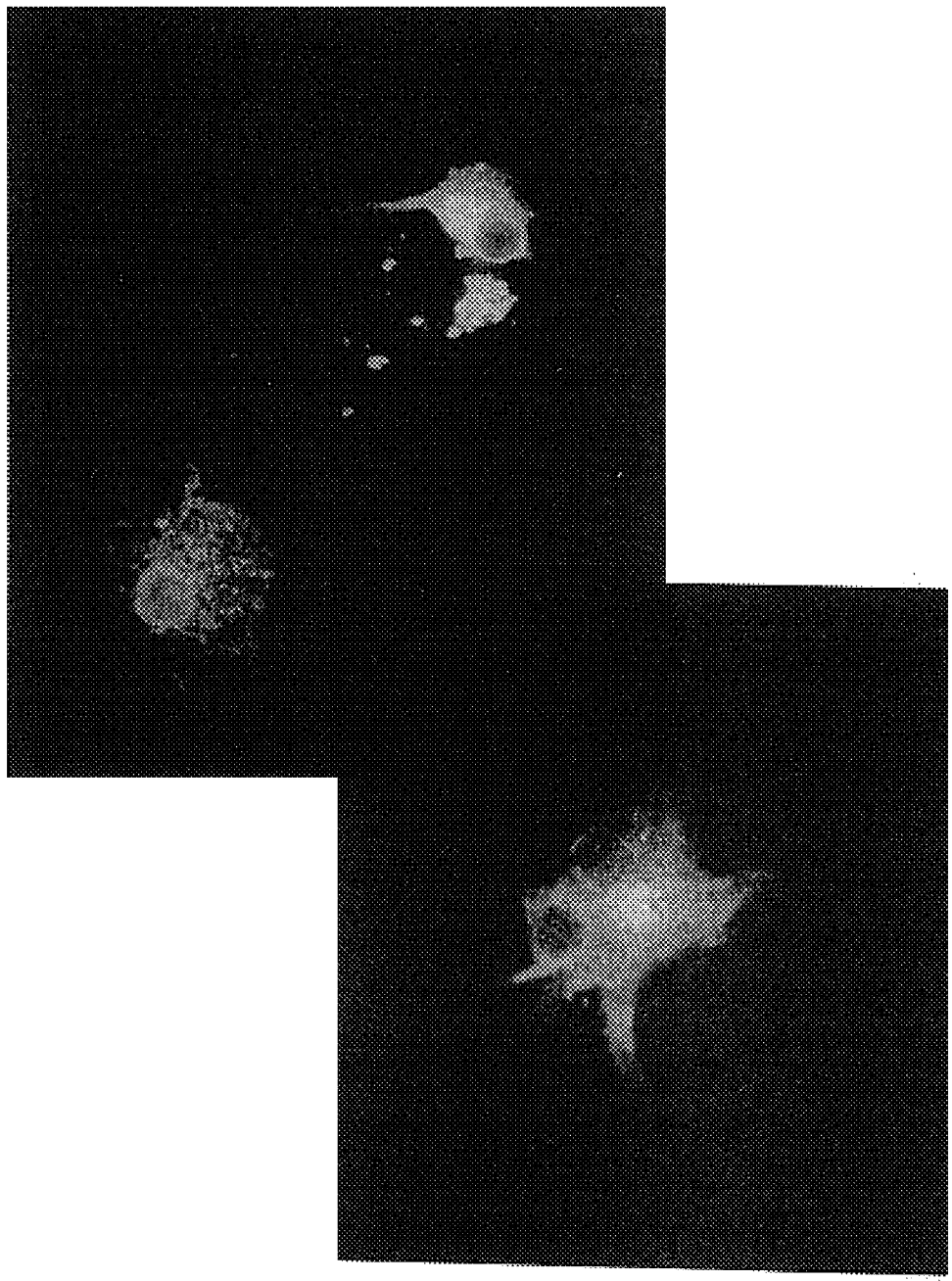
Figures 20C, 20D:
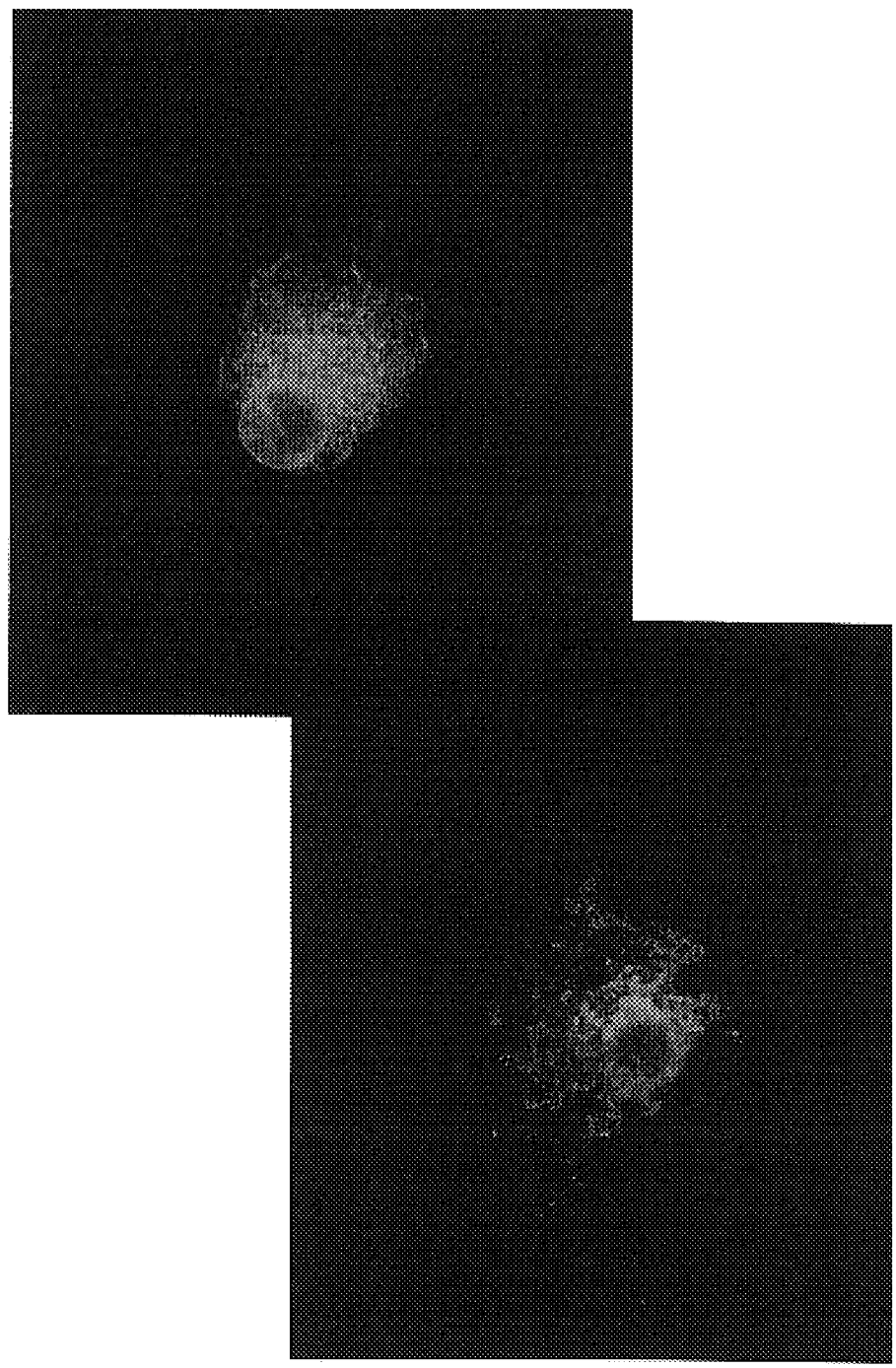

Stronger staining by antibodies against glatiramer acetate was observed after using secondary antibodies directed against mouse IgG than against mouse IgM. Immunostaining with antibodies against glatiramer acetate exceeded the staining by Normal IgG and by secondary antibodies alone, suggesting that antibodies against glatiramer acetate recognized specific cell-surface epitopes rather than being bound simply by non-specific $F_c$ receptors. Very little immunostaining of GFAP (an intracellular antigen) was observed, suggesting that the staining seen with other antibodies (i.e., antibodies against glatiramer acetate) was against cell surface antigens.
Human Mixed Glial Cultures (FIG. 20)

Figure 19:
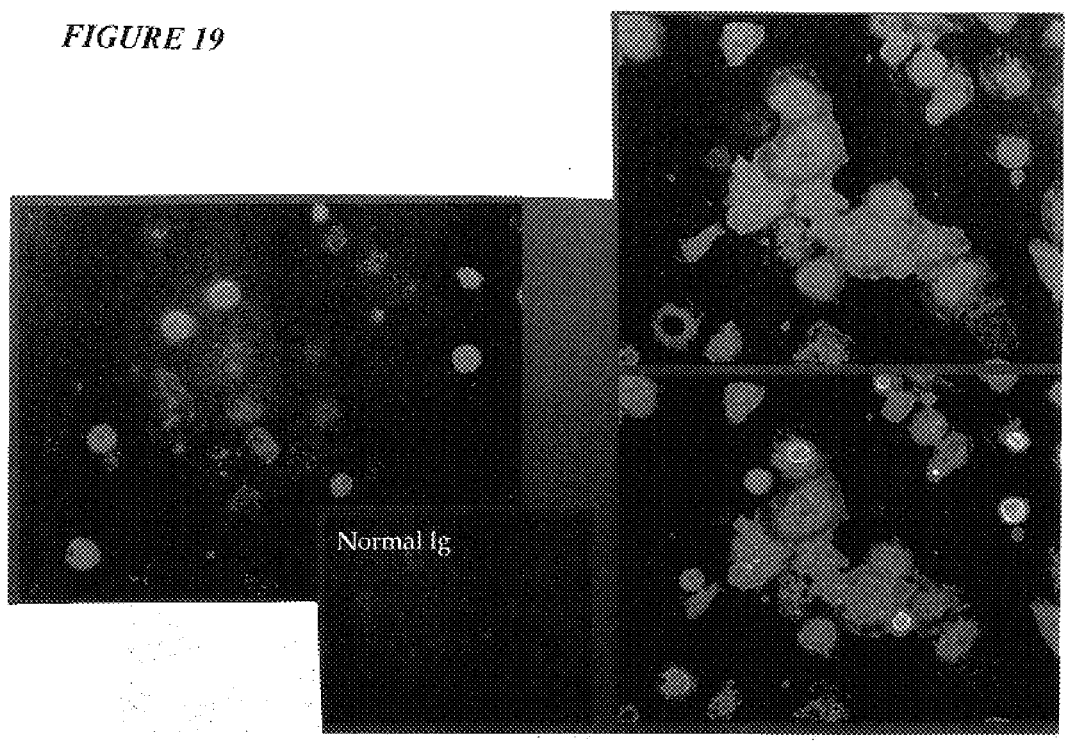
FIGS. 19–20 demonstrate that antibodies against epitopes on glatiramer acetate bind to microglia and macrophages, but not to oligodendrocytes.

In CNS glial cell cultures, a population of cells stained positive for glatiramer acetate IgG. These cells were similar in phenotype to those in rat glial cultures and distinct from the O4-positive oligodendrocytes, which had elaborate process extension. These data are consistent with glatiramer acetate IgG staining of activated microglia, rather than oligodendrocytes.
Experiment 7B: Binding to Cultured Mouse Peritoneal Macrophages by Antibodies Against Glatiramer Acetate
Procedure The methodology is described above in the Experimental Methods. Briefly, peritoneal macrophages (similar in phenotype and function as activated microglia) were derived from the peritoneum of SJL mice, 5 days after intraperitoneal stimulation with 3% sterile thioglycollate broth. Cells were then cultured for 1–3 weeks prior to staining. Antibodies were diluted in ice-cold PBS and the solutions applied to culture plates on ice in order to detect cell surface staining. The primary antibody incubations consisted of combinations of the following: antibodies against glatiramer acetate, 40 µg/ml, Normal antibodies, 20 µg/ml, isolectin $B_4$, CD11b (complement receptor 3) (activated microglia and macrophage markers), glatiramer acetate, 80–200 µg/ml.
Results FIG. 19 demonstrates that incubation with antibodies against glatiramer acetate under cold, unfixed conditions resulted in IgG staining of a subset of cultured mouse peritoneal macrophages, which is consistent with binding to a microglial lineage cell. Surface binding in both glial and macrophage cultures was not simply due to nonspecific interaction with Fc receptors, as no staining was observed with pooled mouse Ig. Acetone fixation/permeabilization prior to incubation with antibodies against glatiramer acetate resulted in intense staining of all cells, suggesting that antibodies against glatiramer acetate were highly reactive to intracellular antigens. Normal antibodies did not stain acetone-fixed cells. Fixation with 4% paraformaldehyde prior to incubation with antibodies against glatiramer acetate did not significantly alter the staining pattern as compared to fixation following incubation with antibodies against glatiramer acetate. Glatiramer acetate IgG-positive cells always co-stained with isolectin $B_4$ and Mac-1.

Four-hour pre-incubation of macrophages at 37° C. with a variety of agents (20 µg/ml glatiramer acetate, myelin homogenate, kidney homogenate, $MBP_{84-102}$, $PLP_{179-191}$) did not influence subsequent staining by glatiramer acetate IgG, compared to cells preincubated only with medium. This suggests that MHC Class II presentation of processed glatiramer acetate or other antigens at the cell surface did not influence the binding of antibodies against glatiramer acetate.

Co-incubation of antibodies against glatiramer acetate with glatiramer acetate and macrophages greatly increased the intensity of glatiramer acetate IgG staining and the number of cells stained, suggesting that antibodies against glatiramer acetate complexed with glatiramer acetate bound much more extensively to macrophages than antibodies against glatiramer acetate alone. Co-incubation of antibodies against glatiramer acetate with myelin homogenate, SCH, or kidney homogenate did not alter glatiramer acetate staining. Punctate staining was present only when antibodies against glatiramer acetate were co-incubated with glatiramer acetate.

This staining pattern was indicative of clustered receptors, suggesting that MHC Class II molecules may have been bound by glatiramer acetate.

Glatiramer acetate IgG (biotinylated) bound extensively to spinal cord sections from both normal and Theiler's virus-infected mice (FIG. 23d). Similar to glial cultures, reactivity to oligodendrocytes or CNS myelin was not observed. In the white matter, glatiramer acetate IgG recognized a subset of presumed glia, particularly their network of thin, randomly oriented processes. Glatiramer acetate Ig-positive structures often co-labeled with GFAP, indicative of astrocyte recognition. Glatiramer acetate IgG also outlined most perivascular infiltrating cells in lesioned cords, which consist of macrophages, microglia, and lymphocytes. Only a low level of background staining was found using control biotinylated pooled mouse Ig (FIG. 23e).

Discussion

By morphological and co-immunolabeling criteria, antibodies against glatiramer acetate bound to subpopulations of activated microglia and macrophages in culture. This staining pattern contrasts with that of monoclonal antibody SCH 94.03 and other remyelination-promoting antibodies, which bind preferentially to the surface of oligodendrocytes (1). Glatiramer acetate IgG staining was stronger than glatiramer acetate IgM staining. Antibodies against glatiramer acetate bound both surface and intracellular antigens. Staining of antibodies against glatiramer acetate was greatly increased by co-incubation with glatiramer acetate, but not by pre-incubation of macrophages with glatiramer acetate.

The increased staining following co-incubation with glatiramer acetate might reflect binding of glatiramer acetate: antibody complexes to MHC Class II molecules, which are known to bind glatiramer acetate (19, 69). In addition, the binding to microglia/macrophages in viva might modulate cellular function, thereby triggering a more permissive environment for remyelination.

EXAMPLE 8

Lesion Pathology and Remyelination Procedure

Chronically infected mice (6 months or longer post-infection) were treated with PBS, glatiramer acetate (0.1 mg/injection), or antibodies against glatiramer acetate (1.5 mg total).

Results

PBS Treatment

Figure 22:
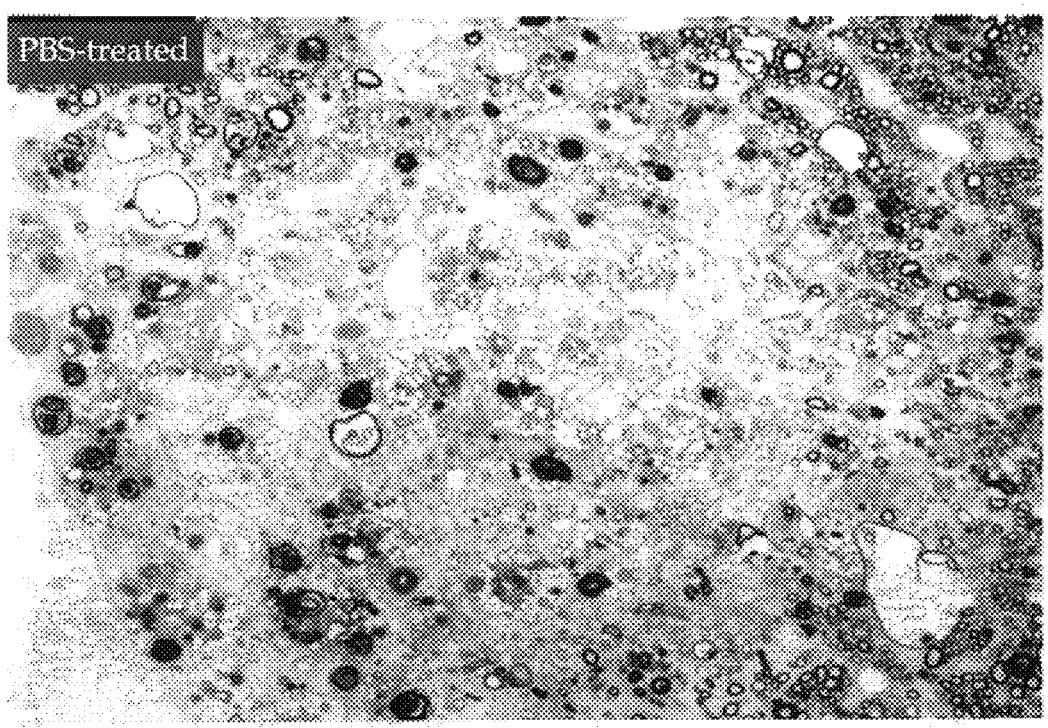
Figure 24:
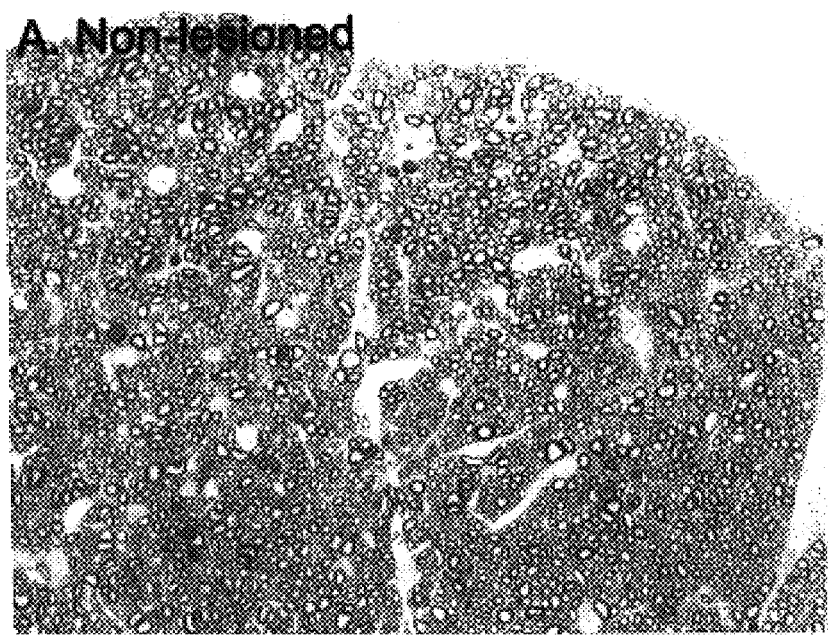
FIG. 24 depicts a cross-section of spinal cord white matter stained for myelin showing normal myelin architecture.

Mice treated with PBS showed extensive demyelination and macrophage filtration of lesions. Remyelination, characterized by abnormally thin myelin sheaths, was virtually absent (FIGS. 21–22).

Glatiramer Acetate Treatment

Figure 25:
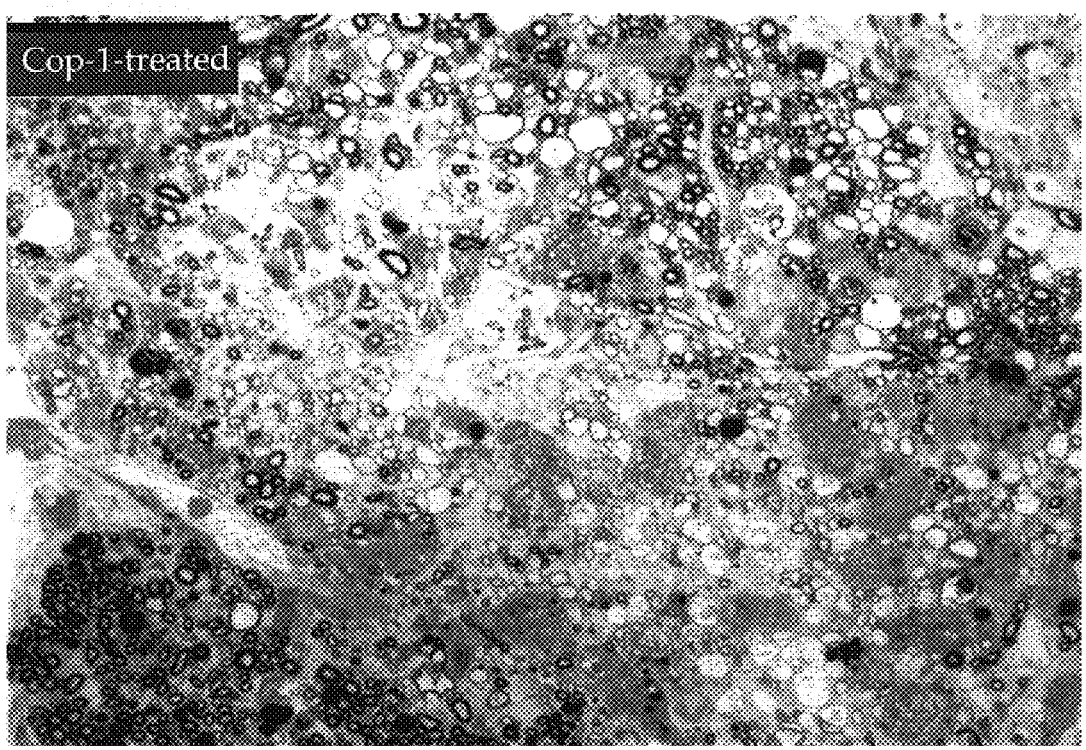
FIGS. 25–26 portray demyelinating lesions from chronically diseased, glatiramer acetate-treated mice (0.1 mg/injection). Lesions show attempts at remyelination.
Figure 26:
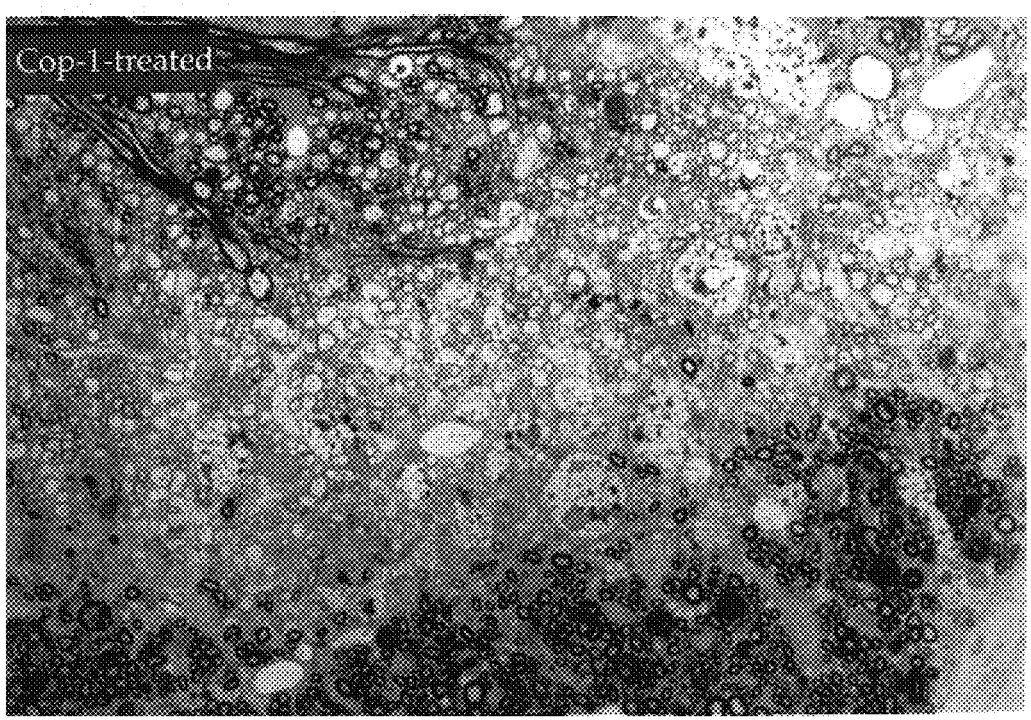

Lesions were extensively demyelinated and infiltrated with macrophages in glatiramer acetate-treated mice (FIGS. 25–26). Patches of significant remyelination were occasionally observed in some lesions, but quantitively, the remyelination was not more extensive than following the PBS treatment.

Treatment with Antibodies Against Glatiramer Acetate

Figure 27:
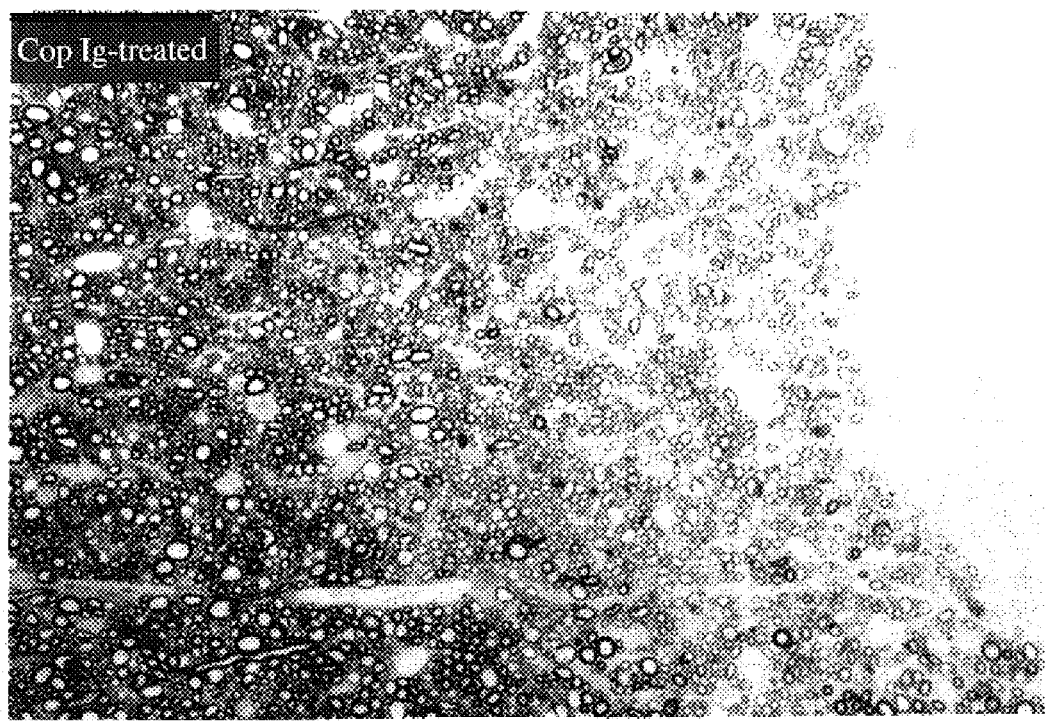
FIGS. 27–28 illustrate demyelinating lesions from chronically diseased, glatiramer acetate antibody-treated mice. Lesions show extensive remyelination (outlined), characterized by thin myelin sheaths around axons.

The lesions of mice treated with antibodies against glatiramer acetate showed extensive oligodendrocyte-mediated remyelination (FIGS. 27–28).

Discussion

Glatiramer acetate has proved to be effective in treating multiple sclerosis (2–6, 31). Due to several inhibitory properties, glatirmaer acetate can be classified as a mixture of latered peptide ligands, an area of major interest in multiple sclerosis research (13, 28). No prior studies have proposed that glatiramer acetate works by inducing the production of polyclonal antibodies against glatiramer acetate. Instead, scientists have theorized that glatiramer acetate disrupts the MHC/TCR complex formation to specific peptides (51), induces glatiramer acetate-specific suppressor cells in vivo (9) or binds directly to major histocompatibility complex class II to replace MBP peptides (5, 69).

Without being limited to any specific mechanism, one hypothesis regarding the mechanism of glatiramer acetate in the treatment of CNS diseases is that it actively induces a protective humoral immune response. In glatirmer acetate-treated multiple sclerosis patients, a Th2 cytokine shift in glatirmaer acetate-reactive lymphocyres occurs, which is consitent with the generation of suppressor lymphocytes (17, 45, 50). Preliminary data indicate that multiple sclerosis patients treated with glatiramer acetate develop very high antibody titers to glatiramer acetate. There seems to be a strong positive correlation between the presence of antibodies against glatiramer acetate and therapeutic efficacy. Another indication that glatiramer acetate stimulates the immune system is evident in the localized swelling and rare hypersensitivity reactions in response to glatiramer acetate. Since the most prevalent aim in multiple sclerosis therapy is to temper immune activity, it is unexpected that a compound that elicits strong immune responses is therapeutic.

One theory concerning the way in which antibodies promote remyelination is that by binding to oligodendrocytes or their progenitors, the antibodies may directly stimulate proliferation or migration of oligodendrocytes, or differentiation of oligodendrocyte progenitors. It is possible to promote remyelination only after approximately 4 months of infection, a time at which most of the active myelin ingestion appears to have subsided. Treatments at earlier than 4 months of infection have not promoted remyelination, suggesting that lesions reach a state of maturation, which poises them for repair.

However, without being limited to any specific mechanism, antibodies against glatiramer acetate appear to promote remyelination through an immunomodulatory mechanism, rather than through direct stimulation of oligodendrocytes or their progenitors. It seems that antibodies against glatiramer acetate bind to activated microglia, macrophages, T cells and possibly to other similar types of cells, such as dendritic cells. Binding to these cells may modulate their functions, thereby facilitating remyelination by oligodendrocytes. This hypothesis is supported by numerous findings of the subject invention. For example, in human glial cell cultures, antibodies against glatiramer acetate appeared to bind microglia by morphological criteria and by the criteria of co-immunostaining with activated microglia markers. The glatiramer acetate-positive cells were distinct from O04-positive oligodendrocytes, which were extensively arborized. Glatiramer acetate antibodies also bound to perivascular infiltrates, further supporting the theory that glatiramer acetate antibodies influence the activity of microglia or macrophages. The binding of antibodies against glatiramer acetate to glial cells differs from other remyelination-promoting antibodies, which bind to oligodendrocytes. Potential effects of the binding of antibodies against glatiramer acetate include alteration in antigen presentation, lymphocyte proliferation, and cytokine/growth factor production. In further support of this hypothesis, antibodies against glatiramer acetate were found to stimulate lymphocyte proliferation in vitro.

Most remyelination-promoting antibodies, including SCH 94.03 (1) are polyreactive autoantibodies derived from germline sequences (11, 42). Therefore, another intriguing possibility is that the complex mixture of peptides comprising glatiramer acetate generated antibodies that mimicked protective, "natural" autoantibodies. In addition, antibodies against glatiramer acetate also had very low polyreactivity to other proteins, unlike other remyelination-promoting antibodies (e.g., SCH 94.03 monoclonal antibody), which crossreact with many protein antigens (1). Furthermore, antibodies against glatiramer acetate comprised a spectrum of antibody isotypes, unlike the predominance of IgMs in other remyelination-promoting antibodies (1). Another possibility is that glatiramer acetate antibodies help to clear debris from lesions through opsonization, thereby permitting spontaneous remyelination to occur more readily.

An apparent paradox is that adoptive transfer of glatiramer acetate antibodies promoted remyelination, yet active immunization did not. In fact, high-dose immunization increased lesion load. This suggests that glatiramer acetate had multiple effects in vivo and that the positive influence of the antibodies was overridden by other effects of active immunization. The most commonly documented effect of glatiramer acetate is suppression of Th1 lymphocyte activity through mechanisms such as induction of Th2 suppressor lymphocytes, inhibition of peptide binding to MHC Class II, and T cell antagonism (8–10, 18, 21, 51, 67). Since glatiramer acetate-mediated suppression is relatively nonspecific (12, 20, 67, 76), and since T lymphocytes are essential for controlling Theiler's virus even during late disease (44, 61), it is possible that antiviral immunity was depressed by glatiramer acetate, resulting in increased viral pathogenesis and lesion exacerbation. This hypothesis is consistent with the increased virus antigen expression, decreased antiviral antibody titers, and decreased TMEV-specific DTH responses. These changes were mild, raising the possibility that glatiramer acetate immunization also expanded lesions through other mechanisms. If synergy between glatiramer acetate antibodies and macrophages or lymphocytes is required for remyelination, then an alteration in the function of these cells by glatiramer acetate (34, 49) could have abrogated remyelination.

A dogma in the multiple sclerosis field is that immune activation, both cellular and humoral, exerts an overwhelmingly deleterious role and must be suppressed for effective therapy. However, it is becoming increasingly clear that the immune system can also be protective in the injured CNS through mechanisms such as secretion of trophic factors (25, 29, 43, 54). For example, following experimental optic nerve damage, glatiramer acetatereactive and MBP reactive lymphocytes reduce secondary neuronal degeneration (43). Myelin repair by glatiramer acetate antibodies exemplifies the therapeutic contribution that humoral activation can make. Maximizing the humoral response to glatiramer acetate through various means can enhance the restoration of conduction and axon health after acute demyelinating attacks.

References

1. U.S. Pat. No. 5,591,629, issued Jan. 7, 1997 (Rodriguez et al.).
2. U.S. Pat. No. 5,800,808, issued Sep. 1, 1998 (Konfino et al.).
3. U.S. Pat. No. 5,981,589, issued Nov. 9, 1999 (Konfino et al.).
4. U.S. Pat. No. 6,048,898, issued Apr. 11, 2000 (Konfino et al.).
5. U.S. Pat. No. 6,054,430, issued Apr. 25, 2000 (Konfino et al.).
6. WO 00/05250, published Feb. 3, 2000 (Aharoni et al.).
7. Aharoni, R. et al. 2000. Specific Th2 cells accumulate in the central nervous system of mice protected against experimental autoimmune encephalomyelitis by copolymer 1. Proc. Natl. Acad. Sci. USA 97: 11472–11477.
8. Aharoni, R., D. Teitelbaum, M. Sela and R. Arnon. 1997. Copolymer 1 induces T cells of the T helper type 2 that crossreact with myelin basic protein and suppress experimental autoimmune encephalomyelitis. Proc. Natl. Acad. Sci. USA 94: 10821–10826.
9. Aharoni, R., D. Teitelbaum and R. Arnon. 1993. T suppressor hybridomas an interleukin-2-dependent lines induce by copolymer 1 or by spinal cord homogenate down-regulate experimental allergic encephalomyelitis. Eur. J. Immunol. 23:17–25.
10. Aharoni, R., D. Teitelbaum, R. Arnon and M. Sela. 1999. Copolymer 1 acts against the immunodominant epitope 82–100 of myelin basic protein by T cell receptor antagonism in addition to major histocompatibility complex blocking. Proc. Natl. Acad. Sci. USA 96: 634–639.
11. Asakura, K., D. J. Muller, R. J. Pogulis, L. R. Pease and M. Rodriguez, 1995. Oligodendrocyte-reactive O1, O4, and HNK-1 monoclonal antibodies are encoded by germline immunoglobulin genes. Molec. Brain Res. 34: 283–293.
12. Ben-Nun, A. et al. 1996. The autoimmune reactivity to myelin oligodendrocyte glycoprotein (MOG)in multiple sclerosis is potentially pathogenic: effect of Copolymer 1 on MOG-induced disease. J. Neurol. 243(Suppl 1): S14–S22.
13. Bielekova, B. et al. 2000. Encephalitogenic potential of the myelin basic protein peptide amino acids 83–99. in multiple sclerosis: Results of a phase II clinical trial with an altered peptide ligand. Nat. Med. 6: 1167–1175.
14. Compston, D. A. S. 1991. "Genetic susceptibility to multiple sclerosis," in McAlpine's Mutiple Sclerosis, Matthews, B. ed., London: Churchill Livingstone, 301–319.
15. Dal Canto, M. C., and H. L. Lipton. 1977. Multiple sclerosis. Animal model: Theiler's virus infection in mice. Am. J. Path. 88:497–500.
16. Darnell et al. 1990. Molecular Cell Biology, $2^{nd}$ ed., New York: Scientific American Books, 172, 768, 778–79, 1038, 1040.
17. Duda, P. W., M. C. Schmied, S. L. Cook, J. I. Krieger and D. A. Hafler, 2000. Glatiramer acetate Copaxone®, induces degenerate, Th2-polarized immune responses in patients with multiple sclerosis. J. Clin. Invest. 105: 967–976.
18. Fridkis-Hareli, M. et al. 1994. Direct binding of myelin basic protein and synthetic copolymer 1 to class II major histocompatibility complex molecules on living antigen-presenting cells—specificity and promiscuity. Proc. Natl. Acad. Sci. USA 91: 4872–4876.
19. Fridkis-Hareli, M., D. Teitelbaum, E. Gurevich, I. Pecht, C. Brautbar, O. J. Kwon, T. Brenner, R. Arnon, and M. Sela. 1994. Direct binding of myelin basic protein and synthetic copolymer 1 to class II major histocompatibility complex molecules on living antigen-presenting cells—specificity and promiscuity. Proc. Natl. Acad. Sci. USA 91:4872–4826.
20. Fridkis-Hareli, M., E. F. Rosloniec, L. Fugger, and J. L Strominger, 1998. Synthetic amino acid copolymers that bind to HLA-DR proteins and inhibit type II collagen-reactive T cells clones. Proc. Natl. Acad. Sci. USA 95: 12528–12531.
21. Fridkis-Hareli, M. and J. L. Strominger, 1998. Promiscuous binding of synthetic copolymer 1 to purified HLA-DR molecules. J. Immunol. 160: 4386–4397.

22. Genain, C. P. et al. 1995. Antibody facilitation of multiple sclerosis-like lesions in a nonhuman primate. J. Clin. Invest. 96: 2966–2974.
23. Hafler, D. A. and H. L. Weiner. 1989. MS: A CNS and systemic autoimmune disease. Immunol. Today 10:104–107.
24. Hawes, G. et al. 1995. Limited restriction in the TCR-alpha beta V region usage of antigen-specific clones. Recognition of myelin basic protein (amino acids 84–102) and Mycobacterium bovis 65-kDa heat shock protein (amino acids 3–13) by T cell clones established from peripheral blood mononuclear cells of monozygotic twins and HLA-identical individuals. J. Immunol. 154:2, 555–566.
25. Huang, D. W., L. McKerracher, P. E. Braun, and S. David, 1999. A therapeutic vaccine approach to stimulate axon regeneration in the adult mammalian spinal cord. Neuron 24: 639–647.
26. Johnson, K. P., B. R. Brooks, J. A. Cohen, C. C. Ford, J. Goldstein, R. P. Lisak, L. W. Myers, H. S. Panitch, J. W. Rose, R. B. Schiffer et al. 1995. Copolymer 1 reduces relapse rate and improves disability in relapsing-remitting multiple sclerosis: results of a phase III multicenter, double-blind placebo-controlled trial. The Copolymer 1 Multiple Sclerosis Study Group. Neurol. 45:1268.
27. Johnson, K. P. et al. 2000. Sustained clinical benefits of glatiramer acetate in relapsing multiple sclerosis patients observed for 6 years. Copolymer 1 Multiple Sclerosis Study Group. Mult. Scler. 6: 255–266.
28. Kappos, L. et al. 2000. Induction of a non-encephalitogenic type 2 T helper-cell autoimmune response in multiple sclerosis after administration of an altered peptide ligand in a placebo-controlled, randomized phase II trial. Nat. Med. 6: 1176–1182.
29. Kerschensteiner, M. et al. 1999. Activated human T cells, B cells, and monocytes produce brain-derived neurotrophic factor in vitro and in inflammatory brain lesions: a neuroprotective role of inflammation?: J. Exp. Med. 189: 865–870.
30. Kipnis, J. et al. 2000. T cell immunity to copolymer 1 confers neuroprotection on the damaged optic nerve: possible therapy for optic neuropathies. Proc. Natl. Acad. Sci. USA 97: 7446–7451.
31. Lampert, P. W. 1978. Autoimmune and virus-induced demyelinating diseases. A review. Am. J. Path. 91:176–208.
32. Lando, Z., D. Teitelbaum and R. Arnon. 1979. Effect of cyclophosphamide on suppressor cell activity in mice unresponsive to EAE. J. Immunol. 123: 2156–2160.
33. Lehrich, J. and B. Arnason. 1976. Demyelinative myelopathy in mice induced by the DA virus. J. Neurol Sci. 29:149.
34. Li, Q., R. Milo, H. Panitch,, P. Swoveland, and C. T. Bever, Jr. 1998. Glatiramer acetate blocks the activation of THP-1 cells by interferon-gamma. Eur. J. Pharmacol. 342: 303–310.
35. Linington, C., M. Bradl,, H. Lassmann, C. Brunner, and K. Vass. 1988. Augmentation of demyelination in rat acute allergic encephalomyelitis by circulating mouse monoclonal antibodies directed against a myelin/oligodendrocyte glycoprotein. Am. J. Pathol. 130: 443–454.
36. Lipton, H. L. and M. C. Dal Canto. 1976. Chronic neurologic disease in Theiler's virus infection of SJL/J mice. J. Neurol. Sci. 30: 201–207.
37. Lisak, R. P. et al. 1983. Effect of treatment with Copolymer 1 (Cop-1) on the in vivo and in vitro manifestations of Experimental Allergic Encephalomyelitis (EAE). J. Neurol. Sci. 62: 281–293.
38. Martyn, C. 1991. "The epidemiology of multiple sclerosis" in McAlpine's Multiple Sclerosis, Matthews, B., ed., London: Churchill Livingstone, 3–40.
39. McGavern, D. B. et al. 1999. Quantitation of spinal cord demyelination, remyelination, atrophy, and axonal loss in a model of progressive neurologic injury. J. Neurosci. Res. 58: 492–504.
40. Miller, D. J., K. Asakura, and M. Rodriguez. 1995. Experimental strategies to promote central nervous system remyelination in multiple sclerosis: insights gained from the Theiler's virus model system. [Review]. J. Neurosci. Res. 41:291.
41. Miller, D. J., K. S. Sanborn, J. A. Katzmann, and M. Rodriguez. 1994. Monoclonal autoantibodies promote central nervous system repair in an animal model of multiple sclerosis. J. Neurosci. 14:6230–6238.
42. Miller, D. J. and M. Rodriguez. 1995. A monoclonal autoantibody that promotes central nervous system remyelination in a model of multiple sclerosis is a natural autoantibody encoded by germline immunoglobulin genes. J. Immunol. 154:2460–2469.
43. Moalem, G. et al. 1999. Autoimmune T cells protect neurons from secondary degeneration after central nervous system axotomy. Nat. Med. 5: 49–55.
44. Murray, P. D., K. D. Pavelko, J. Leibowitz, X. Lin, and M. Rodriguez. 1998. CD4+. and CD8+. T cells make discrete contributions to demyelination and neurologic disease in a viral model of multiple sclerosis. J. Virol. 72: 7320–7329.
45. Neuhaus, O. et al. 2000. Multiple sclerosis: comparison of copolymer-1-reactive T cell lines from treated and untreated subjects reveals cytokine shift from T helper 1 to T helper 2 cells. Proc. Natl. Acad. Sci. USA 97: 7452–7457.
46. Neville, K. L., M. C. Dal Canto, J. A. Bluestone and S. D. Miller. 2000. CD28 costimulatory blockade exacerbates disease severity and accelerates epitope spreading in a virus-induced autoimmune disease. J. Virol. 74: 8349–8357.
47. Olsson, T. 1992. Immunology of multiple sclerosis. Curr. Opin. Neurol. Neurosurg. 5:195–202.
48. Pavelko, K. D., B. G. van Engelen and M. Rodriguez. 1998. Acceleration in the rate of CNS remyelination in lysolecithin-induced demyelination. J. Neurosci. 18: 2498–2505.
49. Pratt, A., A. Al Asmi, P. Duquette and J. P. Antel. 1999. Lymphocyte migration and multiple sclerosis: relation with disease course and therapy. Ann. Neurol. 46: 253–256.
50. Qin, Y., D. Q. Zhang, A. Prat, S. Pouly, and J. Antel. 2000. Characterization of T cell lines derived from glatiramer-acetate-treated multiple sclerosis patients. J. Neuroimmunol. 108: 201–206.
51. Racke, M. K., R. Martin, H. McFarland, and R. B. Fritz. 1992. Copolymer-1-induced inhibition of antigen-specific T cell activation: interference with antigen presentation. J. Neuroimmunol. 37:75.
52. Rader, C. and C. Barbas. 1997. Phage display of combinatorial antibody libraries. Curr. Opin. Biotech. 8:503–508.
53. Raine, C. S., Cannella, B., Hauser, S. L. and Genain, C. P. 1999. Demyelination in primate autoimmune encephalomyelitis and acute multiple sclerosis lesions: a case for antigen-specific antibody mediation [see comments] . Ann. Neurol. 46: 144–146.

54. Rapalino, O. et al. 1998. Implantation of stimulated homologous macrophages results in partial recovery of paraplegic rats. Nat. Med. 4: 814–821.

55. Rodriguez, M. 1991. Immunoglobulins stimulate central nervous system remyelination: electron microscopic and morphometric analysis of proliferating cells. Lab. Invest. 64:358.

56. Rodriguez, M. 1992. Central nervous system demyelination and remyelination in multiple sclerosis and viral models of disease. J. Neuroimmunol. 40:255.

57. Rodriguez, M. and B. Scheithauer. 1994. Ultrastructure of multiple sclerosis. Ultrastruct. Pathol. 18:3.

58. Rodriguez, M., D. J. Miller, and V. A. Lennon. 1996. Immunoglobulins reactive with myelin basic protein promote CNS remyelination. Neurol. 46:538–545.

59. Rodriguez, M. et al. 1987. Theiler's murine encephalomyelitis: a model of demyelination and persistence of virus. Crit. Rev. Immunol. 7:325.

60. Rodriguez, M., L. M. Siegel, D. Hovanec-Burns, L. Bologa and M. C. Graves. 1988. Theiler's virus-associated antigens on the surfaces of cultured glial cells. Viral. 166: 463–474.

61. Rodriguez, M. and M. D. Lindsley. 1992. Immunosuppression promotes CNS remyelination in chronic virus-induced demyelinating disease. Neurol. 42: 348–357.

62. Rodriguez, M. and V. A. Lennon. 1990. Immunoglobulins promote remyelination in the central nervous system. Ann. Neurol. 27:12.

63. Rodriguez, M., V. A. Lennon, E. N. Benveniste, and J. E. Merrill. 1987. Remyelination by oligodendrocytes stimulated by antiserum to spinal cord. J. Neuropathol. Exp. Neurol. 46:84.

64. Sela, M. et al. 1990. Suppressive activity of Cop-1 in EAE and its relevance to multiple sclerosis. Bull. Inst. Pasteur. 88:303–314.

65. Teitelbaum, D., A. Meshorer, T. Hirshfeld, R. Arnon and M. Sela. 1971. Suppression of experimental allergic encephalomyelitis by a synthetic polypeptide. Eur. J. Immunol. 1: 242–248.

66. Teitelbaum, D., C. Webb, A. Meshorer, R. Arnon and M. Sela. 1973. Suppression by several synthetic polypeptides of experimental allergic encephalomyelitis induced in guinea pigs and rabbits with bovine and human basic encephalitogen. Eur. J. Immunol. 3: 273–279.

67. Teitelbaum, D. et al. 1996. Copolymer 1 inhibits chronic relapsing experimental allergic encephalomyelitis induced by proteolipid protein (PLP) peptides in mice and interferes with PLP-specific T cell responses. J. Neuroimmunol. 64: 209–217.

68. Teitelbaum, D., R. Aharoni, M. Sela and R. Arnon. 1991. Cross-reactions and specificities of monoclonal antibodies against myelin basic protein and against the synthetic Copolymer 1. Proc. Natl. Acad. Sci. USA 88:9528–9532.

69. Teitelbaum, D., R. Milo, R. Arnon and M. Sela. 1992. Synthetic copolymer 1 inhibits human T cell lines specific for myelin basic protein. Proc. Natl. Acad. Sci. USA 89:137.

70. Tuohy, V. K. et al. 1989. Identification of an encephalitogenic determinant of myelin proteolipid protein for SJL mice. J. Immunol. 142:5, 1523–1527.

71. Van Engelen, B. G., D. J. Miller, K. D. Pavelko, O. R. Hommes, and M. Rodriguez. 1994. Promotion of remyelination by polyclonal immunoglobulin in Theiler's virus-induced demyelination and in multiple sclerosis. [Review]. J. Neurol. Neurosurg. Psych. 57(Suppl):65.

72. Vaswani, S. K. et al. 1998. Humanized antibodies as potential therapeutic drugs. Ann. Allergy Asthma Immunol. 81:105–119.

73. Warrington, A. E. et al. 2000. Human monoclonal antibodies reactive to oligodendrocytes promote remyelination in a model of multiple sclerosis. Proc. Natl. Acad. Sci. USA 97: 6820–6825.

74. Webb, C. et al. 1973. In vivo and in vitro immunological cross-reactions between basic encephalitogen and synthetic basic polypeptides capable of suppressing Experimental Allergic Encephalomyelitis. Eur. J. Immunol. 3: 279–286.

75. Webb, C. et al. 1976. Molecular requirements involved in suppression of EAE by synthetic basic copolymers of amino acids. Immunochem. 13:333–337.

76. Zhang, M. et al. 2000. Copolymer 1 inhibits experimental autoimmune uveoretinitis. J. Neuroimmunol. 103: 189–194.

77. "Copaxone" in Physician's Desk Reference, 2000, Medical Economics Co., Inc., Montvale, N.J., 3115.

78. Production of monoclonal antibodies. 1991. Curr. Protocols. Unit 2.5.1–2.5.17.

What is claimed is:

1. A monoclonal humanized antibody directed against an epitope on glatiramer acetate.

2. The antibody of claim 1, wherein the antibody is not cross-reactive with myelin basic protein (MBP).

3. The antibody of claim 1, wherein the antibody consists essentially of IgG1.

4. The antibody of claim 1, wherein the antibody does not react with mature oligodendrocytes.

5. The antibody of claim 1, wherein the antibody cross-reacts with spinal cord homogenate (SCH).

6. The antibody of claim 1, wherein the antibody primarily reacts with cells exhibiting a macrophage or microglial phenotype.

7. A $F_{ab}$ fragment of the antibody of claim 1 that binds to an epitope on glatiramer acetate.

8. A pharmaceutical composition comprising the $F_{ab}$ fragment of claim 7 and a pharmaceutically acceptable carrier.

9. A pharmaceutical composition comprising the antibody of claim 1 and a pharmaceutically acceptable carrier.

10. The pharmaceutical composition of claim 9, wherein the antibody is not cross-reactive with myelin basic protein (MBP).

11. The pharmaceutical composition of claim 9, wherein the antibody consists essentially of IgG1.

12. The pharmaceutical composition of claim 9, wherein the antibody does not react with mature oligodendrocytes.

13. The pharmaceutical composition of claim 9, wherein the antibody cross-reacts with spinal cord homogenate (SCH).

14. The pharmaceutical composition of claim 9, wherein the antibody primarily reacts with cells exhibiting a macrophage or microglial phenotype.

* * * * *